(12) United States Patent
Arita et al.

(10) Patent No.: US 9,238,634 B2
(45) Date of Patent: Jan. 19, 2016

(54) ANTI-INFLAMMATORY METABOLITE DERIVED FROM OMEGA-3-TYPE FATTY ACID

(75) Inventors: Makoto Arita, Tokyo (JP); Hiroyuki Arai, Tokyo (JP); Yosuke Isobe, Tokyo (JP); Tadafumi Kubota, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 65 days.

(21) Appl. No.: 13/817,079

(22) PCT Filed: Aug. 4, 2011

(86) PCT No.: PCT/JP2011/004449
§ 371 (c)(1),
(2), (4) Date: Mar. 28, 2013

(87) PCT Pub. No.: WO2012/023254
PCT Pub. Date: Feb. 23, 2012

(65) Prior Publication Data
US 2013/0274327 A1    Oct. 17, 2013

(30) Foreign Application Priority Data
Aug. 19, 2010    (JP) .................................. 2010-184473

(51) Int. Cl.
| | | |
|---|---|---|
| A01N 43/20 | (2006.01) | |
| A01N 43/24 | (2006.01) | |
| A61K 31/335 | (2006.01) | |
| C07D 303/14 | (2006.01) | |
| C07D 303/38 | (2006.01) | |
| C12P 7/64 | (2006.01) | |
| C12P 17/02 | (2006.01) | |
| G01N 30/34 | (2006.01) | |
| G01N 30/72 | (2006.01) | |
| G01N 30/88 | (2006.01) | |

(52) U.S. Cl.
CPC ............ *C07D 303/14* (2013.01); *C07D 303/38* (2013.01); *C12P 7/6427* (2013.01); *C12P 17/02* (2013.01); *C12Y 113/11* (2013.01); *G01N 30/34* (2013.01); *G01N 30/7233* (2013.01); *G01N 2030/884* (2013.01)

(58) Field of Classification Search
USPC ........................................................ 514/475
See application file for complete search history.

(56) References Cited

U.S. PATENT DOCUMENTS

2006/0178347 A1    8/2006    Hammock et al.
2008/0161275 A1    7/2008    Gjorstrup

FOREIGN PATENT DOCUMENTS

WO    WO01 60778 A2    8/2001
WO    WO2006 055965 A2    5/2006

OTHER PUBLICATIONS

G. Cannon, Chapter Nineteen in Burger's Medicinal Chemistry and Drug Discovery, Fifth Edition, vol. I: Principles and Practice, Wiley-Interscience 1995, pp. 783-802.*
Arita, M. "Contributions of Aspirin and Microbial Oxygenase to the Biosynthesis of Anti-inflammatory Resolvins . . . " Biochemical and Biophysical Research Communications, 2005, vol. 338, No. 1, pp. 149-157.
Fer, M. "Metabolism of Eicosapentaenoic and Docosahexaenoic Acids by Recombinant Human Cytochromes P450", Archives of Biochemistry and Biophysics, 2008, vol. 471, No. 2, pp. 116-125.
Fer, M. "Determination of Polyunsaturated Fatty Acid Monoepoxides by High Performance Liquid Chromatography-mass Spectrometry" Journal of Chromatography, 2006, vol. 1115, No. 1-2, pp. 1-7.
Funk, C.D., "Cox-2 Inhibitors and Cardiovascular Risk" Cardiovasc Pharmacol (2007) vol. 50, No. 5, pp. 470-479.
Kato, T., "Preparation of Enantiomers of 19-epoxy Docosahexaenoic Acids and their 4-hydroxy Derivatives" Tetrahedron: Asymmetry (2000) vol. 11, pp. 851-860.
Serhan, C.H. "Resolvins, Docosatrienes, and Neuroprotectins, Novel Omega-e-Derived Mediators, and Their Aspirin-Triggered Endogenous Epimers: An Overview of Their Protective Roles in Catabasis" Prostaglandins and other Lipid Mediators (2004) vol. 73, pp. 155-172.
Singh, G., "Recent Considerations IN Nonsteroidal Anti-Inflammatory Drug Gastrophathy" The American Journal of Medicine (1998) vol. 105(1B), pp. 315-385.
Tjonahen, E., "Resolvin E2: Identification and Anti-Inflammatory Actions: Pivotal Role of Human 5-Lipoxygenase in Resolvin E Series Biosynthesis" Chemistry & Biology (2006), vol. 13, pp. 1193-1202.
European Patent Office Search Report, dated Jan. 8, 2014, which issued during the prosecution of European Patent Application No. EP11817905.0, which corresponds to the present application.

* cited by examiner

*Primary Examiner* — Marcos Sznaidman
(74) *Attorney, Agent, or Firm* — Clark G. Sullivan; Troutman Sanders LLP

(57) ABSTRACT

The purpose is to provide a compound which can overcomes the disadvantages of conventional steroid drugs and NSAID. It is found that specific epoxy monohydroxy forms of eicosapentaenoic acid, docosahexaenoic acid and docosapentaenoic acid which are independently represented by formulae [chemical formula 1], [chemical formula 5] and the like have an inhibitory activity on neutrophils. This compound can inhibit the invasion of neutrophils into tissues and the activation of neutrophils which are observed in acute inflammations.

11 Claims, 22 Drawing Sheets

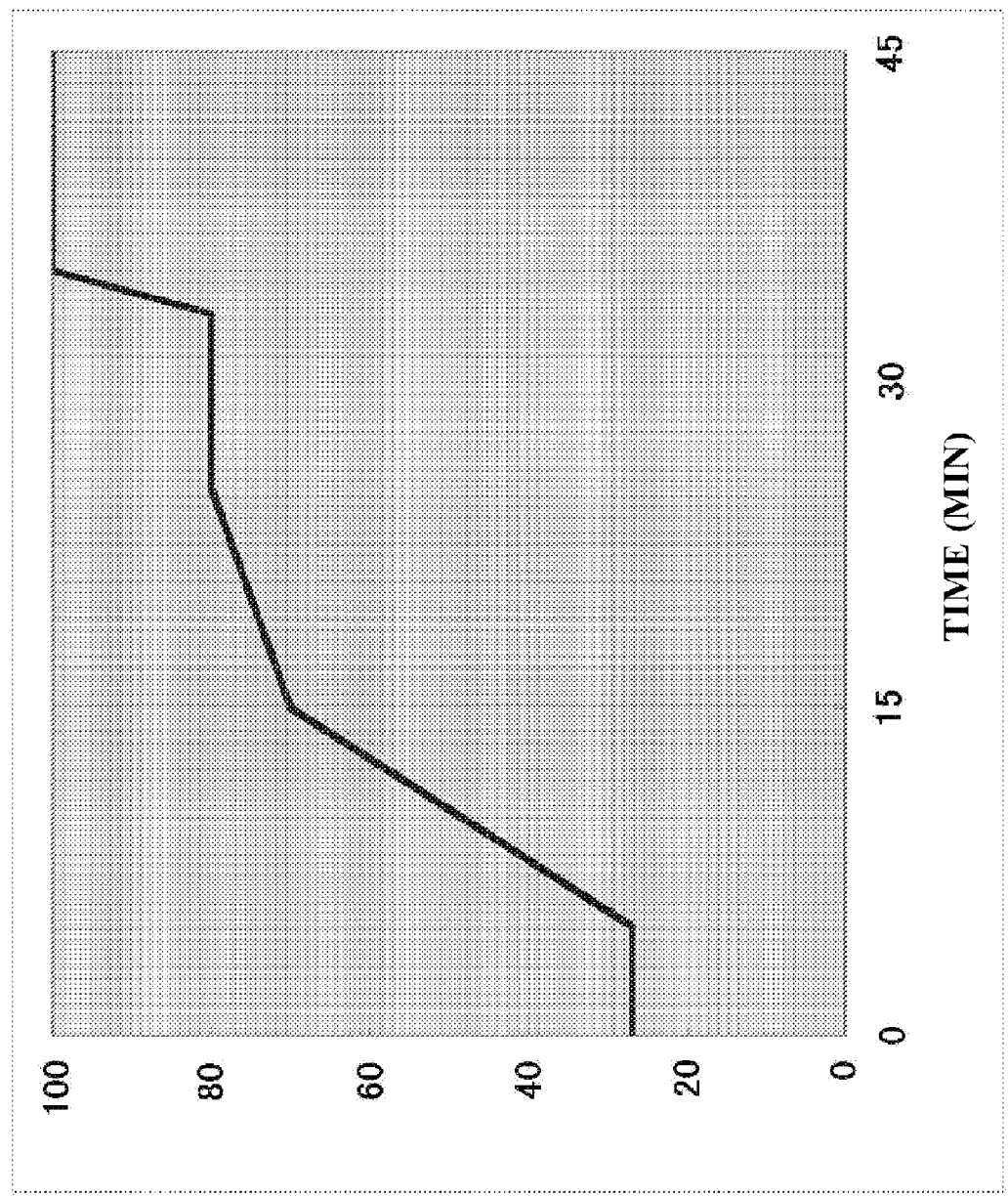

Fig. 1B

| | Q1 | Q3 |
|---|---|---|
| 5hy-17,18-EpETE | 333.2 | 115 |
| 8hy-17,18-EpETE | 333.1 | 155 |
| 12hy-17,18-EpETE | 333.0 | 179 |
| 15hy-17,18-EpETE | 332.9 | 219 |
| 4hy-19,20-EpDPE | 359.1 | 101 |
| 7hy-19,20-EpDPE | 359.0 | 141 |
| 10hy-19,20-EpDPE | 359.0 | 153 |
| 13hy-19,20-EpDPE | 359.0 | 193 |
| 14hy-19,20-EpDPE | 359.0 | 205 |
| 17hy-19,20-EpDPE | 359.0 | 245 |
| 10hy-19,20-EpDTE | 377.0 | 141 |
| 14hy-19,20-EpDTE | 377.0 | 207 |
| 17hy-19,20-EpDTE | 377.1 | 247 |

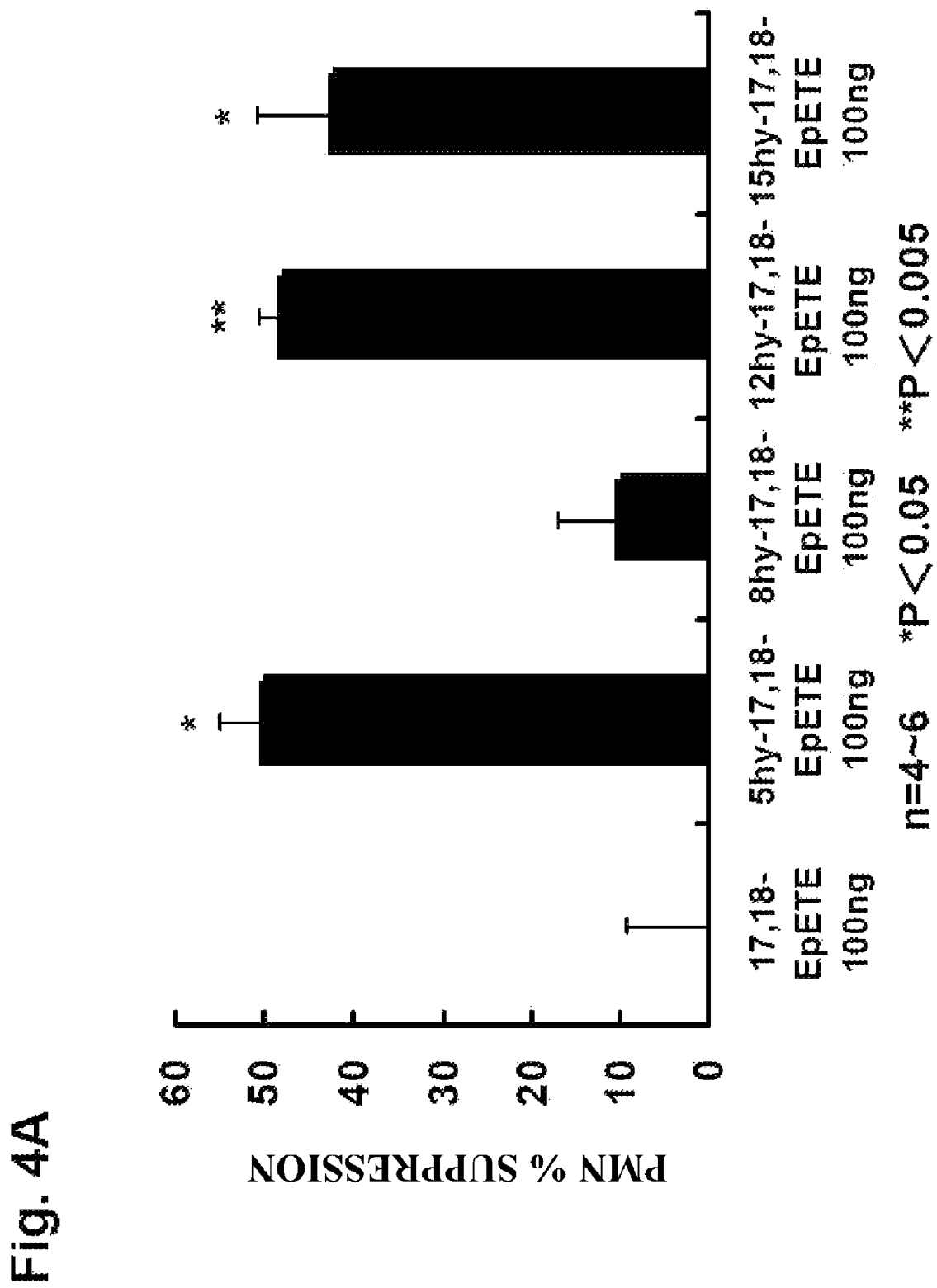

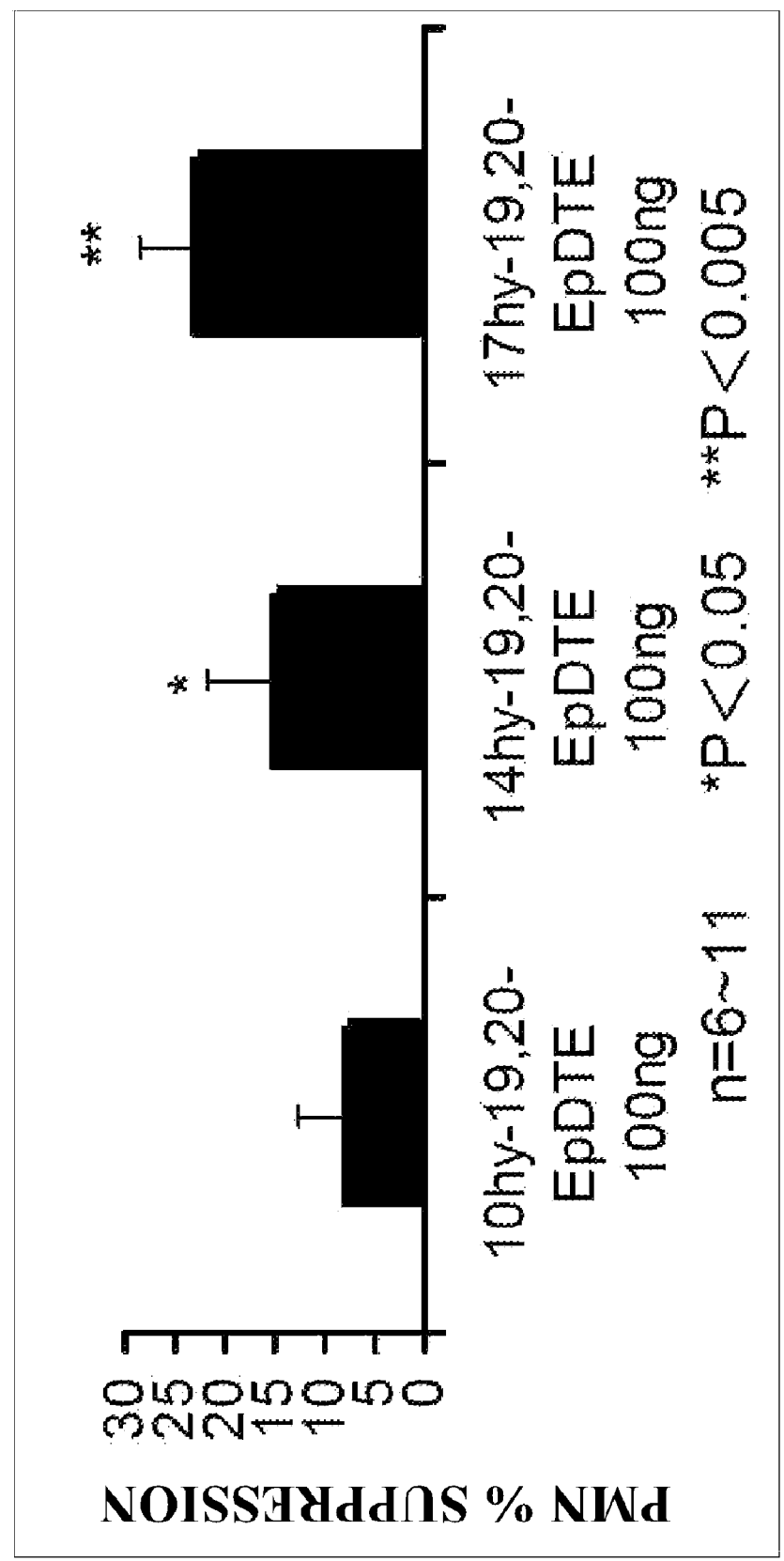

ANTI-INFLAMMATORY METABOLITE DERIVED FROM OMEGA-3-TYPE FATTY ACID

TECHNICAL FIELD

The present invention relates to a novel anti-inflammatory compound.

BACKGROUND ART

Inflammatory disease, in the modern era, is one of the important disease fields for which countermeasures are necessary. Steroids, aspirin and ibuprofen, which are called non-steroidal anti-inflammatories (NSAIDs), and other such substances are representative of drugs currently used as anti-inflammatories.

Among these substances, steroids are used in the treatment of both acute and chronic inflammatory conditions in the clinical setting due to their potent effect. However, problems such as acquisition of resistance due to frequent use, adverse effects, and the like have been pointed out.

Since NSAIDs have an antipyretic analgesic action, they are used as symptomatic therapy. However, it is also known that in NSAIDs, when taken for an extended period of time, damage the gastrointestinal tract, increase the risk of cardiac disease, and allow the progression of inflammatory tissue damage, and this has become a serious problem (Non-patent References 1 and 2).

Substances having hydroxyl groups at position 18 and position 5 of eicosapentaenoic acid (EPA) called resolvin E1 (RvE1: 5S,12R,18R-trihydroxyeicosapentaenoic acid) and other such resolvins and derivatives thereof and substances having hydroxyl groups at position 10 and position 17 of docosahexaenoic acid (DHA) called protectin D1 (PD1) and derivatives thereof are also known to have anti-inflammatory activity (Non-patent References 3 and 4).

The applicant discovered and applied for a patent (International Application PCT/JP2010/52509) on compounds relating to specific dihydroxy forms of eicosapentaenoic acid and docosahexaenoic acid which differ from resolvins and protectins (8,18-dihydroxyeicosapentaenoic acid (8,18-diHEPE), 11,18-dihydroxyeicosapentaenoic acid (11,18-diHEPE), 12,18-dihydroxyeicosapentaenoic acid (12,18-diHEPE), 17,18-dihydroxyeicosapentaenoic acid (17,18-diHEPE). 10,20-dihydroxydocosahexaenoic acid (10,20-diHDoHE), 13,20-dihydroxydocosahexaenoic acid (13,20-diHDoHE), 14,20-dihydroxydocosahexaenoic (14,20-diHDoHE), 19,20-dihydroxydocosahexaenoic (19,20-diHDoHE), and the like).

Derivatives of eicosapentaenoic acid and docosahexaenoic acid which differ from resolvins and protectins are reported to some extent in Patent Reference 1 in addition to the above application. However, there is no mention or suggestion whatsoever of epoxide compounds of eicosapentaenoic acid and docosahexaenoic acid and the like, especially ω3 epoxy compounds further made into hydroxy compounds. Moreover, there is no proof whatsoever that such compounds actually possess anti-inflammatory activity. Non-patent Reference 5 mentions a methyl ester of 4hy-19,20-EpDPE.

PRIOR ART REFERENCES

Patent References

Patent Reference 1: International Publication 2006/055965

Non-Patent References

Non-Patent Reference 1: Singh G. Am. J. Med. 105, 31S-38S (1998)
Non-Patent Reference 2: Funk C. D. and Fitzgerald G. A. J. Cardiovasc Pharmacol 50, 470-479 (2007)
Non-Patent Reference 3: Serhan C. N. et al. Prostaglandins and other Lipid Mediators 73, 155-172 (2004)
Non-Patent Reference 4: E. Tjonahen et al., Chemistry & Biology 13, 1193-1202, November 2006
Non-Patent Reference 5: Tetrahedron Asymmetry (2000), 11(4), 851-860

SUMMARY OF THE INVENTION

Problems to be Solved by the Invention

The purpose of the present invention is to provide compounds of novel structures to resolve the above defects of conventional steroids and NSAIDs.

Means Used to Solve the Problems

The inventors discovered, as a result of in-depth studies, that derivatives originating from specific epoxide compounds of eicosapentaenoic acid, docosahexaenoic acid, and docosapentaenoic acid not known in the past which differ from resolvins and protectins and also differ from specific dihydroxy forms of eicosapentaenoic acid and docosahexaenoic acid (17,18-epoxy-eicosatetraeonic acid (ETE), 19,20-epoxy-docosapentaenoic acid (DPE), and 19,20-epoxy-docosatetraenoic acid DTE)) (5-hydroxy-17,18-epoxy-ETE (5hy-17,18-EpETE), 8-hydroxy-17,18-epoxy-ETE (8hy-17,18-EpETE), 12-hydroxy-17,18-epoxy-ETE (12hy-17,18-EpETE), and 15-hydroxy-17,18-epoxy-ETE (15hy-17,18-EpETE); 4-hydroxy-19,20-epoxy-DPE (4hy-19,20-EpDPE), 7-hydroxy-19,20-epoxy-DPE (7hy-19,20-EpDPE), 10-hydroxy-19,20-epoxy-DPE (10hy-19,20-EpDPE), 13-hydroxy-19,20-epoxy-DPE (13hy-19,20-EpDPE), 14-hydroxy-19,20-epoxy-DPE (14hy-19,20-EpDPE), and 17-hydroxy-19,20-epoxy-DPE (17hy-19,20-EpDPE); and 10-hydroxy-19,20-epoxy-DTE (10hy-19,20-EpDTE), 14-hydroxy-19,20-epoxy-DTE (14hy-19,20-EpDTE), and 17-hydroxy-10,20-epoxy-DTE (17hy-19,20-EpDTE)), and the like (see FIGS. 2A-C) have neutrophil-suppressing activity and solved the above.

Therefore, the present invention provides the following.
(1A) A compound selected from 5-hydroxy-17,18-epoxy-eicosatetraeonic acid (5-hydroxy-17,18-epoxy-ETE, 5hy-17,18-EpETE)

[Chemical Formula 1]

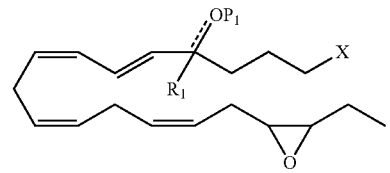

8-hydroxy-17,18-epoxy-eicosatetraenoic acid (8-hydroxy-17,18-epoxy-ETE, 8hy-17,18-EpETE)

[Chemical Formula 2]

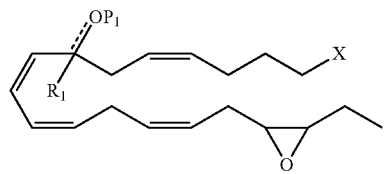

12-hydroxy-17,18-epoxy-eicosatetraenoic acid (12-hydroxy-17,18-epoxy-ETE, 12hy-17,18-EpETE)

[Chemical Formula 3]

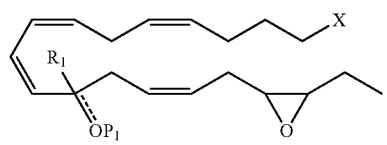

15-hydroxy-17,18-epoxy-eicosatetraenoic acid (15-hydroxy-17,18-epoxy-ETE, 15hy-17,18-EpETE)

[Chemical Formula 4]

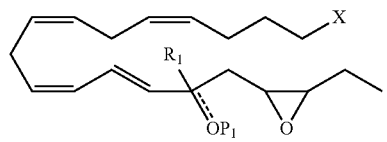

4-hydroxy-19,20-epoxy-docosapentaenoic acid (4-hydroxy-19,20-epoxy-DPE, 4hy-19,20-EpDPE)

[Chemical Formula 5]

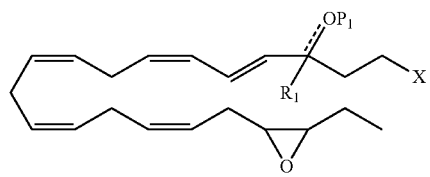

7-hydroxy-19,20-epoxy-docosapentaenoic acid (7-hydroxy-19,20-epoxy-DPE, 7hy-19,20-EpDPE)

[Chemical Formula 6]

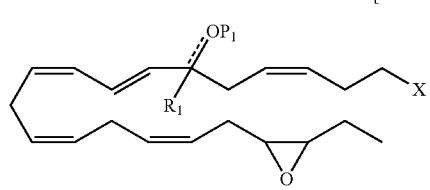

10-hydroxy-19,20-epoxy-docosapentaenoic acid (10-hydroxy-19,20-epoxy-DPE, 10hy-19,20-EpDPE)

[Chemical Formula 7]

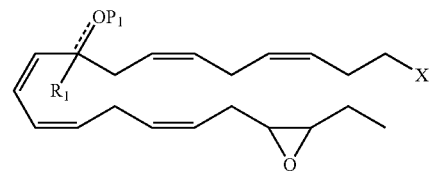

13-hydroxy-19,20-epoxy-docosapentaenoic acid (13-hydroxy-19,20-epoxy-DPE, 13hy-19,20-EpDPE)

[Chemical Formula 8]

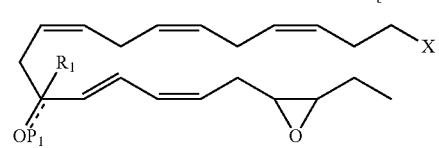

14-hydroxy-19,20-epoxy-docosapentaeonic acid (14-hydroxy-19,20-epoxy-DPE, 14hy-19,20-EpDPE)

[Chemical Formula 9]

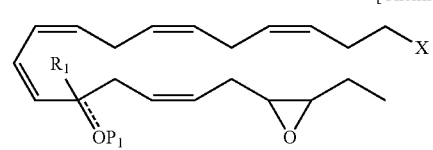

17-hydroxy-19,20-epoxy-docosapentaenoic acid (17-hydroxy-19,20-epoxy-DPE, 17hy-19,20-EpDPE)

[Chemical Formula 10]

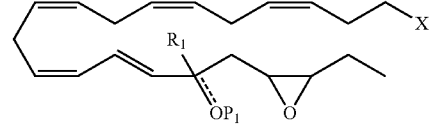

10-hydroxy-19,20-epoxy-docosatetraenoic acid (10-hydroxy-19,20-epoxy-DTE, 10hy-19,20-EpDTE)

[Chemical Formula 11]

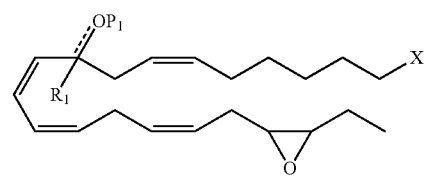

14-hydroxy-19,20-epoxy-docosatetraenoic acid (14-hydroxy-19,20-epoxy-DTE, 14hy-19,20-EpDTE)

[Chemical Formula 12]

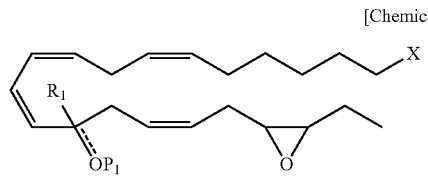

and 17-hydroxy-19,20-epoxy-docosatetraenoic acid (17-hydroxy-19,20-epoxy-DTE, 17hy-19,20-EpDTE)

[Chemical Formula 13]

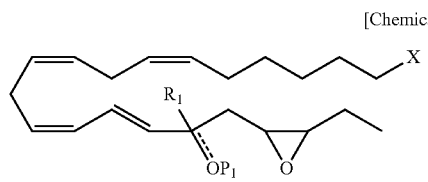

or a solvate of the compound, a pharmaceutically acceptable salt of the compound, or a solvate of the salt; wherein, when

[Chemical Formula 14]

shows a single bond,
$P_1$ is a protecting group, hydrogen atom, alkyl, hydroxy group, or substituted hydroxy group, and
$R_1$ is a hydrogen atom, substituted or unsubstituted, branched or unbranched alkyl group, substituted or unsubstituted aryl group (for example, including also a substituted or unsubstituted, branched or unbranched alkylaryl group); when

[Chemical Formula 15]

shows a double bond, $P_1$ and $R_1$ are not present;
X is —C(O)OR$_2$, —C(O)NR$_3$R$_4$, —C(O)H, —C(NH)NR$_3$R$_4$, —C(S)H, —C(S)OR$_2$, —C(S)NR$_3$R$_4$, —CN;
$R_2$ is a hydrogen, protecting group, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or formula: —NR$_a$R$_b$ (in the formula, R$_a$ and R$_b$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle, or R$_a$ and R$_b$ together with adjacent nitrogen atoms may form a substituted or unsubstituted nitrogen-containing heterocycle);
$R_3$ and $R_4$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle, or $R_3$ and $R_4$ together with adjacent nitrogen atoms may form a substituted or unsubstituted nitrogen-containing heterocycle; and double bonds of the compound may each be independently in either a cis or trans configuration.

(1B)

A compound selected from

[Chemical Formula 16]

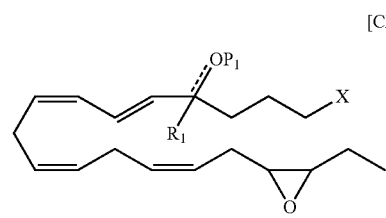

[Chemical Formula 17]

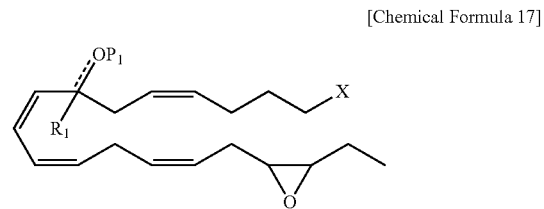

[Chemical Formula 18]

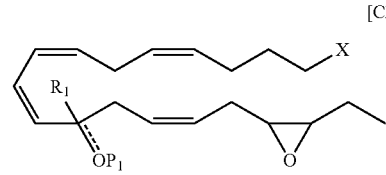

[Chemical Formula 19]

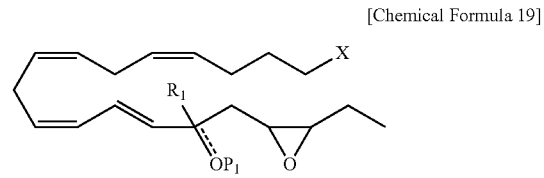

[Chemical Formula 20]

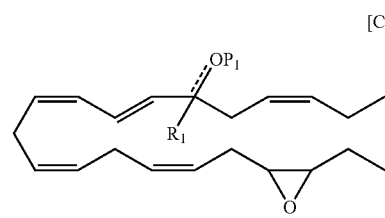

[Chemical Formula 21]

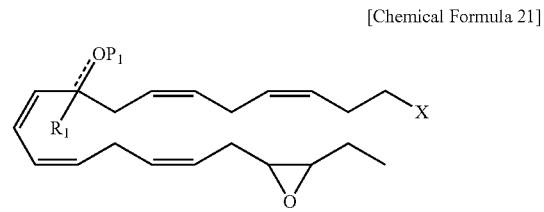

[Chemical Formula 22]

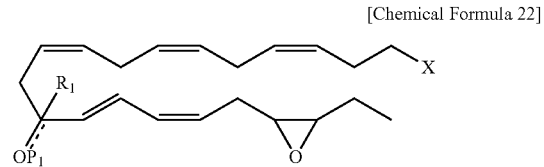

-continued

[Chemical Formula 23]
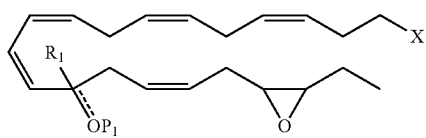

[Chemical Formula 24]
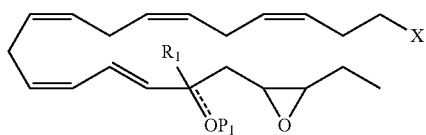

[Chemical Formula 25]
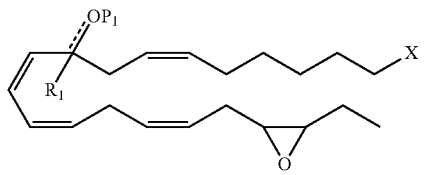

[Chemical Formula 26]
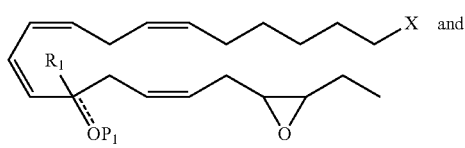 and

[Chemical Formula 27]
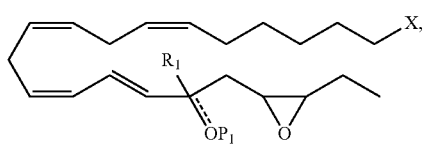

or a solvate of the compound, pharmaceutically acceptable salt of the compound, or solvate of the salt; wherein,
when

[Chemical Formula 28]
----- shows a single bond,
$P_1$ is a protecting group, hydrogen atom, alkyl, hydroxy group, or substituted hydroxy group;
$R_1$ is a hydrogen atom, substituted or unsubstituted, branched or unbranched alkyl group, or substituted or unsubstituted aryl group;
when

[Chemical Formula 29]
----- shows a double bond, $P_1$ and $R_1$ are not present;
X is —C(O)OR$_2$, —C(O)NR$_3$R$_4$, —C(O)H, —C(NH)NR$_3$R$_4$, —C(S)H, —C(S)OR$_2$, —C(S)NR$_3$R$_4$, —CN;
$R_2$ is a hydrogen, protecting group, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or formula: —NR$_a$R$_b$ (in the formula, R$_a$ and R$_b$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle, or R$_a$ and R$_b$ together with adjacent nitrogen atoms may form a substituted or unsubstituted nitrogen-containing heterocycle);
$R_3$ and $R_4$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, or substituted or unsubstituted heterocycle or $R_3$ and $R_4$ together with adjacent nitrogen atoms may form a substituted or unsubstituted nitrogen-containing heterocycle; and
double bonds of the compound may each be independently in either a cis or trans configuration.

(2A) The compound of 1A or 1B, solvate of the compound, pharmaceutically acceptable salt of the compound, or solvate of the salt, wherein the compound is selected from the group consisting of

[Chemical Formula 30]
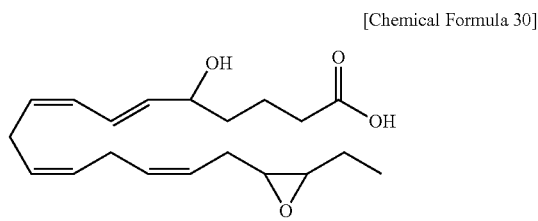

[Chemical Formula 31]
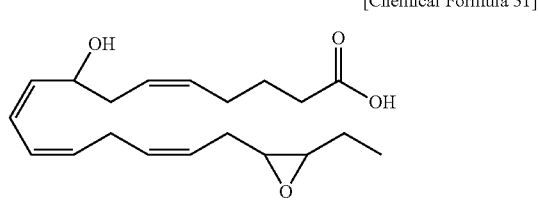

[Chemical Formula 32]
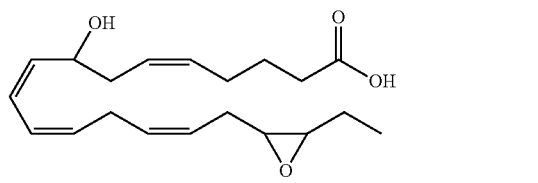

[Chemical Formula 33]
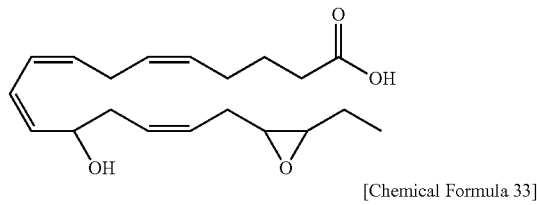

[Chemical Formula 34]
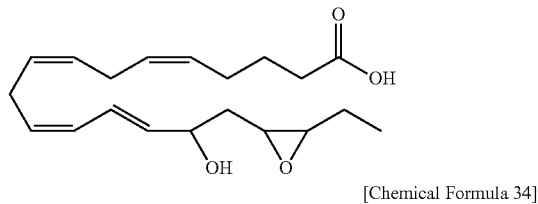

-continued

[Chemical Formula 35]
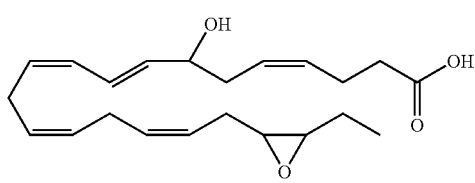

[Chemical Formula 36]
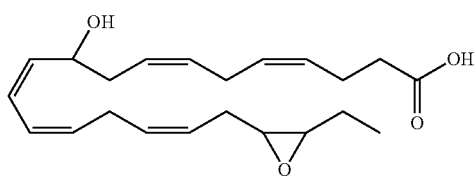

[Chemical Formula 37]
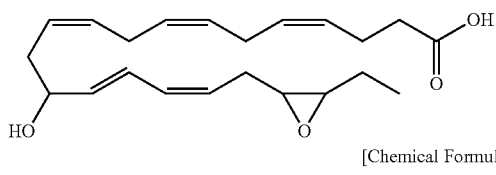

[Chemical Formula 38]
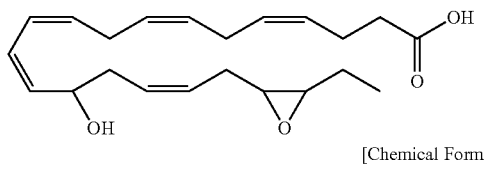

[Chemical Formula 39]
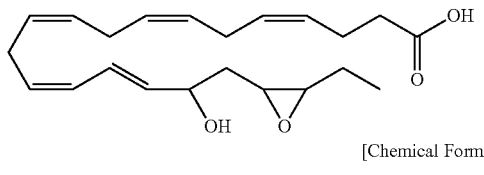

[Chemical Formula 40]
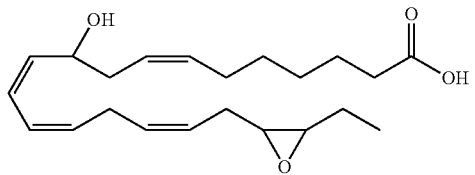

[Chemical Formula 41]
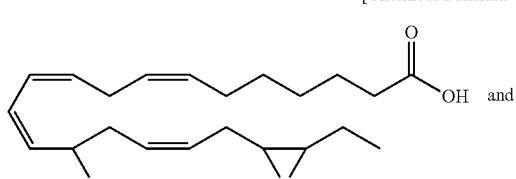

and

[Chemical Formula 42]
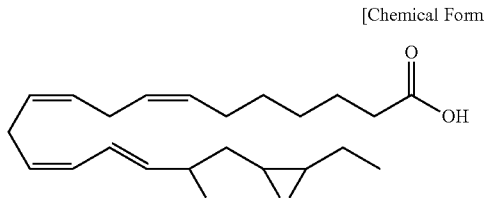

(2B) The compound of 1A or 1B, solvate of the compound, pharmaceutically acceptable salt of the compound, or solvate of the salt, wherein the compound is selected from the group consisting of

[Chemical Formula 43]
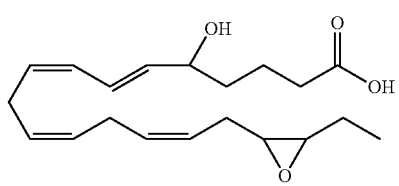

[Chemical Formula 44]
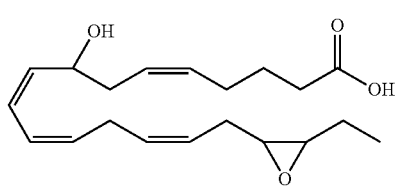

[Chemical Formula 45]
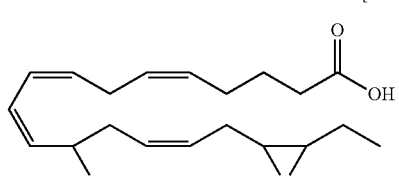

[Chemical Formula 46]
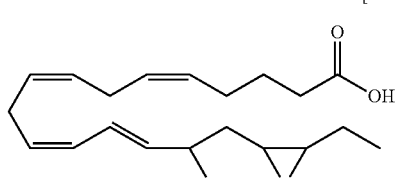

[Chemical Formula 47]
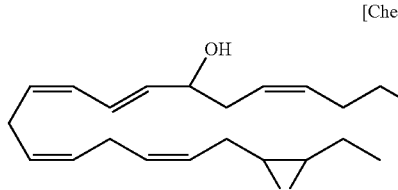

[Chemical Formula 48]
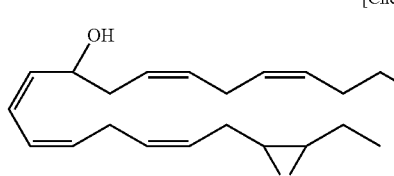

[Chemical Formula 49]
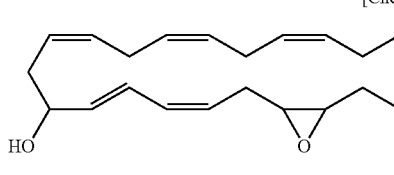

[Chemical Formula 50]
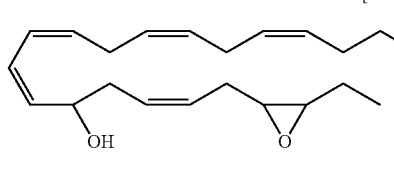

-continued

[Chemical Formula 51]
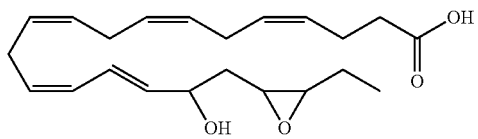

[Chemical Formula 52]
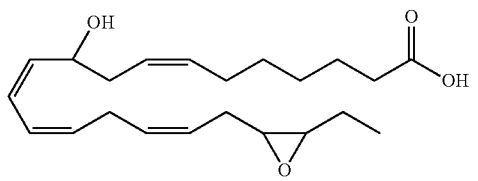

[Chemical Formula 53]
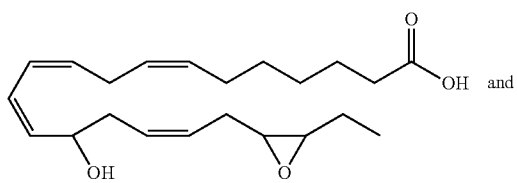

and

[Chemical Formula 54]
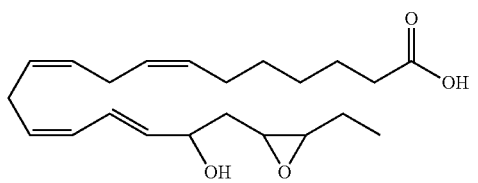

(3) A neutrophil suppressant comprising the compound of 1A, 1B, 2A, or 2B, solvate of the compound, pharmaceutically acceptable salt of the compound, or solvate of the salt.

(4) A drug comprising the compound of 1A, 1B, 2A, or 2B, solvate of the compound, pharmaceutically acceptable salt of the compound, or solvate of the salt.

(5) The drug of 4, wherein the drug is used for the treatment or prevention of a condition, disorder, or state selected from pulmonary conditions selected from pulmonary distress syndrome, adult respiratory distress syndrome, and chronic obstructive pulmonary disease (COPD); ischemic conditions selected from ischemic heart disease, ischemic kidney disease, ischemic brain disease, and ischemic liver disease; inflammatory conditions; and stress-related conditions selected from erosive gastritis, gastric ulcer, duodenal ulcer, bronchial asthma, ulcerative colitis, arteriosclerosis, Crohn's disease, malignant tumor, ovarian cyst, salpingitis, uterine myoma, endometriosis, spontaneous abortion, toxemia of pregnancy, infertility, and dysmenorrhea.

(6) A method for producing the compound of 1A, 1B, 2A, or 2B, solvate of the compound, pharmaceutically acceptable salt of the compound, or solvate of the salt, the method comprising A) a step for obtaining an enzymatic metabolite by contacting at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX) with 17,18-epoxyeicosatetraenoic acid (17,18-epoxy-ETE), 19,20-epoxydocosapentaenoic acid (19,20-epoxy-DPE), or 19,20-epoxydocosatetraenoic acid (19,20-epoxy-DTE); and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(7A) A method for producing the compound of 1A, 1B, 2A, or 2B, solvate of the compound, pharmaceutically acceptable salt of the compound, or solvate of the salt, the method comprising A) a step for obtaining an enzymatic metabolite by contacting an ω3 epoxidase with at least one monohydroxy compound selected from the group consisting of 5-hydroxyeicosapentaenoic acid (5-HEPE), 8-hydroxyeicosapentaenoic acid (8-HEPE), 12-hydroxyeicosapentaenoic acid (12-HEPE), 15-hydroxyeicosapentaenoic acid (15-HEPE), 4-hydroxydocosahexaenoic acid (4-HDoHE), 7-hydroxydocosahexaenoic acid (7-HDoHE), 10-hydroxydocosahexaenoic acid (10-HDoHE), 13-hydroxydocosahexaenoic acid (13-HDoHE), 14-hydroxydocosahexaenoic acid (14-HDoHE), 17-hydroxydocosahexaenoic acid (17-HDoHE), 10-hydroxydocosapentaenoic acid (10-HDoPE), 14-hydroxydocosapentaenoic acid (14-HDoPE), and 17-hydroxydocosapentaenoic acid (17-HDoPE);

B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(7B) A method for producing the compound of 1A, 1B, 2A, or 2B, solvate of the compound, pharmaceutically acceptable salt of the compound, or solvate of the salt, the method comprising A) a step for obtaining an enzymatic metabolite by contacting an ω3 epoxidase with at least one monohydroxy compound selected from the group consisting of 5-hydroxyeicosapentaenoic acid (5-HEPE), 8-hydroxyeicosapentaenoic acid (8-HEPE), 12-hydroxyeicosapentaenoic acid (12-HEPE), 15-hydroxyeicosapentaenoic acid (15-HEPE), 7-hydroxydocosahexaenoic acid (7-HDoHE), 10-hydroxydocosahexaenoic acid (10-HDoHE), 13-hydroxydocosahexaenoic acid (13-HDoHE), 14-hydroxydocosahexaenoic acid (14-HDoHE), 17-hydroxydocosahexaenoic acid (17-HDoHE), 10-hydroxydocosapentaenoic acid (10-HDoPE), 14-hydroxydocosapentaenoic acid (14-HDoPE), and 17-hydroxydocosapentaenoic acid (17-HDoPE);

B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(8A) A method for producing the compound of 1A, 1B, 2A, or 2B, solvate of the compound, pharmaceutically acceptable salt of the compound, or solvate of the salt, the method comprising A) a step for subjecting in any order eicosapentaenoic acid (EPA), docosahexaenoic acid (DHA), or docosapentaenoic acid (DPA) to A1) a step for obtaining an epoxy compound by 17,18-epoxidation or 19,20-epoxidation and A2) a step for obtaining a hydroxy compound by contacting with at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX)

and obtaining an enzymatic metabolite; and

B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(8B) A method for producing the compound of 1A, 1B, 2A, or 2B, solvate of the compound, pharmaceutically acceptable salt of the compound, or solvate of the salt, the method comprising A) a step for subjecting in any order eicosapentaenoic acid (EPA), docosahexaenoic acid (DHA), or docosapentaenoic acid (DPA) to a A1) a step for obtaining an epoxy compound by 17,18-epoxidation or 19,20-epoxidation and A2) a step for obtaining a hydroxy compound by contacting with at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX) and further reduction and obtaining an enzymatic metabolite; and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(9) A method for treating or preventing an inflammatory condition, the method comprising a step for administering the compound of 1A, 1B, 2A, or 2B, solvate of the compound, pharmaceutically acceptable salt of the compound, or solvate of the salt to a subject in need of the treatment or prevention.

(10) Use of the compound of 1A, 1B, 2A, or 2B, solvate of the compound, pharmaceutically acceptable salt of the compound, or solvate of the salt for producing a medicament.

(11) Use of the compound of 1A, 1B, 2A, or 2B, solvate of the compound, pharmaceutically acceptable salt of the compound, or solvate of the salt for producing a medicament to treat or prevent neutrophil-related conditions, disorders, or states.

(12) A method for analyzing the compound of 1A, 1B, 2A, or 2B or a PUFA metabolite, a solvate of the compound or this metabolite, a pharmaceutically acceptable salt of the compound or this metabolite, or a solvate of the salt, comprising the following liquid chromatography conditions:

a solvent system in which the ratio of water to acetic acid in a solution A is 100/0.1, and the ratio of acetonitrile to methanol in a solution B is 4/1; and the flow rate is 50 μL/min at 0-30 min, 80 μL/min at 30-33 min, and 100 μL/min at 33-45; or a modification system thereof; and the parameters listed in FIG. 1A are used.

The MRM parent mass and daughter mass pair from the MS/MS measured values can be optimized (optimization of collision energy) for the synthesized compound under the above setting conditions. Quantitative analysis also becomes possible when a calibration curve is created. MRM for the purpose of detection is performed by setting hypothetical conditions for compounds that are not synthesized.

(13) A product produced by a method comprising

A) a step for obtaining an enzymatic metabolite by contacting at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX) with 17,18-epoxyeicosatetraenoic acid (17,18-epoxy-ETE), 19,20-epoxydocosapentaenoic acid (19,20-epoxy-DPE), or 19,20-epoxydocosatetraenoic acid (19,20-epoxy-DTE); and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(14A) A product produced by a method comprising

A) a step for obtaining an enzymatic metabolite by contacting an ω3 epoxidase with at least one monohydroxy compound selected from the group consisting of 5-hydroxyeicosapentaenoic acid (5-HEPE), 8-hydroxyeicosapentaenoic acid (8-HEPE), 12-hydroxyeicosapentaenoic acid (12-HEPE), 15-hydroxyeicosapentaenoic acid (15-HEPE), 4-hydroxydocosahexaenoic acid (4-HDoHE), 7-hydroxydocosahexaenoic acid (7-HDoHE), 10-hydroxydocosahexaenoic acid (10-HDoHE), 13-hydroxydocosahexaenoic acid (13-HDoHE), 14-hydroxydocosahexaenoic acid (14-HDoHE), 17-hydroxydocosahexaenoic acid (17-HDoHE), 10-hydroxydocosapentaenoic acid (10-HDoPE), 14-hydroxydocosapentaenoic acid (14-HDoPE), and 17-hydroxydocosapentaenoic acid (17-HDoPE); and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(14B) A product produced by a method comprising

A) a step for obtaining an enzymatic metabolite by contacting an ω3 epoxidase with at least one monohydroxy compound selected from the group consisting of 5-hydroxyeicosapentaenoic acid (5-HEPE), 8-hydroxyeicosapentaenoic acid (8-HEPE), 12-hydroxyeicosapentaenoic acid (12-HEPE), 15-hydroxyeicosapentaenoic acid (15-HEPE), 7-hydroxydocosahexaenoic acid (7-HDoHE), 10-hydroxydocosahexaenoic acid (10-HDoHE), 13-hydroxydocosahexaenoic acid (13-HDoHE), 14-hydroxydocosahexaenoic acid (14-HDoHE), 17-hydroxydocosahexaenoic acid (17-HDoHE), 10-hydroxydocosapentaenoic acid (10-HDoPE), 14-hydroxydocosapentaenoic acid (14-HDoPE), and 17-hydroxydocosapentaenoic acid (17-HDoPE); and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(15A) A product produced by a method comprising

A) a step for subjecting in any order eicosapentaenoic acid (EPA), docosahexaenoic acid (DHA), or docosapentaenoic acid (DPA) to A-1) a step for obtaining an epoxy compound by 17,18-epoxidation or 19,20-epoxidation and A-2) a step for obtaining a hydroxy compound by contacting with at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX)

and obtaining an enzymatic metabolite; and

B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

(15B) A product produced by a method comprising

A) a step for subjecting in any order eicosapentaenoic acid (EPA), docosahexaenoic acid (DHA), or docosapentaenoic acid (DPA) to A-1) a step for obtaining an epoxy compound by 17,18-epoxidation or 19,20-epoxidation and A-2) a step for obtaining a hydroxy compound by contacting with at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX) and performing reduction; and obtaining an enzymatic metabolite; and B) a step for reducing or oxidizing the enzymatic metabolite as needed, introducing a substituent as needed, and separating or purifying the target compound, solvate of the compound, pharmaceutically acceptable salt of the compound, or solvate of the salt as needed.

The MRM parent mass and daughter mass pair from the MS/MS measured values can be optimized (optimization of collision energy) for the synthesized compound under the above setting conditions. Quantitative analysis also becomes possible when a calibration curve is created. MRM for the purpose of detection is performed by setting hypothetical conditions for compounds that are not synthesized.

In these all aspects, it is understood that the respective embodiments described in the present specification can be applied in other aspects as far as they are applicable.

A plurality of embodiments are disclosed; however, other embodiments of the present invention will become apparent to a person skilled in the art from the following detailed description. As is apparent, the present invention can be modified in a variety of evident aspects without departing from the technical idea and the scope of the present invention. Therefore, the drawings and the detailed description are deemed to be illustrative and are not deemed to be restrictive.

Advantages of the Invention

The present invention unexpectedly significantly suppresses the infiltration into tissues and activation of neutrophils found at the time of acute inflammation. The compounds of the present invention are compounds not known in the past. Therefore, utility as a new therapeutic is provided.

In addition, since it has been found in the present invention that the compounds of the present invention are also found in vivo, the compounds of the present invention are expected to be therapeutics having few adverse effects in administration over the medium and long term. In addition, since the compounds of the present invention are different from steroids and NSAIDs in their action, the compounds of the present invention are also expected to have an effect as an anti-inflammatory agent by joint use with existing steroids and the like.

BRIEF DESCRIPTION OF THE DRAWINGS

[FIG. 1A] FIG. 1A is a graph showing a gradient used to analyze a compound of the present invention or PUFA metabolite, a solvate of the compound or this metabolite, a pharmaceutically acceptable salt of the compound or this metabolite, or a solvate of the salt. A solvent system using solution A: water/acetic acid=100/0.1 and solution B: acetonitrile/methanol=4/1 was used, and a flow rate: 0-30 min→50 μL/min, 30-33 min→80 μL/min, 33-45 min→100 μL/min was used. The vertical axis is the concentration of solution B, and the horizontal axis is the time (min).

[FIG. 1B] FIG. 1B is a list of the polyunsaturated fatty acid (PUFA) compounds that serve as the objects of measurement by MRM that serve as the subjects in the present invention. In the figure, by represents hydroxy, Ep represents epoxy, EpETE represents epoxyeicosatetraenoic acid, EpDPE represents epoxydocosapentaenoic acid, and EpDTE represents epoxydocosatetraenoic acid.

FIG. 2A shows typical structures of eicosapentaenoic acid (EPA) and omega (ω)epoxide compounds of the present invention produced therefrom.

FIG. 2B shows typical structures of docosahexaenoic acid (DHA) and omega (ω)epoxide compounds of the present invention produced therefrom.

FIG. 2C shows typical structures of docosapentaenoic acid (DPA) and omega (ω)epoxide compounds of the present invention produced therefrom.

FIG. 3A shows the results obtained by mass analysis (MS/MS) of the structural information on compounds derived from EPA. FIG. 3A-1 shows 5-hydroxy-17,18-epoxy-ETE (5hy-17,18-EpETE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3A-2] FIG. 3A shows the results obtained by mass analysis (MS/MS) of the structural information on compounds derived from EPA. FIG. 3A-2 shows 8-hydroxy-17,18-epoxy-ETE (8hy-17,18-EpETE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3A-3] FIG. 3A shows the results obtained by mass analysis (MS/MS) of the structural information on compounds derived from EPA. FIG. 3A-3 shows 12-hydroxy-17,18-epoxy-ETE (12hy-17,18-EpETE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3A-4] FIG. 3A shows the results obtained by mass analysis (MS/MS) of the structural information on compounds derived from EPA. FIG. 3A-4 shows 15-hydroxy-17,18-epoxy-ETE (15hy-17,18-EpETE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3B-1] FIG. 3B shows the results obtained by mass analysis (MS/MS) of the structural information on compounds derived from DHA. FIG. 3B-1 shows 4-hydroxy-19,20-epoxy-DPE (4hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3B-2] FIG. 3B shows the results obtained by mass analysis (MS/MS) of the structural information on compounds derived from DHA. FIG. 3B-2 shows 7-hydroxy-19,20-epoxy-DPE (7hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3B-3] FIG. 3B shows the results obtained by mass analysis (MS/MS) of the structural information on compounds derived from DHA. FIG. 3B-3 shows 10-hydroxy-19,20-epoxy-DPE (10hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3B-4] FIG. 3B shows the results obtained by mass analysis (MS/MS) of the structural information on compounds derived from DHA. FIG. 3B-4 shows 13-hydroxy-19,20-epoxy-DPE (13hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3C-1] FIG. 3C shows the results obtained by mass analysis (MS/MS) of the structural information on compounds derived from DHA. FIG. 3C-1 shows 14-hydroxy-19,20-epoxy-DPE (14hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3C-2] FIG. 3C shows the results obtained by mass analysis (MS/MS) of the structural information on compounds derived from DHA. FIG. 3C-2 shows 17-hydroxy-19,20-epoxy-DPE (17hy-19,20-EpDPE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3D-1] FIG. 3D shows the results obtained by mass analysis (MS/MS) of the structural information on compounds derived from DPA. FIG. 3D-1 shows 10-hydroxy-19,20-epoxy-DTE (10hy-19,20-EpDTE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3D-2] FIG. 3D shows the results obtained by mass analysis (MS/MS) of the structural information on compounds derived from DPA. FIG. 3D-2 shows 14-hydroxy-19,20-epoxy-DTE (14hy-19,20-EpDTE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 3D-3] FIG. 3D shows the results obtained by mass analysis (MS/MS) of the structural information on compounds derived from DPA. FIG. 3D-3 shows 17-hydroxy-19,20-epoxy-DTE (17hy-19,20-EpDTE). The upper figure shows the outflow position (retention time) in liquid chromatography, and the middle figure shows a mass analysis chart (the horizontal axis shows the mass (m/z), the vertical axis shows the signal intensity (relative intensity)), and the lower figure shows the structural formula with identification of the peaks in mass analysis to the right.

[FIG. 4A] FIG. 4A shows an evaluation of the anti-inflammatory activity of compounds of the present invention in a zymosan peritonitis model. The model was produced by inducing acute peritonitis by intraperitoneal administration of 1 mg of zymosan to C57BL6 mice. From the left, 17,18-EpETE, 5-hydroxy-17,18-epoxy-ETE (5hy-17,18-EpETE), 8-hydroxy-17,18-epoxy-ETE (8hy-17,18-EpETE), 12-hydroxy-17,18-epoxy-ETE (12hy-17,18-EpETE), and 15-hydroxy-17,18-epoxy-ETE (15hy-17,18-EpETE) respectively (each compound 100 ng) were injected from a caudal vein of the mouse, and peritonitis was initiated by intraperitoneal administration of 1 mg of zymosan five minutes later. Intraperitoneal cells were recovered two hours later, and the results obtained by analyzing the number of PMN (neutrophils) of each by FACS are shown. The mean of 4-6 studies was taken in each case, and the values show the mean±SEM. * represents $p<0.05$ versus physiological saline (vehicle alone), and ** represents $p<0.005$ versus physiological saline.

FIG. 4B shows an evaluation of the anti-inflammatory activity of compounds of the present invention in a zymosan peritonitis model. The model was produced by inducing acute peritonitis by intraperitoneal administration of 1 mg of zymosan to C57BL6 mice. The same study as in FIG. 4A was conducted using 19,20-EpDPE, 4-hydroxy-19,20-epoxy-DPE (4hy-19,20-EpDPE), 7-hydroxy-19,20-epoxy-DPE (7hy-19,20-EpDPE), 10-hydroxy-19,20-epoxy-DPE (10hy-19,20-EpDPE), 13-hydroxy-19,20-epoxy-DPE (13hy-19,20-EpDPE), 14-hydroxy-19,20-epoxy-DPE (14hy-19,20-EpDPE), and 17-hydroxy-19,20-epoxy-DPE (17hy-19,20-EpDPE). The rest of the procedure was the same as in FIG. 4A. The mean of 3-4 studies was taken, and the values show the mean±SEM. * represents $p<0.05$ versus physiological saline.

FIG. 4C shows an evaluation of the dose dependence of the anti-inflammatory activity of compounds of the present invention in a zymosan peritonitis model. The model was produced by inducing acute peritonitis by intraperitoneal administration of 1 mg of zymosan to C57BL6 mice. The same study as in FIG. 4A was carried out dose dependently. The activity (PMN inhibition) of 12-hy-17,18-EpETE is shown to be dose-dependent in the peritonitis model. The doses varied from 0.44 to 434.3 ng, and the results show the mean±SD [sic]. * represents $p<0.05$ versus physiological saline (vehicle alone), and *** represents $p<0.0005$ versus physiological saline.

[FIG. 4D] FIG. 4D shows an evaluation of the anti-inflammatory activity of compounds of the present invention in a zymosan peritonitis model. The model was produced by inducing acute peritonitis by intraperitoneal administration of 1 mg of zymosan to C57BL6 mice. The same study as in FIG. 4A was conducted using 10-hydroxy-19,20-EpDTE, 14-hydroxy-19,20-EpDTE, and 17-hydroxy-19,20-EpDTE. FIG. 4D shows the data on suppression of neutrophil infiltration. The procedure was the same as in FIG. 4A. The mean of 6-11 studies was taken, and the values show the mean±SEM. * represents $p<0.05$ versus physiological saline, and ** represents $p<0.005$ versus physiological saline.

BEST MODE FOR CARRYING OUT THE INVENTION

Figure 2A:
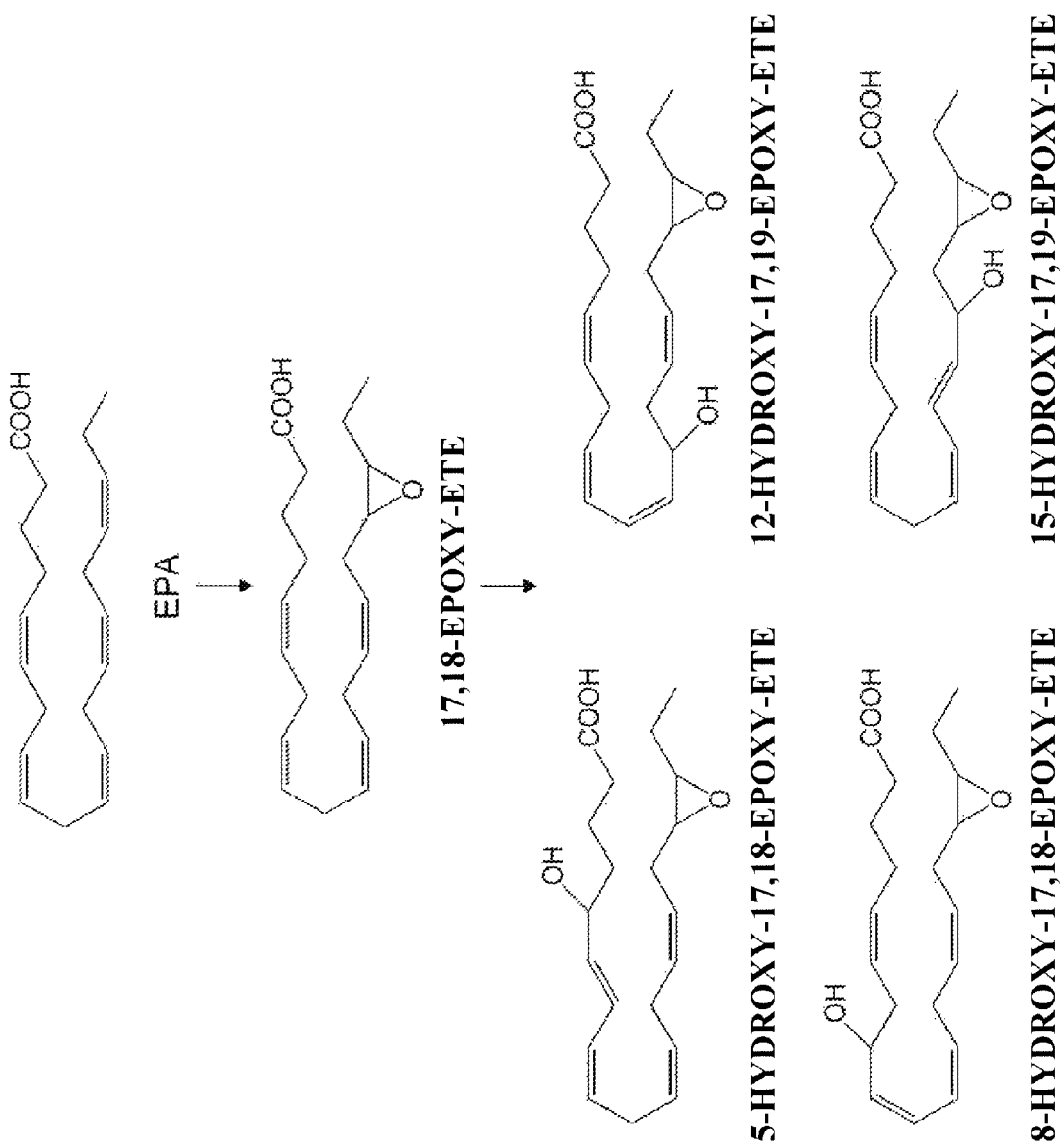
[FIG. 2A]
Figure 2B:
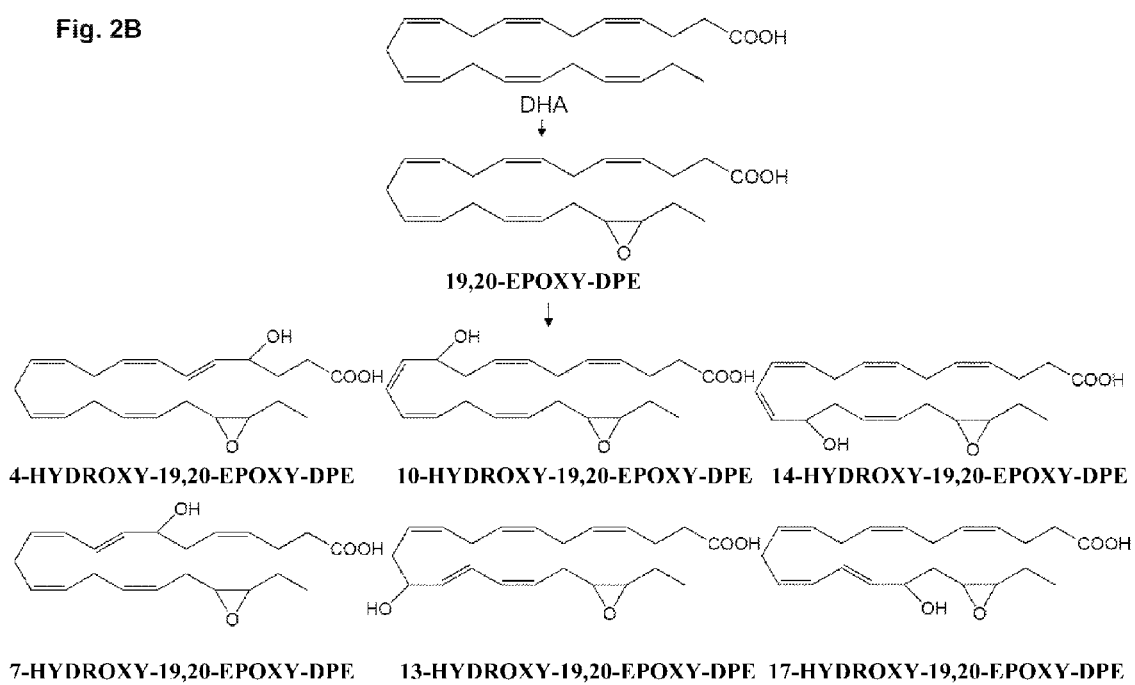
[FIG. 2B]
Figure 2C:
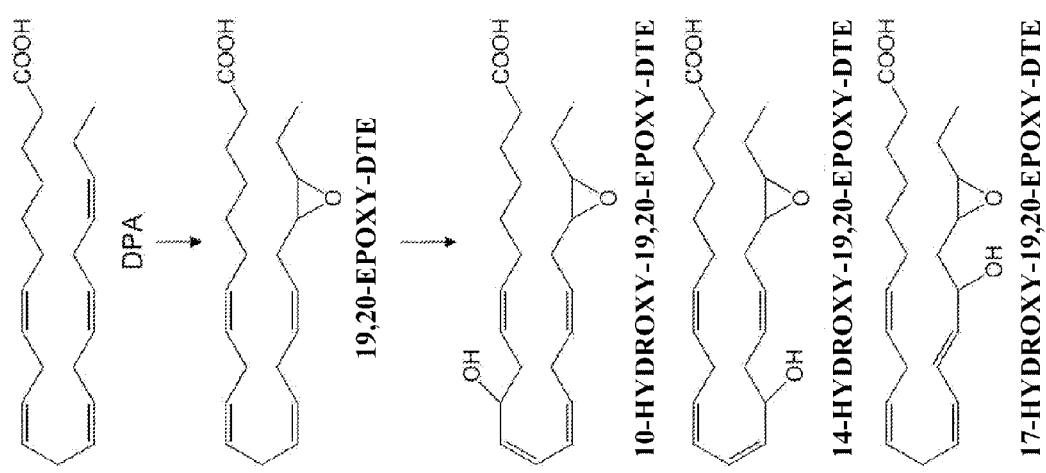
[FIG. 2C]

The present invention will be described below. It should be understood that expression of a singular form also includes the concept of the plural form thereof unless stated otherwise, throughout the present specification. Therefore, it should be understood that an article in the singular form (e.g., "a," "an," "the," and the like in the case of English) also includes the concept of the plural form thereof unless stated otherwise. In addition, it should be understood that the terms used in the present specification are used in the meanings usually used in the art unless stated otherwise. Therefore, unless defined elsewhere, all of the terminology and scientific and technical terms used in the present specification have the same meanings as those that are generally understood by a person skilled in the art to which the present invention pertains. In the case of contradiction, the present specification (including definitions) prevails.

DEFINITION OF TERMS

The following abbreviations are used as needed in the present specification.
COX: cyclooxygenase
DHA: docosahexaenoic acid
DPA: docosapentaenoic acid
DPE: docosapentaenoic acid
Here, DPA and DPE are used interchangeably.
DTE: docosatetraenoic acid
Ep: epoxy
EpDPE: epoxydocosapentaenoic acid
EpDTE: epoxydocosatetraenoic acid
EpETE: epoxyeicosatetraenoic acid
EPA: eicosapentaenoic acid
EPE: eicosapentaenoic acid
Here, EPA and EPE are used interchangeably.
EpEPE: epoxyeicosapentaenoic acid
ETE: eicosatetraenoic acid
HBAA: Hanks' balanced salt solution
HDoHE: hydroxydocosahexaenoic acid
HDoPE: hydroxydocosapentaenoic acid
HEPE: hydroxyeicosapentaenoic acid
HETE: hydroxyeicosatetraenoic acid
HPLC: high-performance liquid chromatography
LC: liquid chromatography
LOX: lipoxygenase
MRM: multiple reaction monitoring
N: normal
PBS: phosphate-buffered saline
PD1: protectin D1
PMN: polymorphonuclear neutrophils
PUFA: polyunsaturated fatty acid
Rv: resolvin
sLOX: soybean lipoxygenase
UPLC: ultra-performance liquid chromatography
(Terms)

The meaning of each of the terms used in the present specification is explained below. Each term is used in a systematic meaning in the present specification and used in the same meaning whether used alone or in combination with other terms.

In the present specification, "halogen" means fluorine, chlorine, bromine, or iodine. Fluorine, chlorine, and bromine are preferred.

In the present specification, "alkyl," by itself or as part of another substituent, means a saturated or unsaturated, branched, linear, or cyclic monovalent hydrocarbon group derived by removing one hydrogen atom from a single carbon atom of a parent alkane having the stated number of carbon atoms (for example, C1-C6, in the present specification, C means carbon and Cn (n shows an integer) means the number of carbon atoms. For example, C1-C6 means 1-6 carbon atoms). It typically encompasses linear or branched monovalent hydrocarbon groups having 1-8 carbon atoms. Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. One example is C1-C6 alkyl. Another example is C1-C4 alkyl. When a number of carbon atoms is specified, it means an "alkyl" having a number of carbon atoms within that numerical range. In the present specification, "substituted or unsubstituted, branched or unbranched alkyl group" is interpreted to indicate an arbitrary alkyl group which is such an alkyl group, which may or may not be substituted, and which may or may not be branched.

In the present specification, "heteroalkyl" means an alkyl in which at least one carbon atom of the above "alkyl" has been substituted by an oxygen atom, sulfur atom, nitrogen atom, or other such hetero atom.

In the present specification, "alkenyl," by itself or as part of another substituent, means an unsaturated branched, linear, or cyclic hydrocarbon group having at least one carbon-carbon double bond derived by removing one hydrogen atom from a single carbon atom of a parent alkene. It typically encompasses linear or branched monovalent hydrocarbon groups having 2-8 carbon atoms and having one or more double bonds. In the group, double bonds may be either a cis configuration or trans configuration. Examples include vinyl, allyl, 1-propenyl, 2-butenyl, 2-pentenyl, 2-hexenyl, 2-heptenyl, 2-octenyl, and the like. One example is C2-C6 alkenyl. Another example if C2-C4 alkenyl.

In the present specification, "alkynyl" encompasses linear or branched monovalent hydrocarbon groups having 2-8 carbon atoms and having one or more carbon-carbon triple bonds. Examples include ethynyl, 1-propynyl, 2-propynyl, 2-butynyl, 2-pentynyl, 2-hexynyl, 2-heptynyl, 2-octynyl, and the like. One example is C2-C6 alkynyl. Another example is C2-C4 alkynyl.

In the present specification, "diyl" of alkyl, alkenyl, or alkynyl, by itself or as part of another substituent, means a saturated or unsaturated branched, linear, or cyclic divalent hydrocarbon group having the stated number of carbon atoms (that is, C1-C6 means 1-6 carbon atoms) derived by removing one hydrogen atom from each of two different carbon atoms of a parent alkane, alkene, or alkyne or by removing two hydrogen atoms from a single carbon atom of a parent alkane, alkene, or alkyne. Each valence of the center of two monovalent groups or the center of a divalent group can form bonds with the same atom or different atoms. Typical diyl groups include, but are not limited to, the following: methanediyl; ethane-1,1-diyl, ethane-1,2-diyl, ethene-1,1-diyl, ethene-1,2-diyl, and other such ethyldiyls; propane-1,1-diyl, propane-1,2-diyl, propane-2,2-diyl, propane-1,3-diyl, cyclopropane-1,1-diyl, cyclopropane-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-in-1,3-diyl, and other such propyldiyls; butane-1,1-diyl, butane-1,2-diyl, butane-1,3-diyl, butane-1,4-diyl, butane-2,2-diyl, 2-methyl-propane-1,1-diyl, 2-methyl-propane-1,2-diyl, cyclobutane-1,1-diyl; cyclobutane-1,2-diyl, cyclobutane-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propane-1,1-diyl, buta-1,3-diene-1,1-diyl, buta-1,3-diene-1,2-diyl, buta-1,3-diene-1,3-diyl, buta-1,3-diene-1,4-diyl, cyclobut-1-en-1,2-diyl, cyclobut-1-en-1,3-diyl, cyclobut-2-en-1,2-diyl, cyclobuta-1,3-diene-1,2-diyl, cyclobuta-1,3-diene-1,3-diyl, but-1-in-1,3-diyl, but-1-in-1,4-diyl, buta-1,3-diine-1,4-diyl, and other such butyldiyls; and the like. When saturation of a specific level is intended, the nomenclature alkyldiyl, alkenyldiyl and/or alkynyldiyl is used. When two valences are intended in particular on the same carbon atom, the nomenclature "alkylidene" is used. In a preferred embodiment, an alkyldiyl group is a (C1-C6) alkyldiyl. A saturated, noncyclic alkanyldiyl group in which the center of the group is on a carbon of an end, for example, methanediyl(methano); ethane-1,2-diyl (ethano); propane-1,3-diyl(propano); butane-1,4-diyl(butano); and the like are also preferred (also called "alkyleno").

In the present specification, "cycloalkyl," by itself or as part of another substituent, means a cyclic hydrocarbon group derived by removing one hydrogen atom from a single carbon atom of a parent cycloalkane. It typically encompasses cycloalkyls having 3-8 carbon atoms. Examples include cyclopropyl, cyclobutyl, cyclopentyl, cyclohexyl, cycloheptyl, and cyclooctyl. One example is C3-C6 cycloalkyl.

In the present specification, "cycloalkenyl," by itself or as part of another substituent, means an unsaturated cyclic hydrocarbon group having at least one carbon-carbon double bond derived by removing one hydrogen atom from a single carbon atom of a parent cycloalkane. It typically encompasses cycloalkenyls having 3-8 carbon atoms. Examples include cyclopropenyl, cyclobutenyl, cyclopentenyl, cyclohexenyl, and cycloheptenyl. One example is C3-C6 cycloalkenyl.

In the present specification, examples of "alkoxy" or "alkyloxy" include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like. Preferred examples are C1-C6 alkyloxy. More preferred examples are C1-C4 alkyloxy. When a number of carbon atoms is specified, it means "alkoxy" or "alkyloxy" having a number of carbon atoms within that numerical range.

In the present specification, examples of "alkylsulfonyl" include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl, and the like. Preferred examples are C1-C6 alkylsulfonyls. More preferred examples are C1-C4 alkylsulfonyl.

In the present specification, examples of "alkyloxycarbonyl" include methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, and the like. One example is C1-C4 alkyloxycarbonyl. Another example is C1-C2 alkyloxycarbonyl.

In the present specification, "acyl" includes formyl, alkylcarbonyl, alkenylcarbonyl, cycloalkylcarbonyl, cycloalkenylcarbonyl, arylcarbonyl, heteroarylcarbonyl, and heterocycle carbonyl. Examples include acetyl, propionyl, butyroyl, and benzoyl.

In the present specification, "lower alkyl" includes linear or branched alkyls having 1 to 6 carbon atoms, and preferably 1 to 3 carbon atoms. Examples include methyl, ethyl, n-propyl, isopropyl, n-butyl, isobutyl, sec-butyl, tert-butyl, n-pentyl, isopentyl, neopentyl, hexyl, and isohexyl.

The lower alkyl part of "lower alkoxy," "hydroxy lower alkyl," "hydroxy lower alkoxy," "lower alkoxycarbonyl," "lower alkylamino," "lower alkoxy lower alkoxy," "lower alkylcarbamoyl," "hydroxy lower alkylcarbamoyl," "lower alkoxyimino," "lower alkylthio," "lower alkylsulfonyl," "lower alkylsulfonyloxy," "lower alkylsulfamoyl," and "lower alkylsulfinyl" is also the same as the above "lower alkyl".

In the present specification, a "substituted or unsubstituted lower alkyl" may be substituted, preferably substituted by one or more groups selected from substituent group α.

Herein, the substituent group α is a group consisting of halogens, hydroxy, lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfinyl, cyano, nitro, carbocyclic groups, and heterocyclic groups.

In the present specification, "lower alkenyl" includes linear or branched alkenyl having 2 to 15 carbon atoms, preferably 2 to 10 carbon atoms, more preferably 2 to 6 carbon atoms, and even more preferably 2 to 4 carbon atoms, and having one or more double bonds at an arbitrary position. Specific examples include vinyl, aryl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl, and the like.

In the present specification, "lower alkynyl" includes linear and branched alkynyl having 2 to 10 carbon atoms, preferably 2 to 8 carbon atoms, more preferably 3 to 6 carbon atoms, and having one or more triple bonds at an arbitrary position. Specific examples include ethynyl, propynyl, butynyl, pentynyl, hexynyl, heptynyl, octynyl, nonynyl, decynyl, and the like. These may also have double bonds at arbitrary positions.

In the present specification, "carbocyclic group" includes cycloalkyl, cycloalkenyl, aryl, non-aromatic condensed carbocyclic groups, and the like.

In the present specification, "substituted or unsubstituted amino" includes amino which may be substituted at one or two positions with the "alkyl" described above, the "aryl" described later, the "heteroaryl" described later, the "heterocycle" described later, the "acyl" described above, the "alkyloxycarbonyl" described above, the "alkylsulfonyl" described above, the "arylsulfonyl" described later, the "heteroarylsulfonyl" described later, and the "heterocycle sulfonyl" described later. Examples include amino, methylamino, dimethylamino, ethylamino, diethylamino, ethylmethylamino, benzylamino, acetylamino, benzoylamino, methyloxycarbonylamino, methylsulfonylamino, and the like. Preferred examples include amino, methylamino, dimethylamino, ethylmethylamino, diethylamino, acetylamino, and methylsulfonylamino.

In the present specification, "substituted or unsubstituted carbamoyl" includes substituted or unsubstituted aminocarbonyl in which the substituted or unsubstituted amino moiety is the "substituted or unsubstituted amino" described above. Examples include carbamoyl, N-methylcarbamoyl, N,N-dimethylcarbamoyl, N-ethyl-N-methylcarbamoyl, N,N-diethylcarbamoyl, N-benzylcarbamoyl, N-acetylcarbamoyl, N-methylsulfonylcarbamoyl, and the like. Preferred examples include carbamoyl, N-methylcarbamoyl, N,N-dimethylcarbamoyl, N-methylsulfonylcarbamoyl, and the like.

In the present specification, "aryl" includes monocyclic or condensed cyclic aromatic hydrocarbon groups. It may be condensed at all possible positions with the "cycloalkyl" described above, the "heteroaryl" described later, and the "heterocycle" described later. Whether the aryl is monocyclic or a condensed ring, it can bond at all possible positions. Examples include phenyl, 1-naphthyl, 2-naphthyl, anthryl, tetrahydronaphthyl, 1,3-benzodioxolyl, 1,4-benzodioxanyl, and the like. Preferred examples are phenyl, 1-naphthyl, and 2-naphthyl. A more preferred example is phenyl.

In the present specification, "heterocyclic (group)," "heterocyclic ring (group)," and "heterocycle (group)" are used interchangeably and include non-aromatic heterocyclic groups optionally having a bond at an arbitrary substitutable position and optionally having 1-4 hetero atoms such as an oxygen atom, sulfur atom, nitrogen atom, or the like in the ring. Such non-aromatic heterocyclic groups may also be crosslinked by alkyl chains having 1-4 carbon atoms and may be condensed with a cycloalkane (preferably a 5- to 6-membered ring) or benzene ring. They may be saturated or unsaturated as long as they are non-aromatic. A 5- to 8-membered ring is preferred, but non-aromatic heterocycles may also condense. Examples include pyrrolinyl (e.g., 1-pyrrolinyl, 2-pyrrolinyl, 3-pyrrolinyl), pyrrolidinyl (e.g., 1-pyrrolidinyl, 2-pyrrolidinyl, 3-pyrrolidinyl), pyrrolidinone, imidazolinyl (e.g., 1-imidazolinyl, 2-imidazolinyl, 4-imidazolinyl), imidazolidinyl (e.g., 1-imidazolidinyl, 2-imidazolidinyl, 4-imidazolidinyl), imidazolidinone, pyrazolinyl (e.g., 1-pyrazolinyl, 3-pyrazolinyl, 4-pyrazolinyl), pyrazolidinyl (e.g., 1-pyrazolidinyl, 3-pyrazolidinyl, 4-pyrazolidinyl), piperidinone, piperidine, piperidinyl (e.g., 2-piperidinyl, 3-piperidinyl, 4-piperidinyl), piperazinyl (e.g., 1-piperazinyl, 2-piperazinyl), piperazinone, morpholinyl (e.g., 2-morpholinyl, 3-morpholinyl), morpholino, tetrahydropyranyl, tetrahydrofuranyl, and the like.

In the present specification, "heteroaryl" includes 5- to 6-membered aromatic rings containing one or more arbitrarily selected hetero atoms such as an oxygen atom, sulfur atom, nitrogen atom, or the like in the ring. "Heteroaryl" includes those among "heterocycles" that are aromatic cyclic groups. They may be condensed at all possible positions with the "cycloalkyl" described above, the "aryl" described above, the "heterocycle" described above, or other heteroaryls. Whether the heteroaryl is monocyclic or a condensed ring, it can bond at all possible positions. Examples include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl, 4-pyrazolyl), isothiazolyl (e.g., 3-isothiazolyl), isoxazolyl (e.g., 3-isoxazolyl), oxazolyl (e.g., 2-oxazolyl, 4-oxazolyl, 5-oxazolyl), thiazolyl (e.g., 2-thiazolyl, 4-thiazolyl, 5-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadizolyl), thiadiazolyl (e.g., 1,3,4-thiadiazolyl), indolizinyl (e.g., 2-indolizinyl, 6-indolizinyl), isoindolyl (e.g., 2-isoindolyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), benzodioxolyl (e.g., 1,3-benzodioxolyl), and the like.

In the present specification, "heterocyclic (group)" includes heterocyclic groups having one or more heteroatoms arbitrarily selected from an oxygen atom, sulfur atom, nitrogen atom, and the like in the ring. Specific examples include 5- to 6-membered heteroaryls such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, or thiadiazolyl; non-aromatic heterocyclic groups such as dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, and tetrahydropyridazinyl; bicyclic condensed heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzoxezinyl, dihydrobenzodioxepinyl, and dihydrothienodioxynyl; and tricyclic condensed heterocyclic groups such as carbazolyl, acridinyl, xanthenyl, phenothiazinyl, phenoxathiinyl, phenoxazinyl, dibenzofuryl, imidazoquinolyl, and tetrahydrocarbazolyl; and the like. Preferred are 5- to 6-membered heteroaryls or nonaromatic heterocyclic groups.

In the present specification, "alkylene" means linear or branched alkylene having 1 to 10 carbon atoms. Examples include methylene, 1-methylmethylene, 1,1-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene, and the like. Linear or branched alkylenes having 2 to 6 carbon atoms are especially preferred.

In the present specification, "alkenylene" means linear or branched alkenylene having 2 to 10 carbon atoms. Examples include ethenylene, 1-methylethenylene, 1-ethylethenylene, 1,2-dimethylethenylene, 1,2-diethyl-ethenylene, 1-ethyl-2-methylethenylene, propenylene, 1-methyl-2-propenylene, 2-methyl-2-propenylene, 1,1-dimethyl-2-propenylene, 1,2-dimethyl-2-propenylene, 1-ethyl-2-propenylene, 2-ethyl-2- propenylene, 1,1-diethyl-2-propenylene, 1,2-diethyl-2-propenylene, 1-butenylene, 2-butenylene, 1-methyl-2-butenylene, 2-methyl-2-butenylene, 1,1-dimethyl-2-butenylene, 1,2-climethyl-2-butenylene, and the like. Linear or branched alkenylenes having 2 to 6 carbon atoms are especially preferred.

In the present specification, "alkynylene" includes a linear or branched divalent carbon chain having 2 to 10 carbon atoms, preferably 2 to 6 carbon atoms, preferably 2 to 4 carbon atoms, which has a triple bond at an arbitrary position and may also have a double bond. Specific examples include ethynylene, propynylene, butynylene, pentynylene, hexynylene, and the like.

In the present specification, the alkyl moiety of "alkylcarbonyl" means the above "alkyl."

In the present specification, the alkenyl moiety of "alkenyloxy" and "alkenylcarbonyl" mean the above "alkenyl."

In the present specification, the aryl moiety of "aryloxy" and "arylcarbonyl" mean the above "aryl."

In the present specification, the heteroaryl moiety of "heteroarylcarbonyl" means the above "heteroaryl."

In the present specification, the heterocycle moiety of "heterocycle carbonyl" means the above "heterocycle."

In the present specification, the aryl moiety of "arylsulfonyl" means the above "aryl."

In the present specification, the heteroaryl moiety of "heteroarylsulfonyl" means the above "heteroaryl."

In the present specification, the heterocycle moiety of "heterocycle sulfonyl" means the above "heterocycle."

In the present specification, examples of a typical heteroatom and/or heteroatom group which can replace a carbon atom include, but are not limited to, the followings: —O—, —S—, —S—O—, —NR'—, —PH—, —S(O)—, —S(O)$_2$, —S(O)NR'—, —S(O)$_2$NR'—, and the like, and combinations thereof. Herein, each R' is independently a hydrogen or a (C1-C6) alkyl.

In the present specification, "aromatic ring system" refers to an unsaturated ring or polycyclic ring system having a conjugated $\pi$ electron system. A condensed ring system in which one or more rings are aromatic and one or more rings are saturated or unsaturated, for example, fluorene, indane, indene, phenalene, tetrahydronaphthalene, and the like are specifically included in the definition of an "aromatic ring system". Typical examples of the parent aromatic ring system include, but are not limited to, the following: aceanthrylene, acenaphthylene, acephenanthrylene, anthracene, azulene, benzene, chrysene, coronene, fluorancene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as a variety of hydro isomers thereof.

In the present specification, "non-aromatic condensed carbocyclic group" includes groups in which two or more cyclic groups selected from the above "cycloalkyl," "cycloalkenyl," and "aryl" are condensed. Specific examples include indenyl, indenyl, tetrahydronaphthyl, fluorenyl, and the like.

In the present specification, examples of the substituents of the "substituted or unsubstituted carbocyclic group" and "substituted or unsubstituted heterocycle" are arbitrary substituents. Preferred examples are one or more groups selected from the group consisting of lower alkyls and substituent group α.

In the present specification, substituents of "substituted or unsubstituted alkyl," "substituted or unsubstituted alkenyl," "substituted or unsubstituted alkynyl," "substituted or unsubstituted aryl," "substituted or unsubstituted cycloalkyl," "substituted or unsubstituted cycloalkenyl," "substituted or unsubstituted heteroaryl," "substituted or unsubstituted heterocycle," "substituted or unsubstituted acyl," "substituted or unsubstituted alkoxy," "substituted or unsubstituted alkylene," "substituted or unsubstituted alkenylene," and "substituted or unsubstituted alkynylene" are selected, for example, from the group consisting of hydroxy, carboxy, halogen, alkyl halide (e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantly), cycloalkylalkyl (e.g., cyclohexylmethyl, adamantylmethyl), cycloalkenyl (e.g., cyclopropenyl), aryl (e.g., phenyl, naphthyl), arylalkyl (e.g., benzyl, phenethyl), heteroaryl (e.g., pyridyl, furyl), heteroarylalkyl (e.g., pyridylmethyl), heterocycle (e.g., piperidyl), heterocycle alkyl (e.g., morpholylmethyl), alkoxy (e.g., methoxy, ethoxy, propoxy, butoxy), alkyloxy halide (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino (e.g., alkylamino (e.g., methylamino, ethylamino, dimethylamino), acylamino (e.g., acetylamino, benzoylamino), arylalkylamino (e.g., benzylamino, tritylamino), hydroxyamino), alkylaminoalkyl (e.g., diethylaminomethyl), sulfamoyl, and the like. They can be substituted by 1-4 of these substituents. Alternatively, they may be substituted by one or more groups selected from lower alkyls and substituent group α.

The above-defined groups may also include a prefix and/or suffix which is generally used in the art for producing a sufficiently recognized substituent. As an example, "alkyloxy" or "alkoxy" refers to a group of the formula —OR", "alkylamine" refers to a group of the formula —NHR", "dialkylamine" refers to a group of the formula —NR"R", wherein each R" is independently an alkyl. As another example, "haloalkoxy" or "haloalkyloxy" refers to a group of the formula —OR'", wherein R'" is a haloalkyl.

In the present specification, "solvate" means a solvate of a compound of the present invention or a pharmaceutically acceptable salt thereof and includes, for example, a solvate with an organic solvent (e.g., alcoholate (e.g., ethanolate)), hydrate, and the like. When a hydrate is formed, it may be coordinated with an arbitrary number of water molecules. Examples of hydrates include monohydrate, dihydrate, and the like.

In the present specification, "prodrug" refers to a substance which is modified so that it does not exhibit drug action or only exhibits very weak activity as it is, but exhibits pharmacological activity for the first time or increases in pharmacological activity by being metabolized in vivo, taking advantage of the metabolism mechanisms of the body. Any form known in the art can be adopted as a pharmaceutically acceptable prodrug of the present invention. Examples of prodrugs include esters and amides, in addition to salts and solvates.

In the present specification, the terms "pharmaceutically acceptable salt, ester, amide, and prodrug" when used in this specification refer to a carboxylate, amino acid addition salt, ester, amide, and prodrug of a compound of the present specification. This refers to a substance which is within the normal scope of medical judgment, is suitable for use in contact with the tissues of a patient without excessive toxicity, inflammation, allergic response, or the like, and is effective for the intended use of the compound of the present invention.

When a compound of the present invention, solvate of the compound, pharmaceutically acceptable salt of the compound, or solvate of the salt form a prodrug, such various prodrugs are also encompassed by the present invention. A prodrug is a derivative of a compound of the present invention having groups that can be chemically or metabolically decomposed. It is a compound that becomes a pharmaceutically active compound of the present invention through solvolysis or under physiological conditions in vivo. Prodrugs include compounds converted into a compound of the present invention through enzymatic oxidation, reduction, hydrolysis, or the like under physiological conditions in the body, compounds converted into a compound of the present invention by hydrolysis by gastric juice, and the like. Methods for selecting suitable prodrug derivatives and methods of production are described, for example, in Design of Prodrugs, Elsevier, Amsterdam, 1985. Prodrugs themselves sometimes possess activity.

When a compound of the present invention, solvate of the compound, pharmaceutically acceptable salt of the compound, or solvate of the salt has a hydroxyl group, examples of prodrugs include acyloxy derivatives and sulfonyloxy derivatives produced, for example, by reacting the compound having a hydroxyl group with a suitable acyl halide, suitable acid anhydride, suitable sulfonyl chloride, suitable sulfonyl anhydride, or mixed anhydride or by reacting using a condensing agent. Examples include $CH_3COO-$, $C_2H_5COO-$, t-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3$—O-$PhSO_3-$, $PhSO_3-$, and p-$CH_3PhSO_3-$.

In the present specification, the term "salt" includes relatively non-toxic inorganic or organic acid addition salts or base addition salts of a compound of the present invention. These salts can be prepared by separately reacting a compound purified temporarily during the final isolation and purification of the compound or in the form of a free base with a suitable organic or inorganic acid and separating the salt formed in this way. Alternatively, they can be prepared by separately reacting a compound purified temporarily during the final isolation and purification of the compound or in the form of a free acid with a suitable organic or inorganic base and separating the salt formed in this way.

The following salts can be given as examples of pharmaceutically acceptable salts of compounds of the present invention.

Examples of pharmaceutically acceptable basic salts of compounds of the present invention include a sodium, salt, potassium salt, and other such alkali metal salts; calcium salt, magnesium salt, and other such alkaline earth metal salts; ammonium salt; trimethylamine salt, triethylamine salt, dicyclohexylamine salt, ethanolamine salt, diethanolamine salt, triethanolamine salt, procaine salt, meglumine salt, diethanolamine salt, ethylenediamine salt, and other such aliphatic amine salts; N,N-dibenzylethylenediamine salt, benethamine salt, and other such aralkylamine salts; pyridine salt, picoline salt, quinolone salt, isoquinoline salt, and other such heterocyclic aromatic amine salts; tetramethylammonium salt, tetraethylammonium salt, benzyltrimethylammonium salt, benzyltriethylammonium salt, benzyltributylammonium salt, methyltrioctylammonium salt, tetrabutylammonium salt, and other such quaternary ammonium salts; arginine salt, lysine salt, and other such basic amino acid salts; and the like.

Examples of pharmaceutically acceptable acidic salts of compounds of the present invention include a hydrochloride, sulfate, nitrate, phosphate, carbonate, bicarbonate, perchlorate, and other such inorganic acid salts; acetate, propionate, lactate, maleate, fumarate, tartrate, malate, citrate, ascorbate, and other such organic acid salts; methanesulfonate, isethionate, benzenesulfonate, p-toluenesulfonate, and other such sulfonates; aspartate, glutamate, and other such acidic amino acid salts; and the like.

A hydrochloride, phosphate, tartrate, methanesulfonate, and the like are especially preferred. These salts can be formed by the usual methods.

In the present specification, the term "pharmaceutically acceptable ester" refers to a relatively non-toxic product of esterification of a compound of the present invention. These esters can be prepared by separately reacting a compound purified in situ during the final isolation and purification of a compound or in the form of a free acid or a hydroxyl derivative with a suitable esterification agent. Carboxylates can be converted into esters through treatment with an alcohol in the presence of a catalyst. This term is also intended to include lower hydrocarbon groups that can be solvolyzed under physiological conditions, for example, alkyl esters, methyl esters, ethyl esters, and propyl esters.

In the present specification, "isomer" is used in the same meaning as that generally used in the art and refers to substances which have the same molecular formula, but are different in structural formula and nature. The isomers used in the present invention are not limited to particular isomers, but include all possible isomers (e.g., keto-enol isomers, imine-enamine isomers, diastereoisomers, optical isomers, diastereomers, geometric isomers, steric isomers, cis-trans isomers, configurational isomers, rotamers, and the like) and racemates. It is understood that one or more chiral centers are present in each of the compounds of the present invention. It is understood that the present invention includes all stereochemical forms of each compound, for example, enantiomers, diastereomers, and racemic compounds. When an asymmetric carbon atom is present, more than one steric isomer is possible, and it is intended that all possible isomers are included in the expression of an indicated structure. Optionally, active (R) and (S) isomers may be separated using conventional techniques known to a person skilled in the art. It is intended that the present invention includes possible diastereomers as well as racemic compounds and optically resolved isomers.

Throughout the following description, it is understood that the intention is to include both the cis configuration and trans configuration when a particular double bond is shown. An exemplary chemical formula is provided with a particular configuration but, for the sake of completeness, the double bond can be changed. For the purpose of maintaining the simplicity of the specification, not all structural isomers are shown. However, this should not in fact be deemed a limitation. In addition, it is understood that when a synthesis scheme is provided, all cis/trans configuration isomers are also intended and are included within the scope of the synthesis method.

One or more hydrogen, carbon and/or other atoms of a compound of the present invention can be substituted by an isotope of the respective hydrogen, carbon and/or other atom. Examples of such isotopes include hydrogen, carbon, nitrogen, oxygen, phosphorus, sulfur, fluorine, iodine, and chlorine, such as the respective $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$. The compounds of the present invention also encompass compounds substituted by such isotopes. Compounds substituted by these isotopes are also useful as medicaments, and all radiolabeled forms of compounds of the present invention are included. "Radiolabeling methods" for producing these "radiolabeled forms" are also included in the present invention, and these forms are useful in research in metabolic and pharmacokinetic studies and binding assay and/or as diagnostic tools.

Radiolabeled forms of compounds of the present invention can be prepared in a manner well known in the art. For example, a tritium-labeled compound of the present invention can be prepared, for example, by introducing tritium into a specific compound of the present invention by a catalytic dehalogenation reaction using tritium. This method includes reacting a compound of the present invention with a suitable halogen-substituted precursor and tritium in the presence of a suitable catalyst, for example, Pd/C, with or without a base present. Refer to Isotopes in the Physical and Biomedical Sciences, Vol. 1, Labeled Compounds (Part A), Chapter 6 (1987) for other suitable methods for preparing tritium-labeled compounds. $^{14}$C-labeled compound can be prepared by using a raw material having $^{14}$C carbon.

Hydroxyls in compounds of the present invention can be protected by various protecting groups such as protecting groups known in the art (e.g., a trimethylsilyl group (TMS), methoxymethyl group (MOM), 2-tetrahydropyranyl group (THP), ethoxyethyl group (EE)), and the like.

In the present specification, a "protecting group" refers to a group of atoms which, when bound to a reactive functional group in a molecule, mask, decrease, or hamper the reactivity of the functional group. Typically, the protecting group may be selectively removed as desired during the process of synthesis. Examples of the protecting group can be seen in Greene and Wuts, Protective Groups in Organic Chemistry, 3$^{rd}$ edition, 1999, John Wiley & Sons, NY and in Harrison et al., Compendium of Synthetic Organic Methods, Vols. 1-8, 1971-1996, John Wiley & Sons, NY. Examples of representative nitrogen protecting groups include, but are not limited to, the following: formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl, allyloxycarbonyl, 9-fluorenylmethyloxycarbonyl ("FMOC"), nitro-veratryloxycarbonyl ("NVOC"), and the like. Examples of representative hydroxyl protecting groups include, but are not limited to, those in which a hydroxyl group has been acetylated (esterified) or alkylated, for example, benzyl ether and trityl ether, as well as alkyl ether, tetrahydropyranyl ether, trialkyl-silyl ether (e.g., a TMS group or a TIPS group), glycol ether (e.g., ethylene glycol and propylene glycol derivatives), and allyl ether.

A person skilled in the art can easily determine which protecting group can be useful for protecting a hydroxyl group. Standard methods are known in the art and are more completely described in references. For example, a suitable protecting group can be selected by a person skilled in the art and is described in Green and Wuts, "Protecting Groups in Organic Synthesis," John Wiley and Sons, Chapters 5 and 7, 1991, and this instruction is incorporated into the present specification by reference. Preferred protecting groups include methyl and ethyl ether, TMS or TIPS groups, acetic acid (ester) or propionic acid ester groups, and glycol ether, for example, ethylene glycol and propylene glycol derivatives.

For example, one or more hydroxyl groups are treated with a mild base, for example, triethylamine, in the presence of an acid chloride or silyl chloride, and a reaction between hydroxyl ions and halide cans be made easy. Alternatively, an alkyl halide is reacted with a hydroxyl ion (generated by a base such as lithium diisopropylamide), and formation of an ether can be facilitated.

Resolvins/protectins refer to the followings: 5S,12R,18R-trihydroxy-6Z,8E,10E,14Z, 16E-eicosapentaenoic acid: resolvin E1 a; 5S,18R-dihydroxy-6E,8Z,11Z,14Z,16E-eicosapentaenoic acid: resolvin E2; 7S,8,17R-trihydroxy-docosa-4Z,9E,11E,13Z,15E,19Z-hexaenoic acid: aspirin trigger-type resolvin D1; 7S,16,17R-trihydroxy-docosa-4Z,8E,10Z,12E,14E,19Z-hexaenoic acid: aspirin trigger-type resolvin D2; 4S,11,17R-trihydroxy-docosa-5,7E,9E,13Z,15E,19Z-hexaenoic acid: aspirin trigger-type resolvin D3; 4S,5,17R-trihydroxy-docosa-6E,8E,10Z,13Z,15E,19Z-hexaenoic acid: aspirin trigger-type resolvin D4; 7S,17R-DiHDHA7S,17R-dihydroxy-docosa-5Z,8E,10Z,13Z,15E,19Z-hexaenoic acid: aspirin trigger-type resolvin D5; 4S,17R-DiHOHA4S,17R-dihydroxy-docosa-5E,7Z,10Z,13Z,15E,19Z-hexaenoic acid: aspirin trigger-type resolvin D6; 10,17R-DiHOHA10,17R-dihydroxy-docosa-4Z,7Z,11,13,15,19Z-hexaenoic acid: aspirin trigger-type 10,17R-docosatriene; 7S,8,17S-TriHDHA7S,8,17S-trihydroxy-docosa-4Z, 9E,11E,13Z,15E,19Z-hexaenoic acid: resolvin D1a; 7S,16,17S-TriHDHA7S,16,17S-trihydroxy-docosa-4Z,8E,10Z,12E,14E,19Z-hexaenoic acid: Resolvin D2a; 4S,11,17S-TriHDHA4S,11,17S-trihydroxy-docosa-5,7E,9E,13Z,15E,19Z-hexaenoic acid: resolvin D3a; 4S,5,17S-TriHDHA4S,5,17S-trihydroxy-docosa-6E,8E,10Z,13Z,15E,19Z-hexaenoic acid: resolvin D4a; 7S,17S-DiHDHA7S,17S-dihydroxy-docosa-5Z,8E,10Z,13Z,15E,19Z-hexaenoic acid: resolvin D5; 4S,17S-DiHDHA4S,17S-dihydroxy-docosa-5E,7Z,10Z,14Z,16E,19Z-hexaenoic acid: resolvin D6a; 10,17S-DiHDHA10,17S-dihydroxy-docosa-4Z,7Z,11E, 13E,15Z,19Z-hexaenoic acid: 10,17S-docosatriene, neuroprotectin D1; 16,17S-dihydroxy-docosa-4Z,7Z,10Z,12E, 14E,19Z-hexaenoic acid: 16,17S-docosatriene; 16,17-epoxy-docosa-4Z,7Z,10Z,12E,14E,19Z-hexaenoic acid: 16,17-epoxy-docosatriene.

The compounds of the present invention are different from Resolvin or Protectin and are substances believed not to be previously known.

PREFERRED EMBODIMENTS

Preferred embodiments of the present invention are shown below. Embodiments provided below are provided for a better understanding of the present invention, and the scope of the present invention is not limited by the following descriptions. Therefore, it is apparent that a person skilled in the art can appropriately make modifications within the scope of the present invention, in view of the descriptions in the present specification.

(Compounds)

In one aspect, the present invention provides the following compounds.

A compound selected from

[Chemical Formula 55]

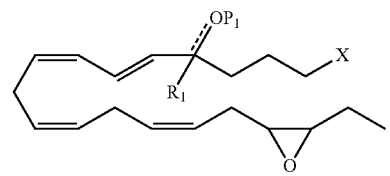

[Chemical Formula 56]

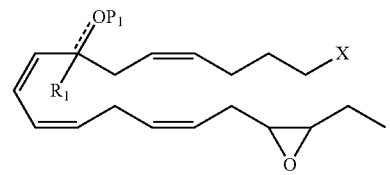

[Chemical Formula 57]
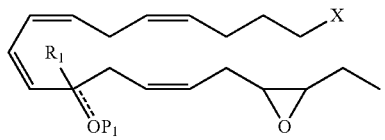

[Chemical Formula 58]
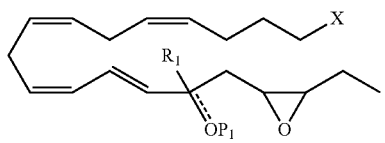

[Chemical Formula 59]
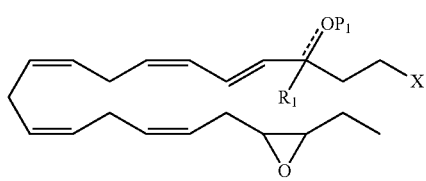

[Chemical Formula 60]
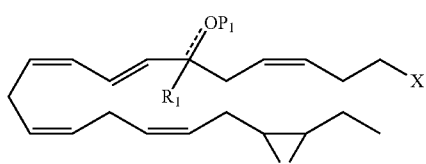

[Chemical Formula 61]
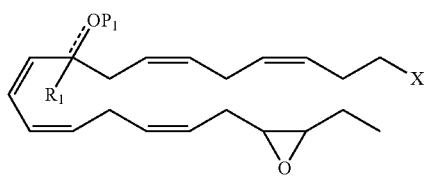

[Chemical Formula 62]
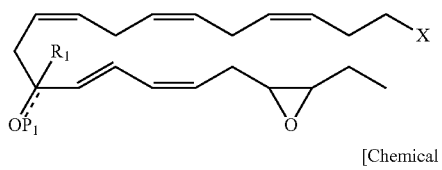

[Chemical Formula 63]
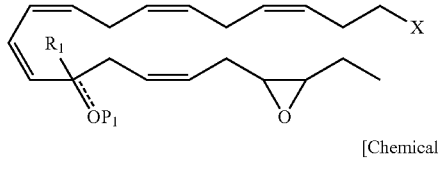

[Chemical Formula 64]
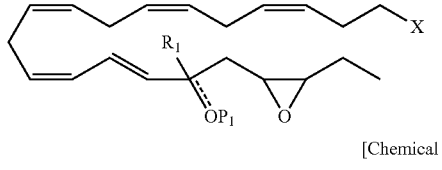

[Chemical Formula 65]
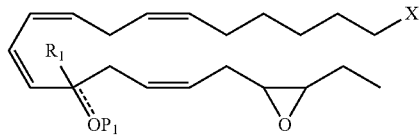

[Chemical Formula 66]
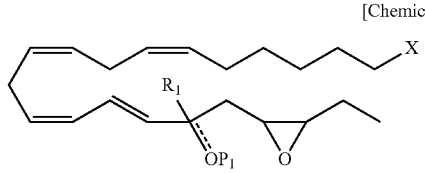 and

[Chemical Formula 67]
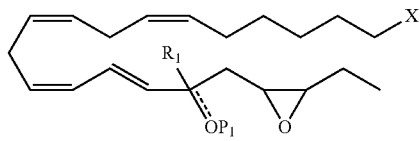

solvate of the compound, pharmaceutically acceptable salt of the compound, or solvate of the salt, wherein, when

[Chemical Formula 68]

----- shows a single bond, $P_1$ is a protecting group, hydrogen atom, alkyl, hydroxy group, or substituted hydroxy group, $R_1$ is a hydrogen atom, substituted or unsubstituted, branched or unbranched alkyl group, substituted or unsubstituted aryl group substituted or unsubstituted, branched or unbranched alkylaryl group, when

[Chemical Formula 69]

----- shows a double bond, $P_1$ and $R_1$ are not present;

X is —C(O)OR$_2$, —C(O)NR$_3$R$_4$, —C(O)H, —C(NH)NR$_3$R$_4$, —C(S)H, —C(S)OR$_2$, —C(S)NR$_3$R$_4$, —CN;

$R_2$ is a hydrogen, protecting group, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or formula: —NR$_a$R$_b$ (in the formula, R$_a$ and R$_b$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle or R$_a$ and R$_b$ together with adjacent nitrogen atoms may form a substituted or unsubstituted nitrogen-containing heterocycle);

$R_3$ and $R_4$ are each independently a hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted cycloalkenyl, substituted or unsubstituted heterocycle, or $R_3$ and $R_4$ together with adjacent nitrogen atoms may form a substituted or unsubstituted nitrogen-containing heterocycle;

and the double bond configuration of the compounds may be each independently either cis or trans.

These compounds are explained in greater detail below.

5-Hydroxy-17,18-epoxy-eicosatetraenoic acid (5hy-17,18-EpETE)-related compounds In one aspect, the present invention provides compounds and pharmaceutical compositions having the chemical formula:

[Chemical Formula 70]

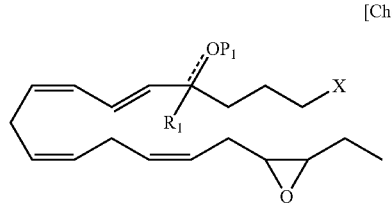

Wherein,

[Chemical Formula 71]

-----, $P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

8-Hydroxy-17,18-epoxy-ETE (8hy-17,18-EpETE)-related compounds

In one aspect, the present invention provides compounds and pharmaceutical compositions having the chemical formula:

[Chemical Formula 72]

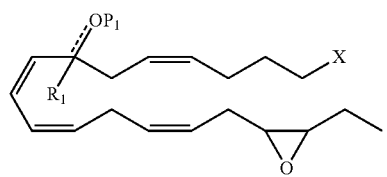

Wherein,

[Chemical Formula 73]

-----, $P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

12-Hydroxy-17,18-epoxy-ETE (12hy-17,18-EpETE)-related compounds

In one aspect, the present invention provides compounds and pharmaceutical compositions having the chemical formula:

[Chemical Formula 74]

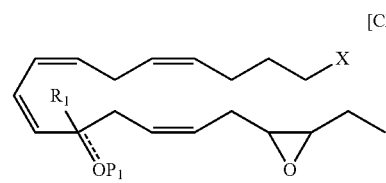

Wherein,

[Chemical Formula 75]

-----

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

15-Hydroxy-17,18-epoxy-ETE (15hy-17,18-EpETE)-related compounds

In one aspect, the present invention provides compounds and pharmaceutical compositions having the chemical formula:

[Chemical Formula 76]

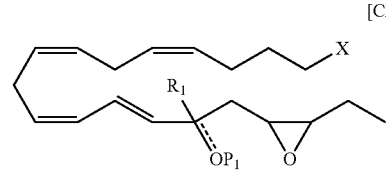

Wherein,

[Chemical Formula 77]

-----

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

4-Hydroxy-19,20-epoxy-DPE (4hy-19,20-EpDPE)-related compounds

In one aspect, the present invention provides compounds and pharmaceutical compositions having the chemical formula:

[Chemical Formula 78]

Wherein,

[Chemical Formula 79]

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

7-Hydroxy-19,20-epoxy-DPE (7hy-19,20-EpDPE)-related compounds

In one aspect, the present invention provides compounds and pharmaceutical compositions having the chemical formula:

[Chemical Formula 80]

Wherein,

[Chemical Formula 81]

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

10-Hydroxy-19,20-epoxy-DPE (10hy-19,20-EpDPE)-related compounds

In one aspect, the present invention provides compounds and pharmaceutical compositions having the chemical formula:

[Chemical Formula 82]

Wherein,

[Chemical Formula 83]

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

13-Hydroxy-19,20-epoxy-DPE (13hy-19,20-EpDPE)-related compounds

In one aspect, the present invention provides compounds and pharmaceutical compositions having the chemical formula:

[Chemical Formula 84]

Wherein,

[Chemical Formula 85]

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

14-Hydroxy-19,20-epoxy-DPE (14hy-19,20-EpDPE)-related compounds

In one aspect, the present invention provides compounds and pharmaceutical compositions having the chemical formula:

[Chemical Formula 86]

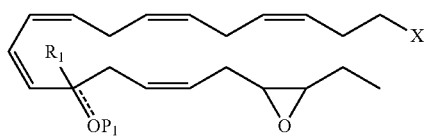

Wherein,

[Chemical Formula 87]

-----

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

17-Hydroxy-19,20-epoxy-DPE (17hy-19,20-EpDPE)-related compounds

In one aspect, the present invention provides compounds and pharmaceutical compositions having the chemical formula:

[Chemical Formula 88]

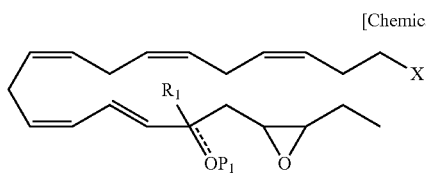

Wherein,

[Chemical Formula 89]

-----

$P_1$, $R_1$, and X are each independently as defined above.

17-Hydroxy-19,20-epoxy-DPE (17hy-19,20-EpDPE)-related compounds

In one aspect, the present invention provides compounds and pharmaceutical compositions having the chemical formula:

[Chemical Formula 90]

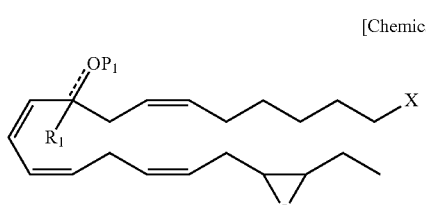

Wherein,

[Chemical Formula 91]

-----

$P_1$, $R_1$, and X are each independently as defined above.

In one aspect, the present invention provides compounds and pharmaceutical compositions having the chemical formula:

[Chemical Formula 92]

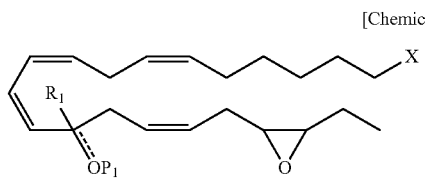

Wherein,

[Chemical Formula 93]

-----

$P_1$, $R_1$, and X are each independently as defined above.

In one aspect, the present invention provides compounds and pharmaceutical compositions having the chemical formula:

[Chemical Formula 94]

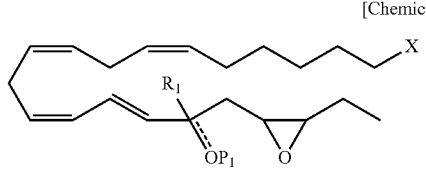

Wherein,

[Chemical Formula 95]

-----

$P_1$, $R_1$, and X are each independently as defined above.

In a specific embodiment, $P_1$ is a hydrogen atom, $R_1$ is a methyl group or hydrogen atom, and X is a carboxylic acid or carboxylic acid ester.

X can be a carboxylic acid, ester, amide, thiocarbamate, carbamate, thioester, thiocarboxamide, or nitrile. X is preferably a carboxylic acid, carboxylic acid ester, or pharmaceutically acceptable carboxylate.

These compounds are all epoxidated derivatives of eicosapentaenoic acid (EPA) and docosahexaenoic acid (DHA), which are PUFA of the ω3 series. They can be called a completely novel compound group insofar as they were not known in the past and belong to metabolites of a different series from the known metabolites called resolvins and protectins.

When $R_1$ and $P_1$ are hydrogen atoms and X is a carboxylic acid in a specific embodiment, the compound may be separated and/or purified. The purity of such compounds is at least 80%, especially at least approximately 90%, more specifically at least 95%, and more preferably at least approximately 99% based on analytical measurements using GC, MS, $^1$H-NMR, and the like. This applies to all separated compounds and/or purified compounds throughout this specification.

(Other Modified Forms of Compounds)

In another aspect, the present invention can be expressed as follows.

A compound selected from

[Chemical Formula 96]

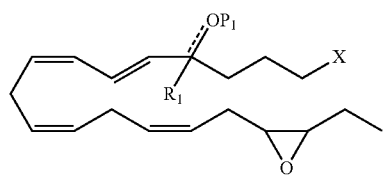

[Chemical Formula 97]

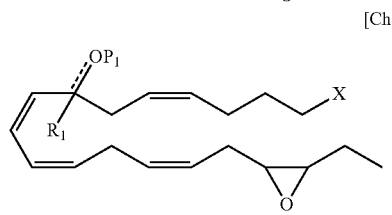

[Chemical Formula 98]

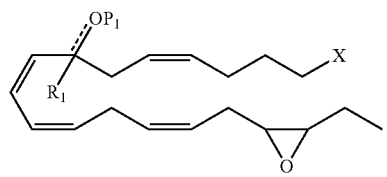

[Chemical Formula 99]

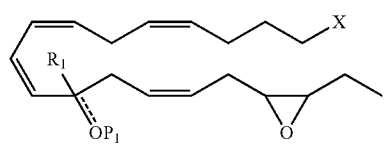

[Chemical Formula 100]

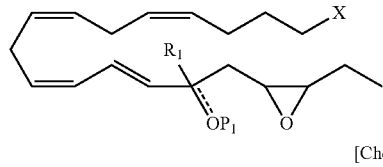

[Chemical Formula 101]

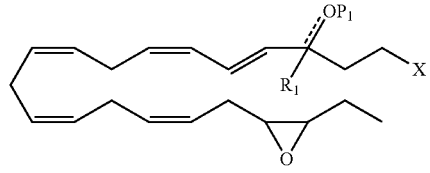

[Chemical Formula 102]

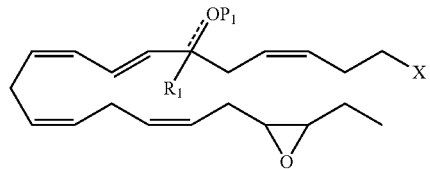

[Chemical Formula 103]

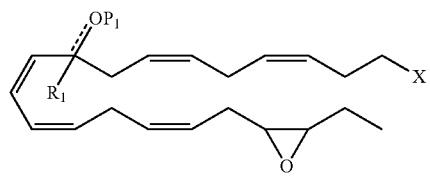

[Chemical Formula 104]

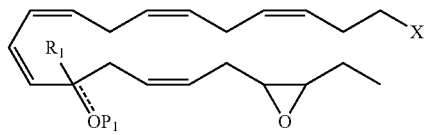

[Chemical Formula 105]

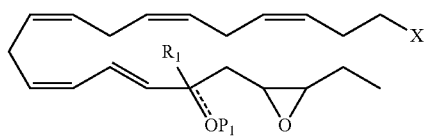

[Chemical Formula 106]

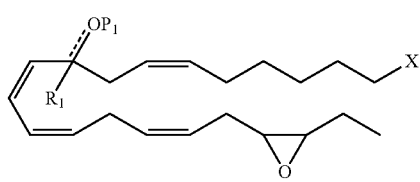

[Chemical Formula 107]

and

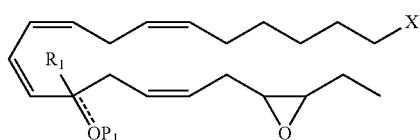

[Chemical Formula 108]

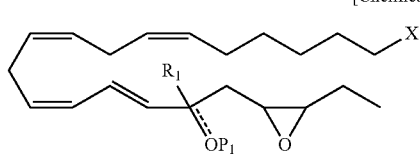

solvate of the compound, pharmaceutically acceptable salt of the compound, or solvate of the salt, in the formula, when

[Chemical Formula 109]

----- shows a single bond, $P_1$ is a protecting group, hydrogen atom, alkyl, hydroxy group, or substituted hydroxy group, $R_1$ is a hydrogen atom, substituted or unsubstituted, branched or unbranched alkyl group, substituted or unsubstituted aryl group (for example, including also a substituted or unsubstituted, branched or unbranched alkylaryl group), when

[Chemical Formula 110]

----- shows a double bond, $P_1$ and $R_1$ are not present;

X is —C(O)ORd, —C(O)NRcRc, —C(O)H, —C(NH)NRcRc, —C(S)H, —C(S)ORd, —C(S)NRcRc, —CN;

each Rc, when present, is independently a protecting group or Ra, or alternatively, each Rc may together with nitrogen atoms to which it binds form a 5- to 8-membered cycloheteroalkyl or heteroaryl, and these may optionally contain one or more of the same or different additional heteroatoms and may be optionally substituted by one or more of the same or different Ra groups or suitable Rb groups;

each Rd, when present, is independently a protecting group or Ra;

each Ra, when present, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2- to 6-membered heteroalkyl, 3- to 8-membered cycloheteroalkyl, morpholinyl, piperazinyl, homopiperazinyl, piperidinyl, 4- to 11-membered cycloheteroalkylalkyl, 5- to 10-membered heteroaryl, and 6- to 16-membered heteroarylalkyl;

each Rb, when present, is a suitable group independently selected from =O, —ORd, (C1-C3) haloalkyloxy, —OCF$_3$, =S, —SRd, =NRd, —NRcRc, halogen, —CF$_3$, —CN, —NC, —OCN, —SCN, —NO, —NO$_2$, =N$_2$, —N$_3$, —S(O)Rd, —S(O)$_2$Rd, —S(O)$_2$ORd, —S(O)NRcRc, —S(O)$_2$NRcRc, —OS(O)Rd, —OS(O)$_2$Rd, —OS(O)$_2$ORd, —OS(O)$_2$NRcRc, —C(O)Rd, —C(O)ORd, —C(O)NRcRc, —C(NH)NRcRc, —C(NRa)NRcRc, —C(NOH)Ra, —C(NOH)NRcRc, —OC(O)Rd, —OC(O)ORd, —OC(O)NRcRc, —OC(NH)NRcRc, —OC(NRa)NRcRc, —[NHC(O)]$_n$Rd, —[NRaC(O)]$_n$Rd, —[NHC(O)]$_n$ORd, —[NRaC(O)]$_n$ORd, —[NHC(O)]$_n$NRcRc, —[NRaC(O)]$_n$NRcRc, —[NHC(NH)]$_n$NRcRc, and —[NRaC(NRa)]$_n$NRcRc;

each n, when present, is independently an integer of 0-3.

In one embodiment, X is a carboxylic acid, ester, pharmaceutically acceptable carboxylate, or prodrug thereof.

In a specific embodiment, X is a pharmaceutically acceptable salt of a carboxylic acid, particularly an ammonium salt, or forms a prodrug.

In one embodiment, when C-4, C-5, C-6, C-7, C-8, C-10, C-12, C-13, C-14, C-15, C-16, C-17, C-18, C-19, C-20, and the like are present, as long as there is a chiral center, each independently may have an R configuration or S configuration or R/S configuration.

In certain embodiments, P$_1$, when present, is a hydrogen atom, and X is a carboxylic acid or ester.

In other embodiments, P$_1$ is present and is a hydrogen atom, and X is a carboxylic acid or ester.

In a specific embodiment, R$_1$, when present, is methyl, ethyl, propyl, or another such lower alkyl group and can be halogenated, such as trifluoromethyl. In one form, R$_1$, when present, is other than a hydrogen atom. X is generally a carboxylic acid, and P$_1$ is a hydrogen atom.

In a specific embodiment, P$_1$ is a hydrogen atom, and X is a carboxylic acid ester. In another embodiment, P$_1$ is a hydrogen atom, and X is a carboxylic acid. In another embodiment, P$_1$ is a hydrogen atom, and X is other than a carboxylic acid.

In one aspect, the compounds described in this specification are separated and/or purified. Compounds wherein P$_1$ is a hydrogen atom and X is a carboxylic acid in particular are separated and/or purified.

Compounds of the present invention are useful in the treatment of conditions that can be subjected to treatment, therapy, or prevention by suppressing neutrophils, for example, inflammatory diseases. Such utility is also present variously in other than inflammatory diseases as illustrated at other locations in the present specification.

Therefore, in a preferred embodiment, the present invention provides the following compounds, solvates of these compounds, pharmaceutically acceptable salts of these compounds, and solvates of these salts:

[Chemical Formula 111]

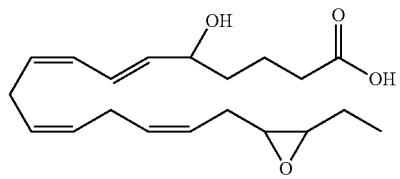

[Chemical Formula 112]

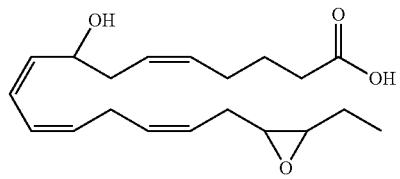

[Chemical Formula 113]

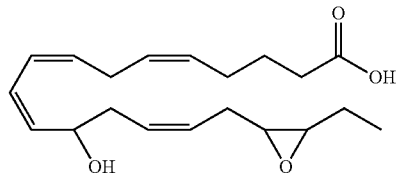

[Chemical Formula 114]

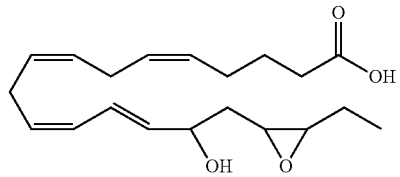

[Chemical Formula 115]

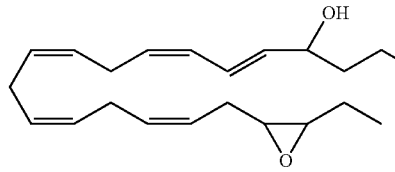

[Chemical Formula 116]

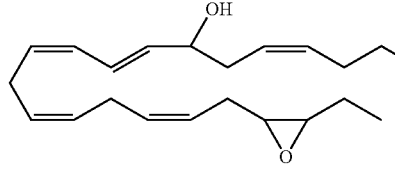

[Chemical Formula 117]

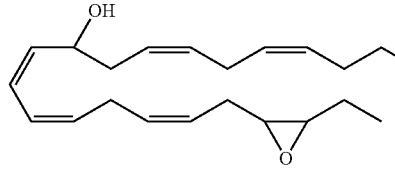

[Chemical Formula 118]

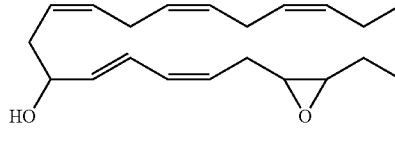

[Chemical Formula 119]

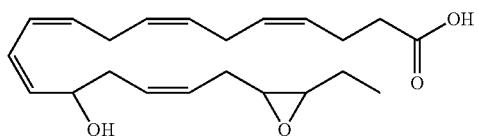

[Chemical Formula 120]

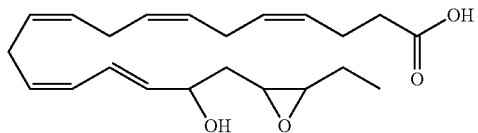

[Chemical Formula 121]

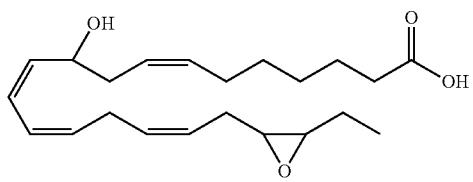

[Chemical Formula 122]

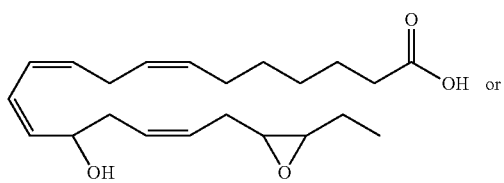

or

[Chemical Formula 123]

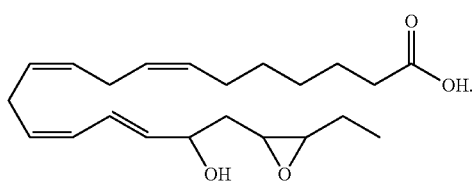

The compounds described in the present specification have anti-inflammatory activity as evidenced by down regulation of neutrophil infiltration in peritonitis models.

It is understood that "X" found in compounds of the present invention can be changed from one particular moiety to another moiety by a person skilled in the art. In order to attain this, in a certain specific example, one or more groups can require protection. This is also within the scope of a person skilled in the art. For example, a carboxylic acid ester can be converted into an amide by treatment using an amine. Such interconversion is known in the art.

It is understood that, in compounds of the present invention, reference to "hydroxy" stereochemistry is exemplary, and this term means to include protected hydroxy groups and free hydroxyls. In a specific embodiment, the C-17 position and the like have an R configuration. In another embodiment, the C-17 position and the like have an S configuration Compounds of the present invention can be protected by a variety of protecting groups such as those known in the art. A person skilled in the art can easily determine which protecting group can be useful for protecting a hydroxy group using procedures and the like described in Green and Wuts, "Protecting Groups in Organic Synthesis," John Wiley and Sons, Chapters 5 and 7, 1991, and the present specification.

It is understood that, regarding compounds of the present invention, not all hydroxy groups require protection. One or two all [sic] hydroxy groups can be protected. This can be attained by stoichiometric selection of reagents used for protecting hydroxy groups, using procedures described in Green and Wuts, "Protecting Groups in Organic Synthesis", John Wiley and Sons, Chapters 5 and 7, 1991 and other such known references and elsewhere in the present specification. The methods known in the art, for example, high-performance liquid chromatography (HPLC), liquid chromatography (LC), flash chromatography, gel permeation chromatography, crystallization, distillation, and the like can be used for separating a mono-protected or di-protected hydroxy compound.

It is understood that each of the above-identified compounds can take the form of a variety of isomers. Particularly, it is understood that one or more chiral centers are present in the compounds of the present invention. It is understood that the present invention includes all stereochemical types of each compound, for example, enantiomers, diastereomers, and racemic compounds. When an asymmetric carbon atom is present, more than one steric isomer is possible, and it is intended that all possible isomer types are included in the expression of an indicated structure. Optionally, optically active (R) and (S) isomers may be separated using conventional techniques known to a person skilled in the art. It is intended that the present invention includes possible diastereomers as well as racemic compounds and optically resolved isomers.

Compounds of the present invention contain an acetylenic and/or ethylenic unsaturated site. When a carbon-carbon double bond is present, the steric configuration chemistry can be either cis (E) or trans (Z), and expression throughout the present specification does not mean limitation. The expression is generally presented based on the steric configuration chemistry of a related DHA or EPA compound, and is thought to have the same steric configuration chemistry without being limited by theory. Throughout the present specification, carbon-carbon bonds are simplified, particularly in order to show the manner in which the bonds are finally arranged relative to each other. For example, the acetylene moiety of resolvin is known to actually contain geometry of approximately 180°, but it is understood that extreme expressions of such angles are used to assist in understanding in compounds of the present invention as well in order to assist in understanding synthesis and the relationship between the final product and the starting substance.

It is understood that the present invention also encompasses compounds which can generate one or more kinds of products by hydrogenation of the acetylene moiety. It is intended that all possible products are included in the present specification. For example, hydrogenation of a diacetylenic compound of the present invention can produce up to eight kinds of products (when hydrogenation of both acetylene moieties is complete (this can be monitored by a known method), four kinds of diene products, that is, cis, cis; cis, trans; trans, cis; trans, trans) and four kinds of monoacetylene-monoacetylene products (cis or trans "monoene"-acetylene; acetylene-cis or trans "monoene"). All the products can be separated and identified by high-performance liquid chromatography (HPLC), gas chromatography (GC), mass spectrometry (MS), nuclear magnetic resonance (NMR), infrared analysis (IR), and the like.

Techniques known in the art can be used for converting the carboxylic acid/ester functional group of a compound of the present invention into a carboxamide, thioester, nitrile, carbamate, thiocarbamate, or the like, and are incorporated in the present specification. An amide or other suitable moiety can be further substituted as known in the art.

(Production of Compounds of the Present Invention)

Compounds of the present invention can be synthesized by common organic chemistry procedures or produced by causing 5-lipoxygenase (5-LOX), 8-lipoxygenase (8-LOX), 12-lipoxygenase (12-LOX), 12/15-lipoxygenase (12/15-LOX), soybean lipoxygenase (sLOX), or another such enzyme to act on 17,18-epoxyeicosatetraenoic acid (17,18-epoxy-ETE), 19,20-epoxydocosapentaenoic acid (19,20-epoxy-DPE), or 19,20-epoxydocosatetraenoic acid (19,20-epoxy-DTE), which are substances known as precursors, or by causing an ω3 epoxidase (e.g., Cyp450BM3 or the like) to act on relatively abundant 5-hydroxyeicosapentaenoic acid (5-HEPE), 8-hydroxyeicosapentaenoic acid (8-HEPE), 12-hydroxyeicosapentaenoic acid (12-HEPE), 15-hydroxyeicosapentaenoic acid (15-HEPE), 4-hydroxydocosahexaenoic acid (4-HDoHE), 7-hydroxydocosahexaenoic acid (7-HDoHE), 10-hydroxydocosahexaenoic acid (10-HDoHE), 13-hydroxydocosahexaenoic acid (13-HDoHE), 14-hydroxydocosahexaenoic acid (14-HDoHE), 17-hydroxydocosahexaenoic acid (17-HDoHE), 10-hydroxydocosapentaenoic acid (10-HDoPE), 14-hydroxydocosapentaenoic acid (14-HDoPE), and 17-hydroxydocosapentaenoic acid (17-HDoPE), or another such monohydroxy compound.

"ω3 Epoxidase" in the present specification means an arbitrary enzyme capable of epoxidating the ω3 position of an unsaturated fatty acid. Examples include Cyp450BM3 (e.g., refer to Capdevila J H, Wei S, Helvig C, Falck J R, Belosludtsev Y, Truan G, Graham-Lorence S E, Peterson J A. J Biol Chem. 1996 Sep. 13; 271(37): 22663-71) and the like.

Therefore, the present invention provides a method for producing a compound of the present invention, solvate of the compound, pharmaceutically acceptable salt of the compound, or solvate of the salt. This method includes A) a step for obtaining an enzymatic metabolite by contacting at least one selected from the group consisting of 5-lipoxygenase (5-LOX), 8-lipoxygenase (8-LOX), 12-lipoxygenase (12-LOX), 12/15-lipoxygenase (12/15-LOX), and soybean lipoxygenase (sLOX) with 17,18-epoxyeicosatetraenoic acid (17,18-epoxy-ETE), 19,20-epoxydocosapentaenoic acid (19,20-epoxy-DPE), or 19,20-epoxydocosatetraenoic acid (19,20-epoxy-DTE); and B) a step for reducing or oxidizing the enzymatic metabolite as needed, introducing a substituent as needed, and separating or purifying the target compound, solvate of the compound, pharmaceutically acceptable salt of the compound, or solvate of the salt as needed. A hydroxy compound is produced upon reduction when making a peroxide (perhydroxy compound). The corresponding ketone compound is produced by further oxidation thereof. All of these have possibilities as bioactive substances. These enzymes can be utilized by the following known techniques. 5-Lipoxygenase (5-LOX): Reddanna P, Whelan J, Maddipati K R, Reddy C C. Methods Enzymol. 1990; 187: 268-77, mouse recombinant 8-LOX: Jisaka M. et al. J Biol Chem, 272, 24410-24416 (1997); platelet 12-LOX: Yoshimoto T. et al. Prostaglandins and Other Lipid Mediators Vol. 68-69, 245-262 (2002); leukocyte 12/15-LOX: Kuhn H et al. Prostaglandins and Other Lipid Mediators Vol. 68-69, 263-290 (2002); sLOX: Oliw E. H. Prostaglandins and Other Lipid Mediators Vol. 68-69, 313-324 (2002). The lipoxygenase (LOX), cyclooxygenase (COX), cytochrome P450 (CYP) enzymes given as examples in Patent Reference 1 and other heme-containing enzymes can also be used in the present invention. It is understood that the methods described in the present specification for purification used here are examples; for example, HPLC or the like can be given as an example but is not limited to this, and the degrees of separation and purification can also be adjusted as is appropriate.

For example, a compound of the present invention can be obtained by hydroxylating 17,18-epoxy-ETE, 19,20-epoxy-DPE, or 19,20-epoxy-DTE, or another such epoxy compound by reaction with 12-LOX, reducing or oxidizing the reaction product obtained as needed, introducing a substituent as needed, and separating or purifying the target compound, solvate of the compound, pharmaceutically acceptable salt of the compound, or solvate of the salt as needed, as an exemplary method.

Alternatively, a compound of the present invention can be obtained by hydroxylating 17,18-epoxy-ETE, 19,20-epoxy-DPE, or 19,20-epoxy-DTE, or another such epoxy compound by reaction with sLOX, reducing or oxidizing the reaction product obtained as needed, introducing a substituent as needed, and separating or purifying the target compound, solvate of the compound, pharmaceutically acceptable salt of the compound, or solvate of the salt as needed.

Alternatively, a compound of the present invention can also be synthesized by first synthesizing a hydroxy compound and epoxidating it. As a synthesis example, a compound of the present invention can be obtained by using various HEPE, HDoHE, or HDoPE as the starting material, epoxidating these materials by P450 BM3 or another such epoxidase, reducing or oxidizing the reaction product obtained as needed, introducing a substituent as needed, and separating or purifying the target compound, solvate of the compound, pharmaceutically acceptable salt of the compound, or solvate of the salt as needed. Such examples are given as examples in the working examples, and a person skilled in the art can synthesize compounds of the present invention as is appropriate based on these examples.

As was mentioned above, compounds of the present invention can be produced via chemical synthesis using a longchain polyunsaturated fatty acid (LCPUFA) precursor or can be synthesized completely afresh. Methods of chemical synthesis of oxylipin compounds are known in the art (e.g., refer to Rodriguez and Spur (2004); Rodriguez and Spur, 2005; Guilford et al. (2004)). Methods of common chemical synthesis are also known in the art. For example, compounds of the present invention can be prepared by both conventional synthesis techniques and solid-phase synthesis techniques known to persons skilled in the art. Useful conventional techniques include techniques disclosed in U.S. Pat. Nos. 5,569,769, 5,242,940, and PCT Publication WO96/37476, and these are all incorporated in the present specification as references. Combinatorial techniques can also be particularly useful in the synthesis of compounds of the present invention. For example, reference can be made to Brown, Contemporary Organic Synthesis, 1997, 216; Felder and Poppinger, Adv. Drug Res., 1997, 30, 111; Balkenhohl et al., Angew. Chem. Int. Ed. Engl., 1996, 35, 2288; Hermkens et al., Tetrahedron, 1996, 52, 4527; Hermkens et al., Tetrahedron, 1997, 53, 5643; Thompson et al., Chem. Rev., 1996, 96, 555; and Nefzi et al., Chem. Rev., 1997, 2, 449-472.

Compounds of the present invention can be produced using the following compounds (specifically, EPA, DHA, DPA, and epoxidated compounds thereof):

[Chemical Formula 124]

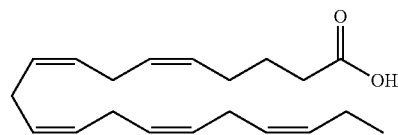

[Chemical Formula 125]
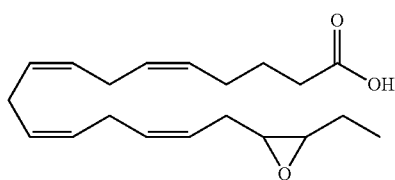

[Chemical Formula 126]
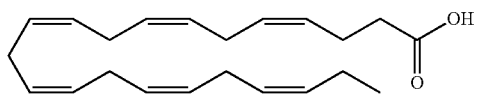

[Chemical Formula 127]
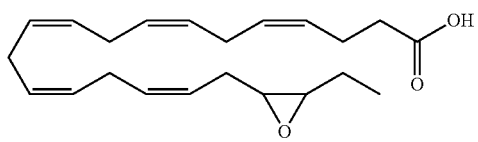

[Chemical Formula 128]
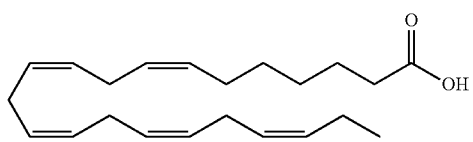

[Chemical Formula 129]
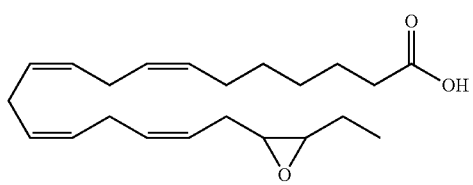

[Chemical Formula 130]
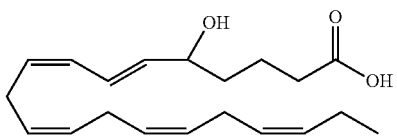

[Chemical Formula 131]
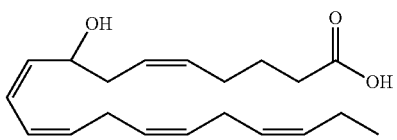

[Chemical Formula 132]
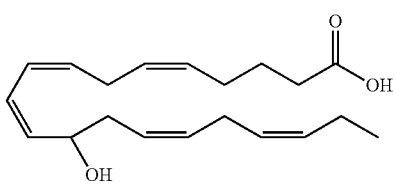

[Chemical Formula 133]
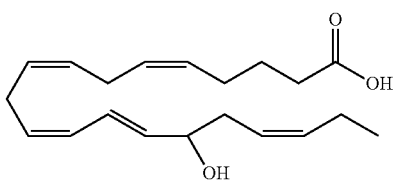

[Chemical Formula 134]
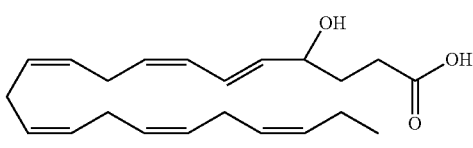

[Chemical Formula 135]
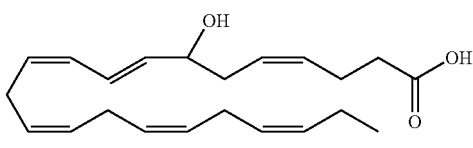

[Chemical Formula 136]
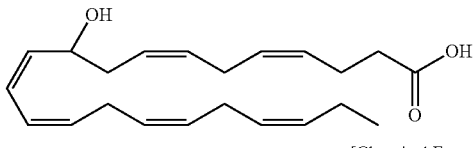

[Chemical Formula 137]
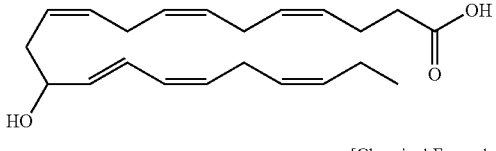

[Chemical Formula 138]
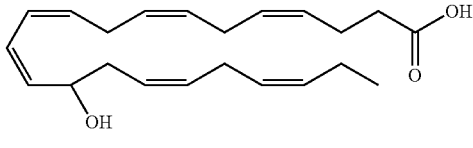

as raw materials by using the above techniques and other known techniques.

Since EPA, DHA, and DPA are present in abundance in the body, they can also be extracted from foods and the like or commercial products may be purchased. In this regard, commercial products (available from Cayman Inc.) can be used for 17,18-epoxy-ETE or 19,20-epoxy-DPE, or they can be produced using the following methods. 17,18-epoxy-ETE, 19,20-epoxy-DPE, and 19,20-epoxy-DTE are all metabolites in which only the ω3 part of a ω3 PUFA has been epoxidated.

Examples of enzymes that can be used in the production process of the present invention include 5-lipoxygenase (e.g., potato 5-lipoxygenase (5-LOX)), 8-lipoxygenase (e.g., mouse recombinant 8-lipoxygenase (8-LOX)), 12-lipoxygenase (12-LOX) (e.g., platelet 12-LOX), 12/15-lipoxygenase (12/15-LOX) (e.g., leukocyte 12/15-LOX), soybean lipoxygenase (sLOX), and the like. It is understood that suitable enzymes can be used as is appropriate while taking into consideration their substrate specificity.

For the precursor materials shown below (e.g., hydroxy compounds described in the present specification and the like), commercial products (available from Cayman Inc.) can be used for those of the EPA and DHA series or even those of the DPA series that are not available commercially can be obtained by enzymatic synthesis, chemical synthesis, or extraction from living organisms. For example, for those of the DPA series, the corresponding hydroxy compounds can be produced by adding and reacting 8-LOX, 12-LOX, or sLOX with n-3 DPA.

-continued

[Chemical Formula 139]

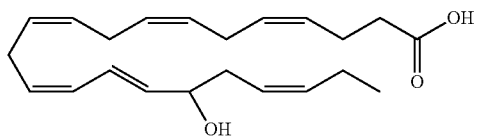

[Chemical Formula 140]

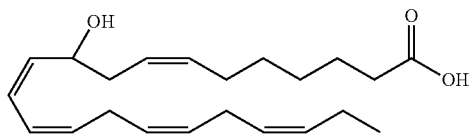

[Chemical Formula 141]

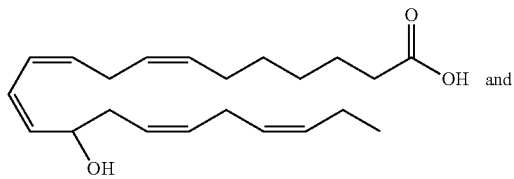

and

[Chemical Formula 142]

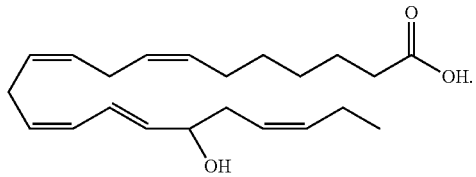

The method or technique of purification, separation, or isolation used in the present specification, when necessary, includes column chromatography, high performance liquid chromatography (HPLC), gas chromatography (GC), crystallization, and distillation. Characterization can be performed by ultraviolet (UV) analysis, mass analysis (MS), MS/MS, GC/MS, nuclear magnetic resonance (NMR), or the like. A person skilled in the art can utilize various methods for preparing, separating, and characterizing these novel compounds, based on the instructions of the present specification.

When $P_1$ is other than hydrogen, for example, a protecting group, alkyl, hydroxy group, or substituted hydroxy group, it is understood that compounds of the present invention can be produced using techniques known in the art by enzymatic reaction after introducing these substituents into a precursor or by introducing substituents after producing each compound in which it is hydrogen by methods described in the present specification or a combination of these methods. Derivative production techniques known for resolvins and protectins can be applied as such techniques.

For example, compounds in which $P_1$ is other than hydrogen can be produced by producing compounds in which $P_1$ is hydrogen and then substituting the hydroxyls of these compounds by alkyl groups or various protecting groups (e.g., those known in the art). A person skilled in the art can easily decide which protecting groups can be useful in the protection of these hydroxy groups. Standard methods are known in the art and adequately described in the literature. For example, substitution by alkyl groups and substitution by suitable protecting groups can be performed and selected easily by one skilled in the art, and the contents described by Greene and Wuts in "Protecting Groups in Organic Synthesis," John Wiley and Sons, Chapters 5 and 7, 1991 (these instructions are incorporated as a reference in the present specification) can be considered. Preferred protecting groups include methyl and ethyl esters, TMS and TIPS groups, acetic acid esters or propionic acid esters, and glycol ethers (e.g., ethylene glycol and propylene glycol derivatives). Derivative production techniques known for resolvins and protectins can be applied as such techniques.

Alternatively, when $P_1$ is a hydroxy group or substituted hydroxy group, that is, for a peroxide, a compound obtained by an enzymatic reaction may be separated or, in the case of a substituted hydroxy group, the peroxide may be further substituted by alkyl groups, protecting groups, and other such substituents using the above known techniques. Derivative production techniques known for resolvins and protectins can be applied as such techniques.

When $R_1$ is other than hydrogen, for example, a halogen atom, substituted or unsubstituted, branched or unbranched alkyl group, substituted or unsubstituted aryl group, substituted or unsubstituted, branched or unbranched alkylaryl group, it is understood that compounds of the present invention can be produced using techniques known in the art by enzymatic reaction after introducing these substituents into a precursor or by introducing substituents after producing each compound in which it is hydrogen by methods described in the present specification or a combination of these methods. Derivative production techniques known for resolvins and protectins can be applied as such techniques.

In this regard, the use of "R protection chemistry" is not necessarily required for adjacent diols among compounds of the present invention when $R_1$ is other than hydrogen. Typically, adjacent diols are not oxidized easily and, furthermore, do not require such protection by substitution of the hydrogen atoms adjacent to the oxygen atoms of the hydroxy group. Therefore, such protection is generally regarded as unnecessary. However, it is also possible to prepare compounds in which the hydroxy groups of the adjacent diols "can be protected" independently by substituting the hydrogen atoms adjacent to the oxygen atoms of the hydroxy groups using the abovementioned substituents as protecting groups. Derivative production techniques known for resolvins and protectins can be applied as such techniques.

For introducing such $R_1$ groups, for example, a hydroxy group is oxidized by Pfitzner-Moffatt oxidation, Swern oxidation, Jones oxidation, or the like, to obtain a ketone, and a substituent such as alkyl, aryl, alkylaryl, or the like can be introduced into $R_1$ together with reduction into an alcohol, by Grignard reaction, Barbier coupling reaction, Kagan-Molander reaction in the presence of diiodosamarium, or the like and, if necessary, $P_1$ and the like can be further introduced. Derivative production techniques known for resolvins and protectins can be applied as such techniques.

The following synthesis route illustrates a method of preparing the target compounds of the present invention. The preparation product does not intend limitation, but works as another means for preparing the compounds of the present along more traditional lines, and should be regarded as a complement to biosynthesis.

Compounds of the present invention can be also synthesized by an organic synthesis method.

(Bioactivity, Medicine and Drug, Treatment, Prevention, and Therapy Methods, and Use in Production of a Drug)

In one aspect, the present invention provides a neutrophil suppressant comprising a compound of the present invention, solvate of the compound, pharmaceutically acceptable salt of the compound, or solvate of the salt.

Alternatively, in another aspect, the present invention is a method for the treatment, therapy, or prevention of inflammatory diseases and provides a method that includes a step for administering a compound of the present invention, solvate of the compound, pharmaceutically acceptable salt of the compound, or solvate of the salt to a subject in need of the such treatment, therapy, or prevention.

In yet another aspect, the present invention is a method for the treatment, therapy, or prevention of inflammatory diseases relating to the use of a compound of the present invention, solvate of the compound, pharmaceutically acceptable salt of the compound, or solvate of the salt for producing a medicament.

In yet another aspect, it relates to the use of a compound of the present invention, solvate of the compound, pharmaceutically acceptable salt of the compound, or solvate of the salt for producing a medicament for the treatment, therapy, or prevention of conditions, disorders, or states related to neutrophils.

These drugs, medicines (neutrophil suppressants and the like), treatment methods, therapeutic methods, prevention methods, and production of a medicament for treatment, therapy, or prevention have the following embodiments. They are described in order below.

Therefore, the present invention can prevent the infiltration into tissues and the activation of neutrophils, for example, at the time of acute inflammation. Such preventative capacity is useful in preventing the infiltration into tissues and activation of neutrophils found in ischemic reperfusion injury, stroke, myocardial infarction, acute nephritis, and the like. Therefore, since infiltration into tissues and activation of neutrophils are strongly suppressed by a very low dose, it is understood that the present invention is useful as one having an effect as a therapeutic. In rheumatoid arthritis, inflammatory colitis, asthma, and other such chronic inflammatory diseases as well, compounds of the present invention are expected to have beneficial and therapeutic effects with few adverse effects in medium- and long-term administration since they have been judged to be endogenous substances also present inherently in the body.

In the present specification, "disease, disorder, or symptom associated with neutrophils" refers to a disease, disorder, or symptom which is improved by inhibiting neutrophils. Such disease states or symptoms are described throughout the present specification, and all of them are incorporated in the present specification. Currently unknown states associated with neutrophil regulation, which may be found in the future, are also encompassed by the present invention, because characterization as a state associated with neutrophil regulation can be easily determined by a person skilled in the art.

In one embodiment, the present invention also relates to methods for the treatment, therapy, alleviation, and cure of disease states or symptoms relating to inflammation.

Conditions targeted by the present invention include the following. Many gastrointestinal inflammatory disorders of the digestive system (mouth, stomach, esophagus, small intestine, and large intestine), for example, stomatitis, periodontal disease, esophagitis, gastritis, ulcerative colitis, Crohn's disease, and other such inflammatory intestinal conditions, infectious enteritis (viral, bacterial, parasitic), antibiotic-associated diarrhea, *Clostridium difficile* colitis, microscopic or lymphocytic colitis, collagenous colitis, colon polyps and familial polyp syndromes (e.g., familial polyposis syndrome, Gardner's syndrome), *Helicobacter pylori*, irritable bowel syndrome, non-specific diarrhea, and colon cancer; inflammatory bowel disease (IBD), colitis which is induced by stimulation from the outside world (e.g., inflammation of the stomach and intestine (e.g., colitis) caused by therapeutic regimens such as administration of chemotherapy and radiation therapy, or is associated therewith (e.g., as an adverse effect)), chronic granulomatous disease, celiac disease, celiac sprue (genetic disease in which the back layer of the intestine becomes inflamed in response to ingestion of a protein known as gluten), food allergy, gastritis, infectious gastritis, or enterocolitis (e.g., *Helicobacter pylori* infectious chronic active gastritis) and other types of gastrointestinal inflammation caused by an infectious factor; pulmonary distress syndrome, adult respiratory distress syndrome, chronic obstructive pulmonary disease (COPD), and other such lung diseases; ischemic heart disease, ischemic kidney disease, ischemic brain disease, ischemic liver disease, and other such ischemic diseases; stress-related conditions such as erosive gastritis, gastric ulcer, duodenal ulcer, bronchial asthma, ulcerative colitis, arteriosclerosis, Crohn's disease, malignant tumor, ovarian cyst, salpingitis, uterine myoma, endometriosis, spontaneous abortion, toxemia of pregnancy, infertility, and dysmenorrhea.

Acute and chronic inflammatory states are encompassed within inflammation. Acute inflammation is generally characterized by onset within a short time and the infiltration or influx of neutrophils. Chronic inflammation is generally characterized by onset over a relatively long period of time (e.g., several days, several weeks, several months, or several years, and up to the lifespan of the subject) and infiltration or influx of mononuclear cells. Chronic inflammation can also typically be characterized by periods of spontaneous recovery and spontaneous onset.

In one aspect, the present invention provides a drug comprising a compound of the present invention, solvate of the compound, pharmaceutically acceptable salt of the compound.

A compound of the present invention, solvate of the compound, pharmaceutically acceptable salt of the compound, or solvate of the salt can also be administered alone, but it is usually preferable to provide it as various types pharmaceutical formulations. These pharmaceutical formulations can also be used in animals and humans.

The route of administration is preferably the one most effective for treatment, therapy, prevention, or the like. Preferred examples include oral and rectal, vaginal, nasal, intraoral, sublingual, percutaneous, subcutaneous, intramuscular, intravenous, and other such parenteral routes. The amount of active ingredient that can be combined with a carrier material to produce a single dosage form is generally the amount of compound that produces a therapeutic or prophylactic effect. Generally, out of 100%, this amount ranges from approximately 1% to approximately 99%, preferably from approximately 5% to approximately 70%, and ideally from approximately 10% to approximately 30%, active ingredient.

As dosage forms, there are capsules, tablets, pills, granules, powders, syrups, lozenges (sucrose and acacia or tragacanth are usually used as preferred bases), emulsions, suppositories, injectable solutions, and the like. Liquid preparations such as emulsions and syrups which are suitable for oral administration can be produced by employing water, sugars such as sucrose, sorbitol, and fructose, glycols such as polyethylene glycol and propylene glycol, oils such as a sesame oil, olive oil, and soybean oil, preservatives such as p-hydroxybenzoic acid esters, flavorings such as strawberry flavor, peppermint, and the like. In addition, capsules, tablets, powders, granules, and the like can be produced by using excipients such as lactose, glucose, sucrose, and mannitol, disintegrating agents such as starch and sodium alginate, lubricants such as magnesium stearate and talc, binding agents such as polyvinyl alcohol, hydroxypropyl cellulose, and gelatin, surfactants such as fatty acid esters, plasticizers such as glycerin, and the like. Alternatively, the preparation may be a solution or suspension in an aqueous or non-aqueous liquid, an oil-in-water or water-in-oil liquid emulsion, an elixir or syrup, or aromatic tablet (using gelatin and glycerin, or sucrose and acacia or another such inert base) and/or mouth wash. Each contains a predetermined amount of a compound of the present invention as an active ingredient. The compound of the present invention can also be administered as a bolus, electuary, or paste.

Formulations suitable for parenteral administration comprise sterile aqueous formulations containing an active compound which is preferably isotonic with the blood of the recipient. For example, in the case of an injectable solution, a solution for injection is prepared using a carrier comprised of saline, glucose solution, or a mixture of saline and glucose solution.

In the present specification, "pharmaceutically acceptable carrier" means a pharmaceutically acceptable material, composition, or vehicle, for example, a liquid or solid filler, diluent, excipient, solvent, or encapsulating material, which is contained to carry or transport the compound of the present specification into or to a subject so that it can function as intended. Typically, such a compound can be carried or transported from one organ or part of the body to another organ or part of the body. Each carrier must be "acceptable" in the sense that it is compatible with other ingredients of the formulation and is not harmful to the patient. Some examples of materials which can work as pharmaceutically acceptable carriers include: sugars such as lactose, glucose, and sucrose; starches such as corn starch and potato starch; celluloses such as carboxymethylcellulose sodium, ethyl cellulose, and cellulose acetate and derivatives thereof; powdered tragacanth; malt; gelatin; talc; excipients such as cocoa butter and suppository wax; oils such as peanut oil, cottonseed oil, safflower oil, sesame oil, olive oil, corn oil, and soybean oil; glycols such as propylene glycol; polyols such as glycerin, sorbitol, mannitol, and polyethylene glycol; esters such as ethyl oleate and ethyl laurate; agar; buffers such as magnesium hydroxide and aluminum hydroxide; alginic acid; pyrogen-free water; isotonic physiological saline; Ringer's solution; ethyl alcohol; phosphate buffer; and other non-toxic compatible materials utilized in pharmaceutical formulations.

In a specific embodiment, compounds of the present invention may contain one or more acidic functional groups and, therefore, can form a pharmaceutically acceptable salt with a pharmaceutically acceptable base. Regarding such a salt or base, for example, Berge S. M. et al., "Pharmaceutical Salt", J. Pharm. Sci, 1977; 66:1-19 can be referred (this is incorporated in the present specification as a reference).

Topical formulations are prepared by dissolving or suspending an active compound in one or more kinds of media, for example, mineral oil, petroleum, polyhydric alcohol, or other bases used in topical pharmaceutical formulations. Formulations for intraintestinal administration are provided as suppositories by preparation using ordinary carriers, for example, cacao butter, hydrogenated fat, and hydrogenated fat carboxylic acid, and the like.

In the present invention, one or more kinds of auxiliary ingredients selected from the glycols, oils, flavorings, preservatives (including antioxidants), excipients, disintegrating agents, lubricants, binding agents, surfactants, plasticizers, and the like given as examples in oral agents can also be added in parenteral agents.

Examples of pharmaceutically acceptable antioxidants include water-soluble antioxidants such as ascorbic acid, cysteine hydrochloride, sodium bisulfate, sodium metabisulfate, and sodium sulfite; oil-soluble antioxidants such as ascorbyl palmitate, butylated hydroxyanisole (BHA), butylated hydroxytoluene (BHT), lecithin, propyl gallate, and α-tocopherol; and metal chelating agents such as citric acid, ethylenediaminetetraacetic acid (EDTA), sorbitol, tartaric acid, and phosphoric acid, and the like.

A suitable daily or one-time dose of a compound of the present invention, pharmaceutically acceptable salt thereof, or the like is the amount of compound which is the minimum amount effective for manifesting a therapeutic effect or prophylactic effect. It is understood that the effective dose and number of administrations of a compound of the present invention, pharmaceutically acceptable salt thereof, or the like differs depending on the dosage form, patient's age, weight, nature of the symptom to be treated, subjected to therapy, or prevented. The oral dose is usually 0.01-1000 mg/person/day, preferably 5-500 mg/person/day. The number of administrations is preferably once a day or divided. The intravenous dose and subcutaneous dose of a compound of the present invention, pharmaceutically acceptable salt thereof, or the like for a patient is generally approximately 0.0001-approximately 100 mg/kg body weight/day, more preferably approximately 0.01-approximately 50 mg/kg body weight/day, and even more preferably approximately 0.1-approximately 40 mg/kg body weight/day, when used for the indicated analgesic effect, and the effective therapeutic or prophylactic dose is, for example, 0.1-20 mg/kg body weight, more preferably 1-10 mg/kg body weight. For example, between approximately 0.01 µg to 20 mg, between approximately 20 mg and 100 mg, and between 10 mg and 200 mg of a compound of the present invention is administered per 20 g body weight of the subject. It should be noted that there is a possibility that the dosage value will change in association with the type and severity of the state to be alleviated.

The method of preparing these formulations or compositions includes a step for combining a compound of the present invention with a carrier and, optionally, one or more kinds of auxiliary ingredients. Generally, formulations are prepared by a step that uniformly and closely combines a compound of the present invention with a liquid carrier, or a finely divided solid carrier, or both of them and, then, molds a product if necessary.

In the present specification, in solid dosage forms (capsules, tablets, pills, sugar-coated tablets, powders, granules, and the like) of the present invention for oral administration, an active ingredient is mixed with one or more kinds of pharmaceutically acceptable carriers, for example, sodium citrate or dipotassium phosphate and/or any of the followings: fillers or bulking agents such as starch, lactose, sucrose, glucose, mannitol, and/or silicic acid; binding agents such as carboxymethylcellulose, alginate, gelatin, polyvinylpyrrolidone, sucrose and/or acacia; humectants such as glycerol; disintegrating agents such as agar, calcium carbonate, potato or tapioca starch, alginic acid, a specific silicic acid, and sodium carbonate; solution retardants [sic] such as paraffin; absorption-accelerating agents such as quaternary ammonium compounds; wetting agents such as cetyl alcohol and glycerol monostearate; absorbents such as kaolin and bentonite clay; lubricants such as talc, calcium stearate, magnesium stearate, solid polyethylene glycol, sodium lauryl sulfate, and a mixture thereof; as well as coloring agents. In the case of capsules, tablets, and pills, a pharmaceutical composition may also contain buffers. The same type of solid composition may also be utilized as a filler in filled soft and hard gelatin capsules employing an excipient such as lactose, as well as high-molecular polyethylene glycol.

Tablets may be prepared by compression and molding together with one or more kinds of optionally selective auxiliary ingredients. Compressed tablets may be prepared by employing binding agents (e.g., gelatin or hydroxypropyl methylcellulose), lubricants, inert diluents, preservatives, disintegrating agents (e.g., sodium starch glycolate or crosslinked carboxymethylcellulose sodium), surfactants, or dispersants. Molded tablets may be prepared by molding a mixture of powdered compounds wetted with an inert liquid diluent using a suitable machine.

Tablets or other solid dosage forms of the pharmaceutical composition of the present invention, for example, sugar-coated tablets, capsules, pills, and granules, may be optionally given or prepared with coatings and shells, for example, enteric coatings and other coatings well-known in the field of pharmaceutical formulations. These also may be formulated using a variety of proportions of hydroxypropyl methylcellulose, other polymer matrices, liposomes and/or microspheres in order to provide delayed release or controlled release of an active ingredient therein, for example, in order to provide a desired release profile. These may be sterilized, for example, by filtration by passage through a bacteria-retaining filter, or by incorporating a sterile drug in the form of a sterile solid composition which can be dissolved in sterile water or a certain other sterile injectable media immediately before use. These compositions may also optionally contain an opacifier, or they may be compositions which release only an active ingredient, or preferentially release an active ingredient to a particular part of a gastrointestinal tract optionally in a delayed manner. Examples of embedding compositions which can be used include polymeric substances and waxes. The active ingredient, when appropriate, can be a microencapsulated type accompanied by one or more kinds of the excipients.

A liquid dosage form for oral administration of a compound of the present invention includes pharmaceutically acceptable emulsions, microemulsions, solutions, suspensions, syrups, and elixirs. In addition to an active ingredient which can be used in the present invention, the liquid dosage form can include inert diluents which are generally used in the art, for example, water and other solvents, solubilizers and emulsifying agents, for example, ethyl alcohol, isopropyl alcohol, ethyl carbonate, ethyl acetate, benzyl alcohol, benzyl benzoate, propylene glycol, 1,3-butylene glycol, oils (particularly, cottonseed oil, peanut oil, corn oil, germ oil, olive oil, castor oil, and sesame oil), glycerol, tetrahydrofuryl alcohol, polyethylene glycol and sorbitan fatty acid esters, and mixtures thereof.

An oral composition of the present invention can also contain, in addition to the inert diluents, adjuvants such as wetting agents, emulsifying agents and suspending agents, sweeteners, perfumes, coloring materials, aromatic agents, and preservatives.

A suspension of the present invention may contain, in addition to an active compound of the present invention, a suspension, for example, ethoxylated isostearyl alcohol, polyoxyethylene sorbitol, and sorbitan ester, microcrystalline cellulose, aluminum metahydroxide, bentonite, agar and tragacanth, and mixtures thereof.

A formulation of the pharmaceutical composition of the present invention may be provided as a suppository for rectal or vaginal administration, and this can be prepared by mixing one or more kinds of suitable non-irritating excipients or carriers including, for example, cocoa butter, polyethylene glycol, suppository wax or salicylate, which are solid at room temperature but are liquid at a body temperature and, therefore, dissolve in the rectum or vaginal cavity, and release an active compound, with at least one compound of the present invention.

The formulation of the present invention also encompasses pessaries, tampons, creams, gels, pastes, foams, or spray preparations, containing carriers which are known in the art to be appropriate for vaginal administration.

Dosage forms for topical or transdermal administration of a compound of the present invention includes powders, sprays, ointments, pastes, creams, lotions, gels, solutions, patches, and inhalants. An active compound may be mixed with a pharmaceutically acceptable carrier and an optional preservative, buffer, or propellant which can be deemed necessary, under sterile conditions.

To ointments, pastes, creams, and gels may be added excipients such as animal and vegetable fats, oils, waxes, paraffins, starches, tragacanth, cellulose derivatives, polyethylene glycol, silicone, bentonite, silicic acid, talc and zinc dioxide, or mixtures thereof, in addition to an active compound of the present invention.

Powders and sprays can contain, in addition to the compound of the present invention, excipients such as lactose, talc, silicic acid, aluminum hydroxide, calcium silicate, and polyamide powder, or a mixture of these substances. Sprays can further include conventional propellants, such as volatile unsubstituted hydrocarbons such as chlorofluorohydrocarbons as well as butane and propane.

Transdermal patches have an additional advantage of providing controlled delivery of the compound of the present invention to the body. Such a dosage form can be made by dissolving or dispersing a compound in a suitable medium. An absorption-potentiating agent can be also used for increasing inflow of the compound crossing the skin. The rate of such inflow can be controlled by either provision of a rate-controlling membrane or dispersion of the active compound in a polymer matrix or a gel.

It is intended that the present invention encompass ophthalmic formulations, ocular ointments, powders, solutions, and the like, and such solutions are useful in the treatment, therapy, and prevention of conjunctivitis.

The pharmaceutical composition of the present invention is used for parenteral administration, contains at least one composition of the present invention combined with a pharmaceutically acceptable sterile isotonic aqueous solution or non-aqueous solution, a dispersion, suspension, or emulsion, or a sterile powder which can be reconstituted into a sterile injection solution or dispersion immediately before use, and these may contain antioxidants, buffers, bacteriostatic agents, solutes which are isotonic with the blood of the recipient for whom the formulation is intended, or suspending agents or thickeners.

Examples of suitable aqueous and non-aqueous carriers which may be utilized in the pharmaceutical composition of the present invention include water, ethanol, polyol (e.g., glycerol, propylene glycol, polyethylene glycol, and the like), and suitable mixtures thereof, vegetable oil, for example, olive oil, and injectable organic esters, for example, ethyl oleate. Suitable flowability can be maintained by the use of a coating material such as lecithin, maintenance of the necessary particle size in the case of a dispersion, and use of a surfactant.

These compositions may also contain adjuvants such as preservatives, wetting agents, emulsifying agents, dispersants, and the like. Interference with the action of microorganisms may be guaranteed by inclusion of a variety of antibacterial agents and anti-fungal agents, for example, paraben, chlorobutanol, phenol, sorbic acid, and the like. It can be also desired that an isotonizing agent, for example, sugar, sodium chloride, or the like be contained in the composition. In addition, prolongation of the absorption of an injectable pharmaceutical type can be attained by inclusion of an agent which delays absorption such as aluminum monostearate, gelatin, or the like.

In certain cases, in order to prolong the effect of a drug, it is desired that the absorption of a drug be delayed after subcutaneous or intramuscular injection. This may be attained by using a liquid suspension of a crystalline or amorphous substance having poor water-solubility. The rate of absorption of the drug then depends on the rate of its dissociation, and can then depend on crystal size and crystal form. Alternatively, delayed absorption of a drug form which has been administered parenterally is attained by dissolving or suspending the drug in an oil vehicle.

An injectable depot form can be prepared by forming a microcapsule matrix of a subject compound in a biodegradable polymer such as polylactide-polyglycolide. Depending on the ratio of the drug to the polymer, the properties of the particular polymer utilized and the rate of drug release can be controlled. Examples of other biodegradable polymers include poly(orthoesters) and poly(anhydrides). A depot injectable formulation can be also prepared by encapsulation of a drug in liposomes or a microemulsion which is compatible with body tissues.

The present invention also provides a packaged medicament comprising a novel compound described throughout the present specification, for use in the treatment, therapy, or prevention of a variety of disease states and symptoms.

In the present specification, "prevention" refers to eliminating the occurrence or at least delaying a disease, disorder, or symptom, by any means, before occurrence of the disease, disorder, or symptom which is a target of the present invention, or creating a state where even if the cause itself of a disease, disorder, or symptom arises, no disorder occurs based on the cause.

In the present specification, "therapy" refers to arresting the progression of a disease, disorder, or symptom which is a target of the present invention, which has already developed, or to improving, whether completely or partially, a disease, disorder, or symptom which is a target of the present invention. In the present specification, an act such as the treatment of a target subject by the administration of a compound of the present invention, composition, or the like to arrest the progression of a disease, disorder, or symptom which is a target of the present invention, which has already developed, or to improving, whether completely or partially, a disease, disorder, or symptom which is a target of the present invention is also referred to as "treatment." The two terms, however, are understood to be used interchangeably in the present specification unless specifically stated otherwise.

In the present specification, "subject" refers to an animal that is subject to a disease, disorder, or symptom which is a target of the present invention. Animals that are the subjects of the present invention may be, for example, birds, mammals, and the like. Preferably, such animals can be mammals (e.g., monotremes, marsupials, edentates, Dermatoptera, Chiroptera, carnivores, insectivores, proboscideans, perissodactyls, Artiodactyla, Tubulidentata, Squamata, Sirenia, Cetacea, primates, rodents, Lagomorpha, and the like). Exemplary subjects include, but are not limited to, animals such as cows, pigs, horses, chickens, cats, dogs, and the like. More preferably, small animals such as mice, rats, rabbits, hamsters, guinea pigs, and the like can be used. Of course, subjects of the present invention include humans, dogs, cats, cows, goats, and mice.

Preparations of the present invention can be administered orally, parenterally, topically, or rectally. These are naturally given in a form that is suited to the route of administration. For example, these are administered in the form of tablets or capsules by administration by injection, introduction, or inhalation of an injection, inhalant, eye lotion, ointment, suppository, or the like; topically by lotion or ointment; and rectally by suppository.

In the present specification, the terms "parenteral administration" and "administered parenterally" refer to other than oral administration when used in this specification and usually mean administration other than topical and enteral administration by injection. Included in non-limiting fashion are intravenous, intramuscular, intra-arterial, intra-arachnoid space, intracapsular, intra-orbital, intracardiac, intracutaneous, intraperitoneal, pertracheal, subcutaneous, subdermal, intra-articular, subcapsular, subarachnoid, intramedullary, and intrasternal injection and infusion.

In the present specification, the terms "systemic administration," "administered systemically," "peripheral administration," and "administered peripherally" refer to the administration of a compound, drug, or other substance other than directly to the central nervous system when used in this specification, and, as a result, mean administration to supply it to the system of a patient and thereby subject it to metabolism and other similar processes, for example, subcutaneous administration.

Compounds of the present invention can be administered to humans and other animals for therapy by a suitable arbitrary route, including orally, by spraying, for example, in the nose, rectally, intravaginally, parenterally, intracisternally, and topically, by powders, including buccal and sublingual formulations, ointments, or drops.

Regardless of the selected administration route, the compound of the present invention, which may be used in the form of a suitable hydrate, and/or the pharmaceutical composition of the present invention can be formulated into a pharmaceutically acceptable dosage form by conventional methods known to a person skilled in the art.

The actual dosage level of the active ingredient in a pharmaceutical composition of the present invention can vary so that an amount of active ingredient effective for attaining a desired therapeutic response in a particular patient, composition, and mode of administration are obtained without associated toxicity to the patient.

The selected dosage level depends on a variety of factors including the activity of a particular compound, ester, salt, or amide of the present invention being utilized, the route of administration, administration timing, rate of excretion of a particular compound being utilized, the duration of therapy, other drugs, compounds and/or substances being used in combination with a particular compound being utilized, the age, sex, weight, condition, general health status, and the previous medical history of the patient being treated, as well as similar factors well-known in the medical field.

A physician or a veterinarian having normal skill in the art can easily determine and formulate the required effective amount of the pharmaceutical composition. For example, a physician or a veterinarian can initiate administration of a compound of the present invention in a pharmaceutical composition at a level less than that required for attaining the desired therapeutic effect, and gradually increase the dosage until the desired effect is attained.

Generally, a suitable daily dose of a compound of the present invention is the amount of the compound which is an effective minimum dose for generating a therapeutic effect. Such an effective dose generally depends on the aforementioned factors. Generally, an intravenous dose and subcutaneous dose of a compound of the present invention for a patient, when used for the indicated analgesic effect, are in a range of approximately 0.0001 to approximately 100 mg/kg body weight/day, more preferably approximately 0.01 to approximately 50 mg/kg body weight/day, and more preferably, approximately 0.1 to approximately 40 mg/kg body weight/day. For example, a compound of the present invention in a range from approximately 0.01 µg to 20 µg, from approximately 20 µg to 100 µg, or from 10 µg to 200 µg, is administered per 20 g of weight of the subject.

When desired, an effective one-day dose of an active compound is administered optionally as 2, 3, 4, 5, 6 or more separate divided doses at suitable intervals throughout one day in a unit dosage form.

A pharmaceutical composition of the present invention contains a "therapeutically effective dose" or "prophylactically effective dose" of one or more types of compounds of the present invention. "Therapeutically effective dose" refers to the amount that is effective in the necessary dosage and time to attain the desired therapeutic result, for example, to reduce or prevent effects related to various disease states and symptoms. The therapeutically effective dose of the compounds of the present invention can change depending on the individual's disease state, age, sex, weight, and other such factors and the ability of the therapeutic compound to elicit the desired effect in the individual. A therapeutically effective dose is also one at which the therapeutically beneficial effects outweigh any toxicity or harmfulness of the therapeutic. "Prophylactically effective dose" refers to the amount that is effective in the necessary dosage and time to attain the desired prophylactic effect. Typically, the prophylactically effective dose is lower than the therapeutically effective dose since the prophylactically effective dose is used before or at an earlier stage in a disease.

The regimen can be adjusted to provide an optimal desired response (e.g., therapeutic response or prophylactic response). For example, a one-time bolus can be administered, several divided doses can be administered over time, or this dose can be proportionally decreased or increased as indicated by the requirements of the therapeutic state. For ease of administration and uniformity of dosage, it is particularly advantageous to formulate a parenteral composition in a unit dosage form. The term unit dosage form, when used in the present specification, refers to a physically discrete unit suitable as a unit dosage for a mammalian subject to be treated; each unit contains a predetermined amount of active ingredient calculated to generate the desired effect in cooperation with the required pharmaceutical carrier. The details of unit dosage forms of the present invention are determined by, and directly depend upon, (a) the unique properties of the compound of the present invention and the particular therapeutic or prophylactic effect to be attained, as well as (b) inherent limitations in the art to construct such an active compound for sensitive therapy in an individual.

An illustrative non-limiting range of therapeutically or prophylactically effective doses of compounds of the present invention is 0.1 to 20 mg/kg, more preferably 1 to 10 mg/kg. It should be noted that the dosage value varies with the type and severity of the state to be alleviated. It is to be further understood that, for an specific arbitrary subject, the specific disease, administration frequency, and the like should be adjusted over time according to individual needs, as well as the professional determination of the person who manages the composition or supervises administration of a composition, and the dosage range shown in the present specification is only illustrative, and does not intend to limit the scope or implementation of the present invention.

Delivery of compounds of the present invention to the lung by inhalation is one method described throughout the present specification for treating a variety of respiratory states (airway inflammation) including bronchial asthma, chronic obstructive lung diseases such as COPD, and other general local states. Compounds of the present invention can be administered to the lung in the form of an aerosol having particles of a respirable size (diameter of less than approximately 10 µm). This aerosol preparation can be provided as a liquid or a dry powder. In order to guarantee a suitable particle size in a liquid aerosol, particles can be prepared as a suspension in a respirable size and can then be incorporated into a suspension formulation containing a propellant. Alternatively, a formulation can be prepared in the form of a solution in order to avoid concern regarding the suitable particle size in a formulation. A solution formulation should be dispersed in a manner that produces particles or liquid droplets of a respirable size.

Once prepared, the aerosol formulation is filled into an aerosol canister provided with a metered-dose valve. The formulation is dispensed via an actuator adapted to direct a dose from the valve to the subject.

The formulation of the present invention can be prepared by combining (i) a sufficient amount of at least one compound for providing a plurality of therapeutically effective doses; (ii) adding an effective amount water for stabilizing the respective formulation; (iii) a sufficient amount of a propellant for spraying a plurality of doses from an aerosol canister; and (iv) other optional selective ingredients, for example, ethanol as a co-solvent; and dispersing the ingredients. The ingredients can be dispersed by shaking using a conventional mixer or homogenizer, or by ultrasound energy. A bulk formulation can be moved to smaller individual aerosol vials by using a method of moving from valve to valve by filling pressure, or by using a conventional cold filling method. It is not required that the stabilizer used is soluble in the propellant in a suspension aerosol formulation. A stabilizer which is not sufficiently soluble can be coated on a suitable amount of drug particles, and the coated particles can then be incorporated into the formulation as described above.

A commonly used valve, preferably an aerosol canister provided with a metered-dose valve, can be also used to deliver the formulation of the present invention. The conventional neoprene and beech valve rubbers used in metered-dose valves for delivering conventional CFC formulations can be used for formulations containing HFC-134a or HFC-227. A partition formed by extrusion, injection molding, or compression molding from a thermoplastic elastomer material, for example, FLEXOMER™GERS 1085 NT polyolefin (Union Carbide) is also suitable.

The formulation of the present invention can be contained in a coated or uncoated, anodized or unanodized conventional aerosol canister, for example, an aluminum, glass, stainless steel, or polyethylene terephthalate canister.

The formulation of the present invention can be delivered to the respiratory tract and/or lung by oral inhalation, to produce bronchodilation or to treat a state sensitive to treatment by inhalation, for example, asthma, chronic obstructive lung disease, or the like as described throughout the present specification.

The formula of the present invention can also be delivered by nasal inhalation as known in the art for the treatment, therapy, or prevention of respiratory states as described throughout the present specification.

Compounds of the present invention can be administered alone, but are preferably administered as pharmaceutical compositions.

The present invention also encompasses packaging materials and products comprising a formulation of a compound of the present invention contained in a packaging material. This formulation contains at least one compound of the present invention, and the packaging material contains a label or package insert showing the prescribed dosage and prescribed frequency for treating one or more states described in the present specification by the formulation, the expiration date and subjects who can be administered for the treatment, therapy, or prevention of such states. Such states are described throughout the present specification and are incorporated into the present specification as a reference. Suitable compounds that can be utilized are those described in the present specification.

More specifically, the present invention features a packaging material and a formulation comprising at least one compound of the present invention contained in a packaging material. The packaging material contains a label or handling instructions showing that the formulation can be administered to a subject for the treatment, therapy, or prevention of symptoms related to conditions discussed throughout the present specification.

Based on the above, in one preferred aspect, the drug of the present invention is useful in the treatment, therapy, or prevention of conditions, disorders, states, and the like that include, but are not limited to, the following: pulmonary distress syndrome, adult respiratory distress syndrome, chronic obstructive pulmonary disease (COPD), and other such lung diseases; ischemic heart disease, ischemic kidney disease, ischemic brain disease, ischemic liver disease, and other such ischemic diseases; many gastrointestinal inflammatory disorders of the digestive system (mouth, stomach, esophagus, small intestine, and large intestine), for example, stomatitis, periodontal disease, esophagitis, gastritis, ulcerative colitis, Crohn's disease, and other such inflammatory intestinal conditions, infectious enteritis (viral, bacterial, parasitic), antibiotic-associated diarrhea, *Clostridium difficile* colitis, microscopic or lymphocytic colitis, collagenous colitis, colon polyps and familial polyp syndromes (e.g., familial polyposis syndrome, Gardner's syndrome), *Helicobacter pylori*, irritable bowel syndrome, non-specific diarrhea, and colon cancer; inflammatory bowel disease (IBD), colitis which is induced by stimulation from the outside world (e.g., inflammation of the stomach and intestine (e.g., colitis) caused by therapeutic regimens such as administration of chemotherapy and radiation therapy, or is associated therewith (e.g., as an adverse effect)), chronic granulomatous disease, celiac disease, celiac sprue (genetic disease in which the back layer of the intestine becomes inflamed in response to ingestion of a protein known as gluten), food allergy, gastritis, infectious gastritis, or enterocolitis (e.g., *Helicobacter pylori* infectious chronic active gastritis) and other types of gastrointestinal inflammation caused by an infectious factor; and stress-related conditions selected from erosive gastritis, gastric ulcer, duodenal ulcer, bronchial asthma, ulcerative colitis, arteriosclerosis, Crohn's disease, malignant tumor, ovarian cyst, salpingitis, uterine myoma, endometriosis, spontaneous abortion, toxemia of pregnancy, infertility, and dysmenorrhea.

The present invention can also provide treatment, therapy, or prevention of the following: including gastroenteritis, ulcerative colitis, Crohn's disease, infectious enteritis, antibiotic-associated diarrhea, *Clostridium difficile* colitis, microscopic or lymphocytic colitis, collagenous colitis, colon polyps, familial polyps, familial polyposis syndrome, Gardner's syndrome, *Helicobacter pylori*, irritable bowel syndrome, nonspecific diarrhea, and colon cancer or inflammatory diseases (allergic diseases (allergic dermatitis, allergic rhinitis, and the like), rheumatoid arthritis, anaphylaxis, and the like), arteriosclerosis, vascular and cardiovascular diseases, cancer and tumors (hyperproliferative imbalance), diseases of the immune system, cytoproliferative diseases, infections, and the like. Including, for example, psoriasis, pulmonary fibrosis, glomerulonephritis, cancer, atheromatous sclerosis, and anti-angiogenesis (e.g., tumor growth, diabetic retinopathy). Specifically, for example, the pharmaceutical composition of the present invention is an agent for the prevention and/or treatment of encephalitis, myelitis and encephalomyelitis, meningitis, inflammatory polyneuropathy, neuritis, dacryoadenitis, orbital inflammation, conjunctivitis (allergic conjunctivitis, spring keratoconjunctivitis, and the like), keratitis, chorioretinal scar, endophthalmitis, retrobulbar optic neuritis, retinopathy, glaucoma, cellulitis, otitis externa, perichondritis, otitis media, tympanitis, salpingitis, mastoiditis, myringitis, labyrinthitis, pulpitis, periodontitis, sialadenitis, stomatitis, glossitis, thyroiditis, pericarditis, endocarditis, myocarditis, hypertension, heart failure, arteriosclerosis (atherosclerosis and the like), restenosis, ischemic reperfusion syndrome, thrombosis (myocardial infarction, cerebral infarction, and the like), obesity, angiitis, vasculitis, multiple arteritis, lymphadenitis, lymphoma, Hodgkin's disease, eosinophilic diseases (eosinophilia, pulmonary eosinophilia, pulmonary aspergillosis, and the like), inflammatory or obstructive airway diseases (allergic rhinitis, chronic sinusitis, pneumonia, laryngitis, laryngotracheitis, bronchitis, asthma, acute pulmonary disorders, acute respiratory distress syndrome, pulmonary emphysema, chronic obstructive lung disease, and the like), pleuritis, pneumoconiosis, mesothelioma, esophagitis, gastrojejunal ulcer, gastritis, duodenitis, food allergy, septicemia, hepatitis, hepatic fibrosis, liver sclerosis, cholecystitis, pancreatitis, peritonitis, diabetes (type I diabetes, type II diabetes), inflammatory or allergic skin diseases (allergic dermatitis, contact dermatitis (allergic contact dermatitis, irritation contact dermatitis, and the like), psoriasis, urticaria, photoallergic reaction, alopecia greata, and the like), hypertrophic disorders of the skin (dermal eosinophilic granuloma, and the like), dermal polymyositis, inflammation of the subcutaneous adipose tissue, hyperthyroidism, sarcoidosis, autoimmune blood diseases (hemolytic anemia, idiopathic thrombocytopenic purpura, and the like), (systemic) lupus erythematosus, relapsing polychondritis, multiple leptomenigitis, sclerodoma, Wegener's granulomatosis, dermatomyositis, chronic active hepatitis, myasthenia gravis, Stevens-Johnson syndrome, idiopathic sprue, autoimmune inflammatory bowel diseases (ulcerative colitis, Crohn's disease, and the like), endocrine ophthalmopathy, sarcoidosis, alveolitis, chronic hypersensitivity pneumonitis, multiple sclerosis, primary biliary cirrhosis, uveitis, keratoconjunctivitis sicca, interstitial pulmonary fibrosis, iridocyclitis, psoriatic arthritis, glomerulonephritis, systemic sclerosis, systemic connective tissue diseases (Sjogren's syndrome, Behcet's disease, diffuse myofascitis, and the like), interstitial myositis, inflammatory polyarthritis, inflammatory arthritis, rheumatoid arthritis, osteoarthritis, synovitis, bursitis, thecitis, chronic multiple myelitis, nephritis syndrome, tubulointerstitial nephritis, cystitis, prostatitis, orchitis, epididymitis, salpingitis, ovaritis, trachelitis, female pelvic inflammatory disease, vulvovaginitis, organ transplant rejection, bone marrow transplant rejection, graft-versus-host disease or an agent for the treatment of burns or traumatic inflammation, and the like.

As described above, inflammatory changes associated with macrophage infiltration into adipose tissues contribute greatly to the disease state in obesity and insulin resistance (metabolic syndrome) (Tilg, H. and Moschen, A. R. (2006)

Nat. Rev. Immunol. 6, 772-783). Therefore, It is understood that compounds of the present invention are useful in such lifestyle diseases.

In another aspect, the present invention also relates to a method for the treatment, therapy, or prevention of gastrointestinal disease in a subject by administration in combination with other anti-inflammatories, for example, steroids or NSAIDs (aspirin, ibuprofen, and the like). These drugs can be administered simultaneously or at two different times.

All of the results in the figures and in the present specification are expressed as the mean±SE of the number of animals n per group. The determination of statistically significant differences was made by Student's t test. A p value of <0.05 (or 0.07, or 0.01, in some cases) is regarded as a significant difference.

(Methods of Analyzing Compounds of the Present Invention)

In one aspect, the present invention provides a method for analyzing compounds of the present invention or PUFA metabolites, solvates of these compounds or these metabolites, pharmaceutically acceptable salts of these compounds or these metabolites, and solvates of these salts. One can turn to human body fluids (blood, urine, breast milk), biopsy materials, and the like as therapeutic markers for evaluating the n-3 level effective as an indicator for assaying these compounds to develop a therapeutic basis for anti-inflammation. Included herein are LC-MS-MS and GC-MS properties. This can also result in far easier development for handling ELISA assay to monitor these novel products.

Therefore, the present invention is a method for analyzing compounds of the present invention or PUFA metabolites, solvates of these compounds or these metabolites, pharmaceutically acceptable salts of these compounds or these metabolites, and solvates of these salts and provides a method using the following liquid chromatography conditions: solution A: water/acetic acid=100/0.1 and solution B: acetonitrile/methanol=4/1, flow rate: 0-30 min→50 µL/min, 30-33 min→80 µL/min, 33-45 min→100 µL/min, the gradient described in FIG. 1A, and the parameters described in FIG. 1B using multiple reaction monitoring. Such a system, parameters, and the like can be used modified as is appropriate by those skilled in the art.

The MRM parent mass and daughter mass pair can be optimized (optimization of collision energy) from the measured MS/MS values for the compound synthesized (in the present case, this corresponds to one synthesized by enzyme, for example, an epoxy compound of the present invention or the like) under these setting conditions. When a calibration curve is created, quantitative analysis becomes possible. MRM for the purpose of detection can be performed by establishing hypothetical conditions for those that cannot be synthesized. The novel compounds of the present invention can be analyzed by using this method.

(General Techniques)

The molecular biology techniques, biochemistry techniques, and microbiology techniques used in the present specification are known in the art and are commonly used. For example, they are described in Sambrook J. et al. (1989), Molecular Cloning: A Laboratory Manual, Cold Spring Harbor and the $3^{rd}$ Ed. thereof (2001); Ausubel, F. M. (1987), Current Protocols in Molecular Biology, Greene Pub. Associates and Wiley-Interscience; Ausubel, F. M. (1989), Short Protocols in Molecular Biology: A Compendium of Methods from Current Protocols in Molecular Biology, Greene Pub. Associates and Wiley-Interscience; Innis M. A. (1990), PCR Protocols: A Guide to Methods and Applications, Academic Press; Ausubel, F. M. (1992), Short Protocols in Molecular Biology: A Compendium of Methods from Current Protocols in Molecular Biology, Greene Pub. Associates; Ausubel, F. M. (1995), Short Protocols in Molecular Biology: A Compendium of Methods from Current Protocols in Molecular Biology, Greene Pub. Associates; Innis, M. A. et al. (1995), PCR Strategies, Academic Press; Ausubel, F. M. (1999), Short Protocols in Molecular Biology: A Compendium of Methods form Current Protocols in Molecular Biology, Wiley and annual updates; Sninsky, J. J. et al. (1999), PCR Applications: Protocols for Functional Genomics, Academic Press, Experimental Medicine, supplement, "Gene Introduction & Expression Analysis Experimental Methods," Yodosha, 1997, and the like. These are incorporated as references in related parts (possibly all) in the present specification.

DNA synthesis techniques and nucleic acid chemistry for producing artificially synthesized genes are described, for example, in Gait, M. J. (1985), Oligonucleotide Synthesis: A Practical Approach, IRL Press; Gait, M. J. (1990), Oligonucleotide Synthesis: A Practical Approach, IRL Press; Eckstein, F. (1991), Oligonucleotides and Analogues: A Practical Approach, IRL Press; Adams, R. L. et al. (1992), The Biochemistry of the Nucleic Acids, Chapman & Hall; Shabarova, Z. et al. (1994), Advanced Organic Chemistry of Nucleic Acids, Weinheim; Blackburn, G. M. et al. (1996), Nucleic Acids in Chemistry and Biology, Oxford University Press; Hermanson, G. T. (1996), Bioconjugate Techniques, Academic Press, and the like. These are incorporated as references in related parts in the present specification.

Scientific documents, patents, patent applications, and other such reference documents cited in the present specification are incorporated in their entirety as references in the present specification to the same extent as those specifically described.

The present invention has been explained above by showing preferred embodiments to facilitate understanding. The present invention is explained below based on examples. Nonetheless, the foregoing explanation and the following examples are merely provided for the purpose of illustration and are not provided for the purpose of limiting the present invention. Therefore, the scope of the present invention is not limited by either embodiments or examples specifically described in the present specification and is limited only by the claims.

EXAMPLES

The present invention is explained in greater detail below through examples. However, the technical scope of the present invention is not limited by these examples. The reagents used below were commercial ones except where specifically stated.

Example 1

Establishment of a High-Sensitivity Analytical Method for PUFA Metabolites of Epoxy Compounds of the Present Invention In this example, a system capable of quantitatively analyzing PUFA metabolites at high sensitivity and quantitatively analyzing many types at once was established to make possible the analysis of novel compounds. In this example, a simultaneous quantitative analysis system for polyunsaturated fatty acids (PUFA) by multiple reaction monitoring (MRM) using ultra-high-performance liquid chromatography-tandem mass spectrometry (UPLC-MS/MS) was established.

MRM is a technique that permits the selective analysis of target metabolites at high sensitivity using MS/MS. When the MS/MS of metabolites of PUFA is measured, if they are oxides for example, fragmentation occurs at the carbon-carbon bonds in front of and behind their hydroxy groups. When this occurs, a characteristic MS/MS value is detected in the structure of that metabolite. Therefore, MRM is a technique that selectively detects only substances having a combination of a parent MS value/daughter MS value, taking the MS value derived from the molecular weight of a certain metabolite (molecular weight −1 is the MS value when ionized by removing a proton in the case of PUFA metabolites for negative ion mode) as the parent MS value ($M^-$) and the MS value characteristic of the structure of that metabolite as the daughter MS value ($A^-$). Specifically, using triplicate quadrupole-type MS, a pre-set parent MS value is first selectively detected by Q1. Other molecules are excluded at this time, and only molecules that have passed through Q1 have energy added at the next q2 and are fragmented. Only those having a pre-set daughter MS value among the fragments generated are selectively detected by the next Q3. Taking this combination of parent MS value/daughter MS value as one channel, the respective combinations of parent MS value/daughter MS value and the optimum cone voltages and collision energies for each are set as one channel for all target molecules. Since the scan speed of one channel is approximately 30 msec, the time taken by a single scan, even analyzing the channels of 100 types of metabolites, is approximately 3 seconds. Therefore, detection of the metabolite is possible if the elution time of the metabolite when separated by LC is 3 seconds or longer. Theoretically, more than 300 types of metabolites can be detected since the actual elution time is some tens of seconds. However, when the fact that detection is carried out near the peak top is taken into account, up to hundreds of types of metabolites can be analyzed simultaneously while also retaining quantitativeness. Moreover, the combination of a separation system using LC also obtains information on the specific retention time of each metabolite, and high-sensitivity, simultaneous quantitative analysis of a target metabolite group can be carried out based on this information.

In this example, synthetic products were purchased and used for virtually all of the compounds. However, those that could not be purchased were produced by enzymatic reaction. Specific examples are given in Example 2 below.

(Purification of Compounds Using Normal-Phase HPLC)
Hexane: Wako Pure Chemical Industries
Isopropanol: Wako Pure Chemical Industries
Acetic acid: Wako Pure Chemical Industries
(Establishment of a Simultaneous Analysis System for PUFA Metabolites by MRM)

The following compositions were used in analysis. The method of procurement (number of the example in which it was produced) is also listed (hy means hydroxy, Ep means epoxy).

5hy-17,18-EpETE: Example 2
8hy-17,18-EpETE: Example 5
12hy-17,18-EpETE: Example 3
15hy-17,18-EpETE: Example 4
4hy-19,20-EpDPE: Example 2
7hy-19,20-EpDPE: Example 2
10hy-19,20-EpDPE: Example 5
13hy-19,20-EpDPE: Example 2
14hy-19,20-EpDPE: Example 3
17hy-19,20-EpDPE: Example 4
10hy-19,20-EpDTE: Example 2
14hy-19,20-EpDTE: Example 2
17hy-19,20-EpDTE: Example 2

These parameters are listed in FIG. 1B.
(LC Solvents)
Acetic acid: Wako Pure Chemical Industries
Methanol: Wako Pure Chemical Industries
Acetonitrile: Wako Pure Chemical Industries
(Establishment of a Simultaneous Quantitative Analysis System for PUFA Metabolites by MRM)
(MS/MS Measurement of Standard Compounds)

Each of the compounds used as standards was prepared to make approximately 1 μM by methanol/Milli-Q/acetic acid=90/10/0.1 solution. MS/MS was measured by Q-TRAP-5500 (Applied Biosystem) while feeding approximately 150 μL at 10 μL/min.

(Optimization of Cone Voltage and Collision Energy)

The MS/MS values characteristic of the structure of that compound were selected from the MS/MS values measured, and the conditions that would detect that MS/MS value at the best sensitivity were determined by conducting measurements by varying the cone voltage and collision energy.

(Study of Separation Conditions by LC)

A UPLC (Waters) was used as the pump, and an Acquity UPLC BEH $C_{18}$ 1.7 μm (1.0×150 mm) was used as the column. The fundamental solvents were solution A: Milli-Q/acetic acid=100/0.1 and solution B: acetonitrile/methanol=4/1. The ratios and flow rates were adjusted every hour, and conditions that eluted a mixture of standard compounds with a good degree of separation within 30 minutes were determined. The final LC conditions were as follows.

Refer to FIG. 1A and the following table for the solvent gradients. The MRM parent mass and daughter mass pairs can be optimized (optimization of collision energy) from the measured MS/MS values of compounds synthesized (e.g., those synthesized by enzymes; corresponding to the epoxy compounds of the present invention) under the conditions established. Quantitative analysis also becomes possible when a calibration curve is created. MRM for the purpose of detection can be carried out by establishing hypothetical conditions for those not synthesized.

Flow rate: 0-30 min→50 μL/min
30-33 min→80 μL/min
33-45 min→100 μL/min.

TABLE 1

| Min | A (%) | B (%) | Flow rate (μL/min) |
|---|---|---|---|
| 0 | 73 | 27 | 50 |
| 5 | 73 | 27 | 50 |
| 15 | 30 | 70 | 50 |
| 25 | 20 | 80 | 50 |
| 30 | 20 | 80 | 50 |
| 33 | 20 | 80 | 80 |
| 35 | 0 | 100 | 80 |
| 45 | 0 | 100 | 100 |

A: Milli-Q/acetic acid = 100/0.1
B: Acetonitrile/methanol = 4/1

(Creation of a Calibration Curve Using Standard Compounds)

A dilution series from 5 pg/10 μL to 1 ng/10 μL was prepared using standard compounds and analyzed by the established LC conditions and MRM program, and a calibration curve was created. The peak height was taken to be the signal intensity.

(Results)

(Establishment of a Simultaneous Quantitative Analysis System for PUFA Metabolites by MRM)

(Establishment of a Simultaneous Analysis System for PUFA Metabolites)

Using the standard compounds, a specific MRM channel was created for each compound. Hypothetical channels were created using MS/MS values estimated from the structure and the cone voltage and collision energy of metabolites of similar structure as references when no standard compound existed, as in the case of metabolites of completely novel structure and the like. A simultaneous analysis system for compounds of the present invention was established as a result of the accumulation of this work (FIG. 1B).

(Study of LC Separation Conditions)

Next, the conditions to separate the PUFA metabolites well were studied. PUFA metabolites (oxides) basically have oxygen (hydroxy group) added at various positions in the PUFA carbon chain and are difficult to separate because their structures are extremely similar. A system that separates PUFA metabolites very well in 45 minutes was established when acetonitrile, methanol, and water were mixed in various ratios and the flow rate was optimized.

(Creation of a Calibration Curve)

Mixtures of standard compounds were measured by varying the amounts using the MRM measurement method established in this example. As a result, a calibration curve having high accuracy in the 5 pg-1 ng range was drawn.

We succeeded above in establishing a high-sensitivity, simultaneous quantitative analysis system for PUFA metabolites.

Example 2

Synthesis of 5-hydroxy-17,18-epoxy-ETE, 4-hydroxy-19,20-epoxy-DPE, 7-hydroxy-19,20-epoxy-DPE, 13-hydroxy-19,20-epoxy-DPE, 10-hydroxy-19,20-epoxy-DTE, 14-hydroxy-19,20-epoxy-DTE, and 17-hydroxy-19,20-epoxy-DTE The title compounds were synthesized in this example. In this example, a method was used whereby a hydroxy compound was produced first, and the hydroxy compound obtained was epoxidated.

(Materials)

3-Morpholinopropanesulfonate buffer (MOPS buffer) (pH 7.4): MOPS (Wako Pure Chemical Industries) was dissolved in Milli-Q water. The pH was set at 7.4 by adding 1N sodium hydroxide (Wako Pure Chemical Industries), and MOPS was then brought to 50 mM by Milli-Q water.

Recombinant cytochrome P450 BM3: The target gene was induced by adding pentobarbital to make 1 μM to *Bacillus megaterium*. The RNA was extracted from it, amplified by RT-PCR, inserted into a pET21a DNA (Takara) vector, and transformed in BL-21 competent cells. *E. coli* with the gene introduced was cultured in LB medium, and protein induction was performed at 20° C. by adding isopropyl-β-thiogalactopyranoside (IPTG) to make 1 mM. After induction, the *E. coli* was crushed, the supernatant obtained by centrifugation was introduced into a nickel column, and the target protein was purified.

Nicotinamide Adenine Dinucleotide Phosphate (NADPH): (Wako Pure Chemical Industries)

Various HEPE (5-HEPE), HDoHE (4-HDoHE, 7-HDoHE, and 13-HDoHE): Cayman, HDoPEs were synthesized by enzyme as following.

Diethyl ether: Showa Ether

Materials for separation by reverse-phase HPLC

Methanol: Wako Pure Chemical Industries 0.01% v/v acetic acid: Acetic acid (Wako Pure Chemical Industries) was added to Milli-Q water to make 0.01% by v/v. Furthermore, "Milli-Q water" in the present specification indicates ultra-pure water prepared by an ultra-pure water production instrument available from Millipore (e.g., Milli-Q Advantage).

(Method)

(a1. Synthesis of a Precursor (Synthesis of a Metabolite Derived from DPA) by Enzymatic Reaction)

(Synthesis of 10-HDoPE)

n-3 DPA (Sigma) was placed in a reactor, and the solvent was driven off by nitrogen. In this regard, DPA was dissolved by adding PBS to make 30 μg/mL. An enzymatic reaction was advanced here by adding 8-LOX to make 17 μg/mL, and a reduction reaction was performed thereafter using $NaBH_4$. The fatty acid metabolite was extracted using diethyl ether.

(Synthesis of 14-HDoPE)

n-3 DPA (Sigma) was placed in a reactor, and the solvent was driven off by nitrogen. In this regard, DPA was dissolved by adding Tris hydrochloride buffer (pH 7.4) to make 30 μg/mL. An enzymatic reaction was advanced here by adding 12-LOX, and a reduction reaction was performed thereafter using $NaBH_4$. The fatty acid metabolite was extracted using diethyl ether.

(Synthesis of 17-HDoPE)

n-3 DPA (Sigma) was placed in a reactor, and the solvent was driven off by nitrogen. In this regard, DPA was dissolved by adding borate (pH 9.0) to make 10 μg/mL. An enzymatic reaction was advanced here by adding soybean lipoxygenase (sLOX), and a reduction reaction was performed thereafter using $NaBH_4$. The fatty acid metabolite was extracted using diethyl ether.

The above monohydroxy compounds were used below in the synthesis of epoxy compounds by reaction with P450 BM3.

(a2. Synthesis by Enzymatic Reaction)

The precursors HEPE (5-HEPE), HDoHE (4-HDoHE, 7-HDoHE, and 13-HDoHE), and HDoPE (10-HDoPE, 14-HDoPE, and 17-HDoPE) were placed in a reactor, and the solvent was driven off by nitrogen. In this regard, HEPE, HDoPE [sic], and HDoPE were dissolved by adding MOPS buffer to make a concentration of 30 μg/mL. After adding P450 BM3 to make 50 nM and allowing to stand for five minutes at room temperature, the reaction was advanced by adding NADPH to make 1 mM. The fatty acid metabolites were extracted using diethyl ether.

(b. Separation and Purification of Compounds by Reverse-Phase HPLC)

The solvent of fatty acid metabolites prepared as described above was driven off by nitrogen, and they were dissolved in the HPLC initial mobile phase ($H_2O$/MeOH/acetic acid=45/55/0.01). This was subjected to HPLC (Agilent Technologies) and finally stored as an ethanol solution at −20° C. The reverse-phase HPLC conditions were as follows.

Mobile Phase

Solution A: Methanol

Solution B: Milli-Q water/acetic acid 100/0.01

| 0-5 min | A 55% |
|---|---|
| 5-25 min | A 55% → 100% (gradient) |
| 25-35 min | A 100% |

Column: XBridge C18 5 μm, 4.6×100 mm column (Waters)
Flow rate: 0.7 mL/min
(Results)

Figures 1, 3A:
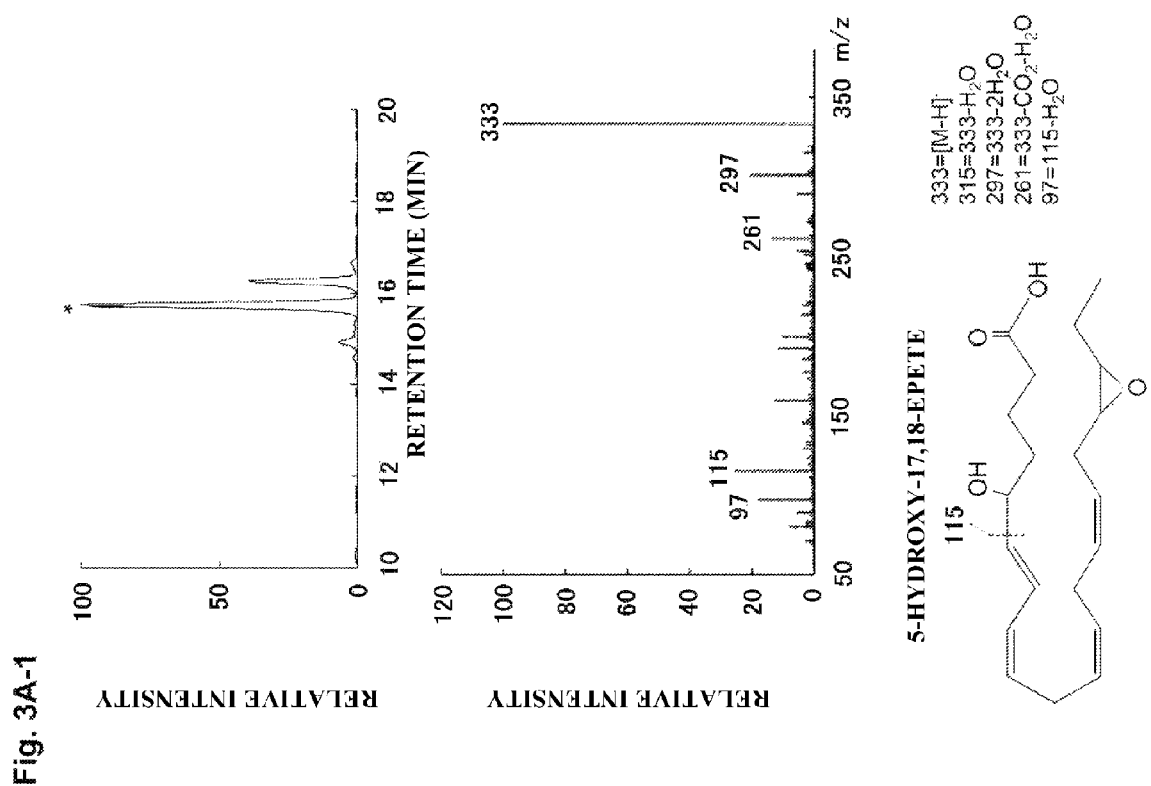
[FIG. 3A-1]
Figures 2, 3A:
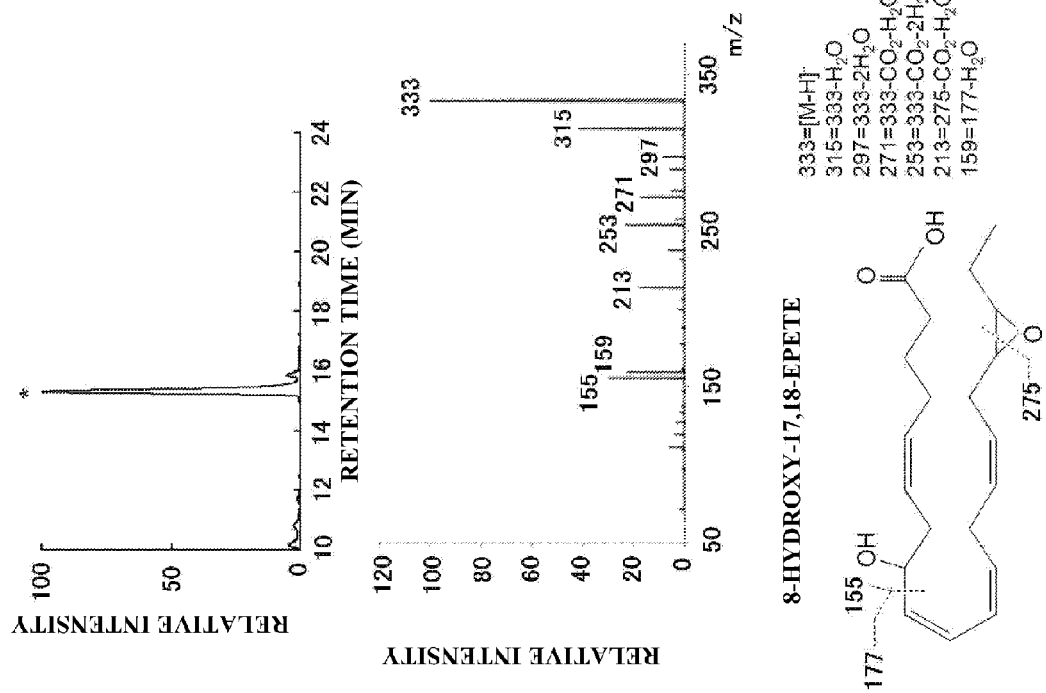
Figures 3, 3A:
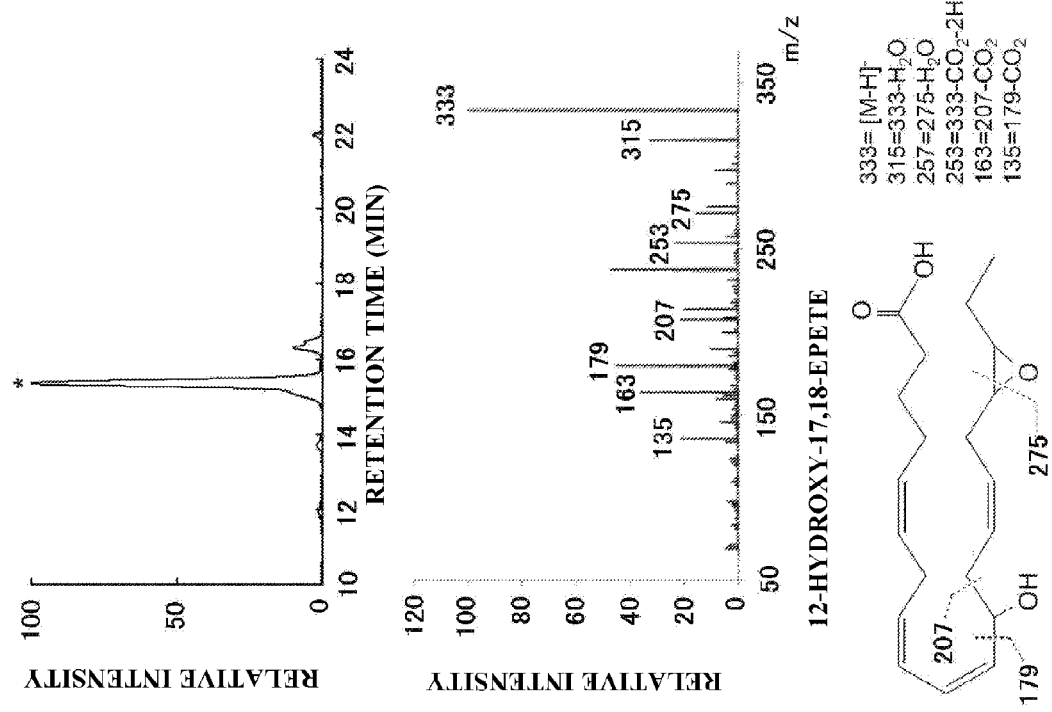
Figures 3, 3A, 4:
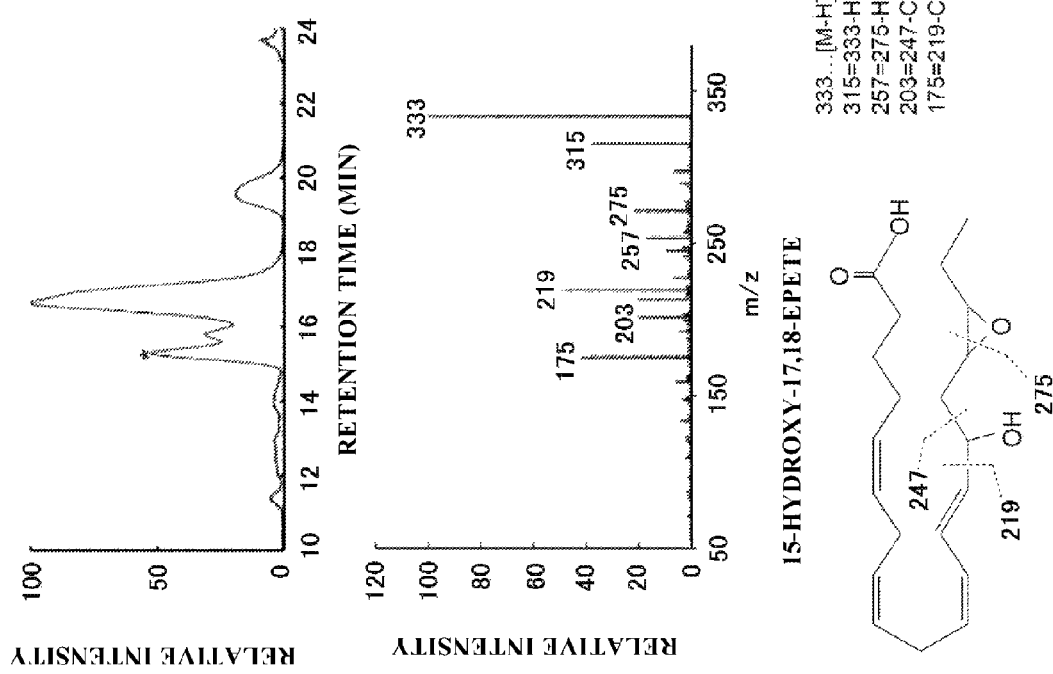
Figures 1, 3B:
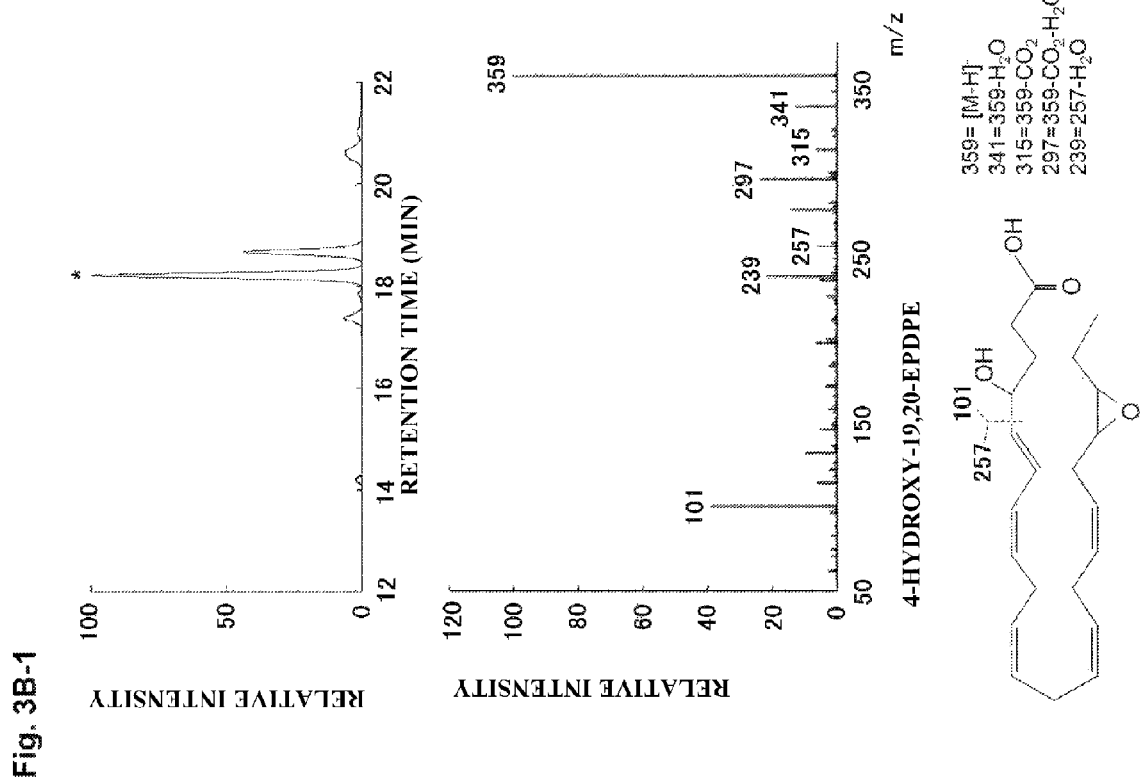
Figure 3B:
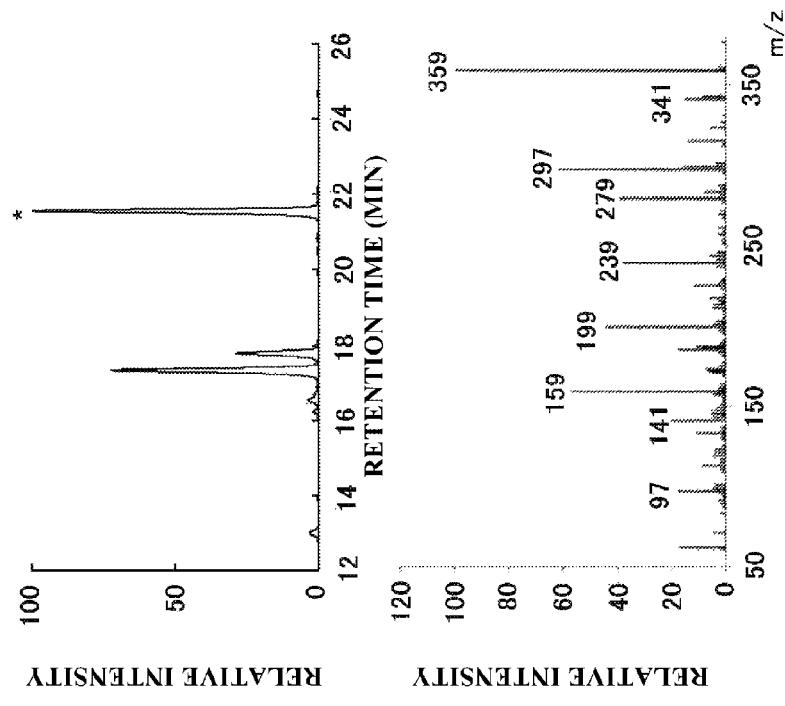
Figure 2:
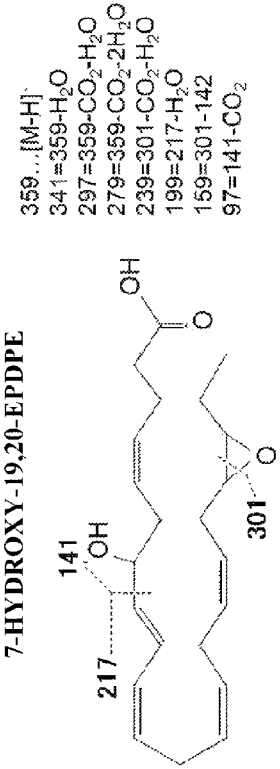
Figures 3, 3B:
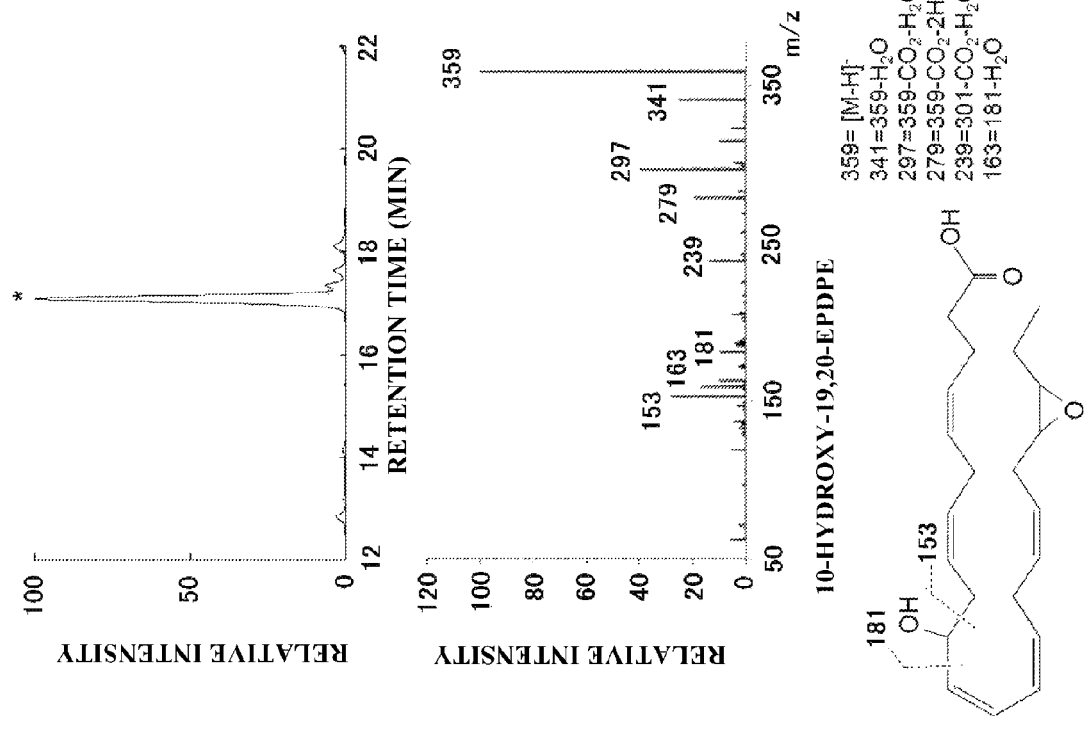
Figures 3, 3B, 4:
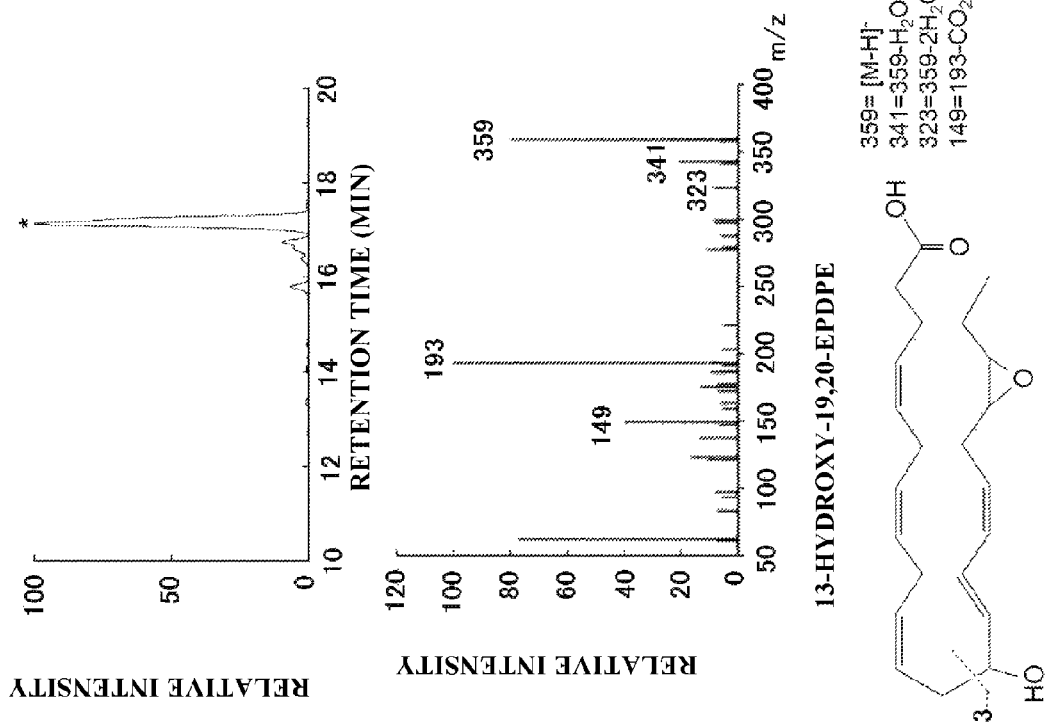

The production of 5-hydroxy-17,18-epoxy-ETE, 4-hydroxy-19,20-epoxy-DPE, 7-hydroxy-19,20-epoxy-DPE, 13-hydroxy-19,20-epoxy-DPE, 10-hydroxy-19,20-epoxy-DTE, 14-hydroxy-19,20-epoxy-DTE, and 17-hydroxy-19,20-epoxy-DTE was confirmed by the above results. FIGS. 3A-3D show the results of mass analysis of the compounds synthesized in Examples 2-5. The results of Example 2 are shown in FIGS. 3A, 3B, and 3D.

FIG. 3A-1 shows 5-hydroxy-17,18-epoxy-ETE (5hy-17,18-EpETE). Each graph shows the mass (m/z) on the horizontal axis and the relative intensity of the signal on the vertical axis.

FIG. 3B-1 shows 4-hydroxy-19,20-epoxy-DPE (4hy-19,20-EpDPE). FIG. 3B-2 shows 7-hydroxy-19,20-epoxy-DPE (7hy-19,20-EpDPE). FIG. 3B-4 shows 13-hydroxy-19,20-epoxy-DPE (13hy-19,20-EpDPE). Each graph shows the mass (m/z) on the horizontal axis and the relative intensity of the signal on the vertical axis.

FIG. 3D shows the results determined by mass analysis (MS/MS) of structural information on compounds derived from DPA. Shows the continuation of the results determined by mass analysis (MS/MS) of structural information on compounds derived from DPA [sic]. FIG. 3D-1 shows 10-hydroxy-19,20-epoxy-DPE (14[sic]hy-19,20-EpDPE). FIG. 3D-2 shows 14-hydroxy-19,20-epoxy-DPE (14hy-19,20-EpDPE). FIG. 3D-3 shows 17-hydroxy-19,20-epoxy-DPE (17hy-19,20-EpDPE). Each graph shows the mass (m/z) on the horizontal axis and the relative intensity of the signal on the vertical axis.

Example 3

Synthesis of 12-hydroxy-17,18-epoxy-ETE and 14-hydroxy-19,20-epoxy-DPE

In this example, of 12-hydroxy-17,18-epoxy-ETE and 14-hydroxy-19,20-epoxy-DPE were synthesized.
(Materials)
Materials used to produce hydroxy compounds by enzymatic reaction:
Tris hydrochloride buffer (also referred to as "Tris" in the present specification) (pH 7.4): Tris was dissolved in Milli-Q water. The pH was set at 7.4 by adding concentrated hydrochloric acid, and Tris was brought to 100 mM by Milli-Q water.
Recombinant Porcine 12-LOX: Sigma
Sodium tetrahydroborate (sodium borohydride, $NaBH_4$): Wako Pure Chemical Industries
17,18-Epoxy ETE and 19,20-epoxy DPE: Cayman
Diethyl ether: Showa Ether
Material used in separation by reverse-phase HPLC:
Methanol: Wako Pure Chemical Industries
0.01% v/v acetic acid: Acetic acid (Wako Pure Chemical Industries) was added to Milli-Q water to make 0.01% by v/v.
(Method)
(Synthesis by Enzymatic Reaction)
17,18-epoxy-ETE or 19,20-epoxy-DPE was placed in a reactor, and the solvent was driven off by nitrogen. In this regard, 17,18-epoxy-ETE or 19,20-epoxy-DPE was dissolved by adding Tris hydrochloride buffer to make 30 μg/mL. In this regard, an enzymatic reaction was advanced by adding 12-LOX to make 8 units/mL, and a reduction reaction was performed thereafter using $NaBH_4$. The fatty acid metabolite was extracted using diethyl ether.

(Separation and Purification of Compounds by Reverse-Phase HPLC)
The solvent of fatty acid metabolites prepared as described above was driven off by nitrogen, and they were dissolved in the HPLC initial mobile phase ($H_2O$/methanol (MeOH)/acetic acid=45/55/0.01). This was subjected to HPLC (Agilent Technologies) and finally stored as an ethanol solution at −20° C. The reverse-phase HPLC conditions were as follows.
Mobile Phase
Solution A: Methanol
Solution B: Milli-Q water/acetic acid 100/0.01

| 0-5 min | A 55% |
| 5-25 min | A 55% → 100% (gradient) |
| 25-35 min | A 100% |

Column: XBridge C18 5 μm, 4.6×100 mm column (Waters)
Flow rate: 0.7 mL/min
(Results)
12-Hydroxy-17,18-epoxy-ETE and 14-hydroxy-19,20-epoxy-DPE were produced as a result of this example. The results are shown in FIGS. 3A and 3C.

FIG. 3A-3 shows 12-hydroxy-17,18-epoxy-ETE (12-hy-17,18-EpETE). Each graph shows the mass (m/z) on the horizontal axis and the relative intensity of the signal on the vertical axis.

Figures 1, 3C:
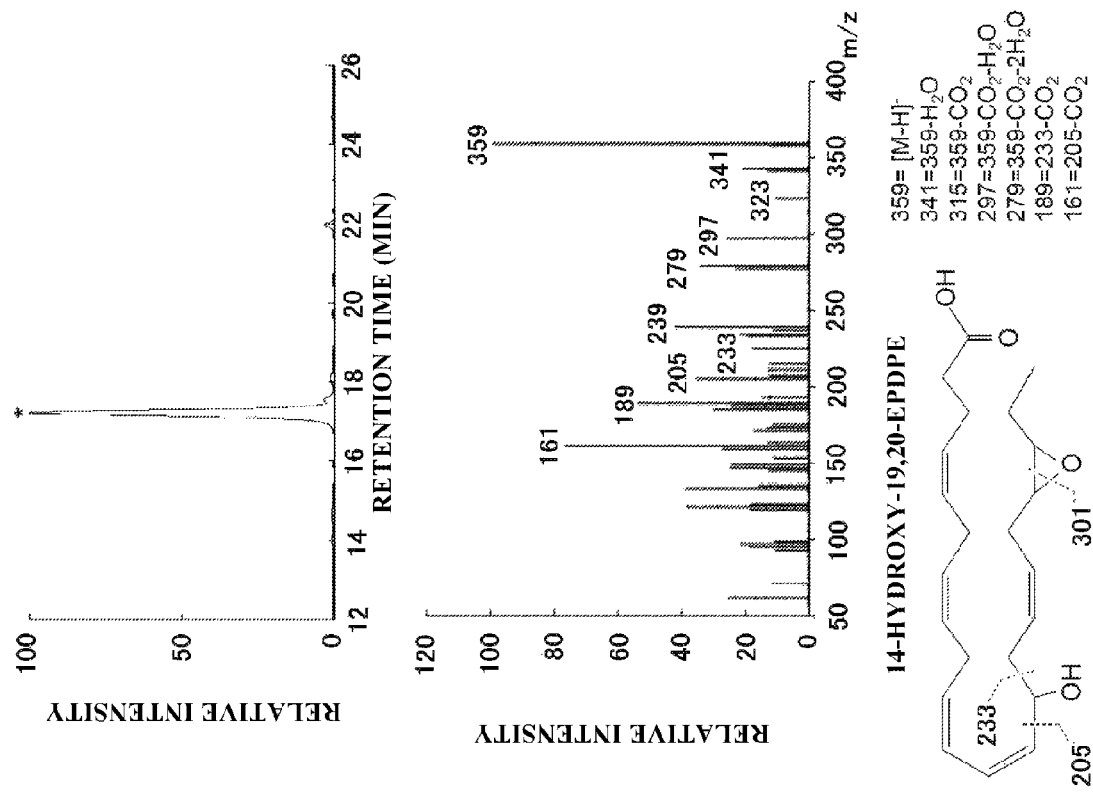
Figures 2, 3C:
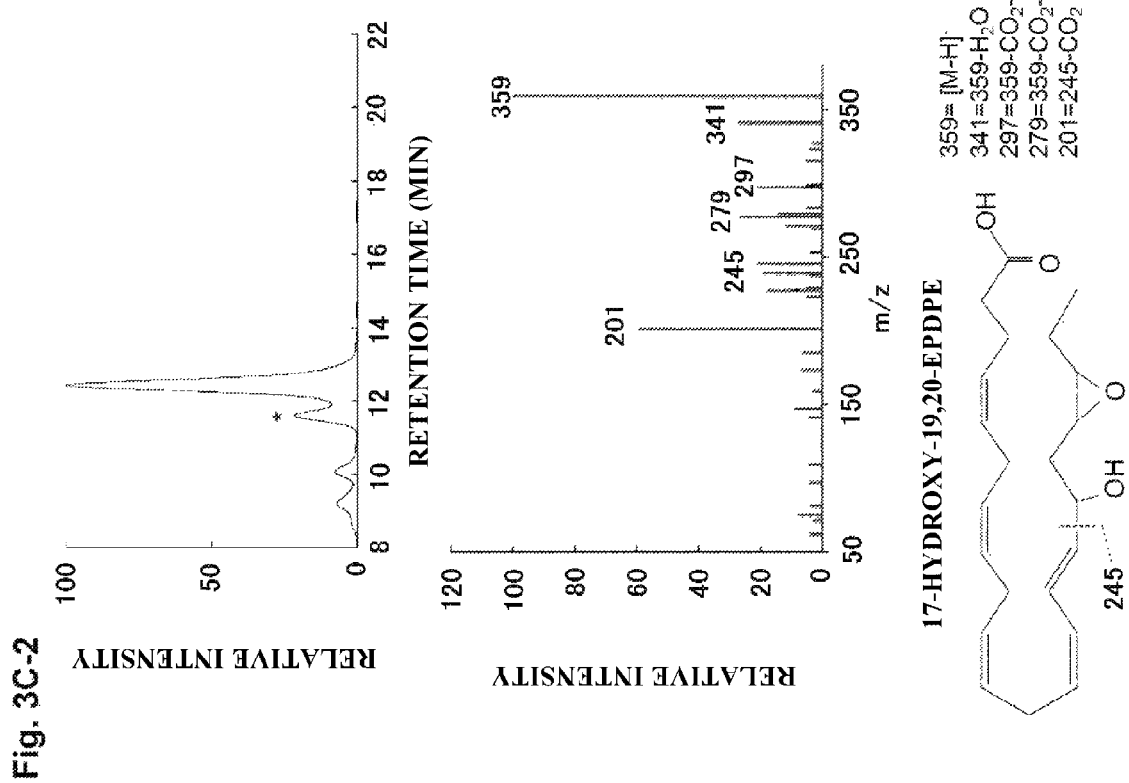
Figures 1, 3D:
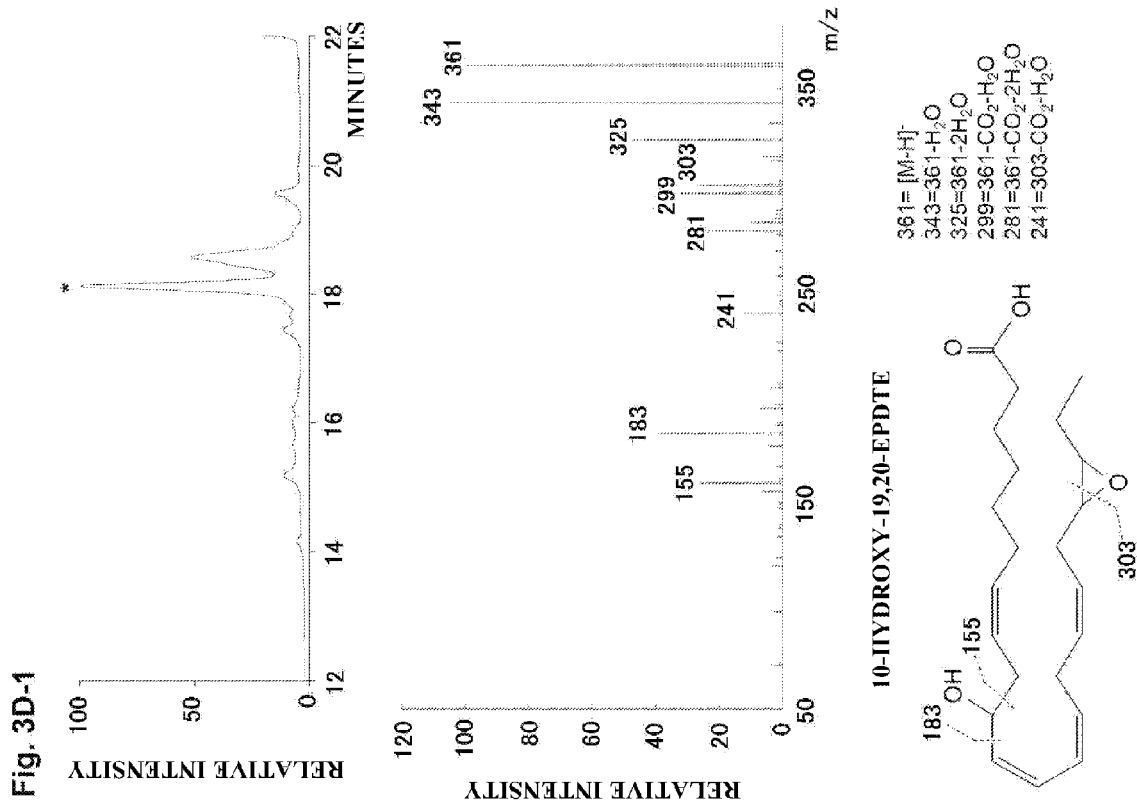
Figures 2, 3D:
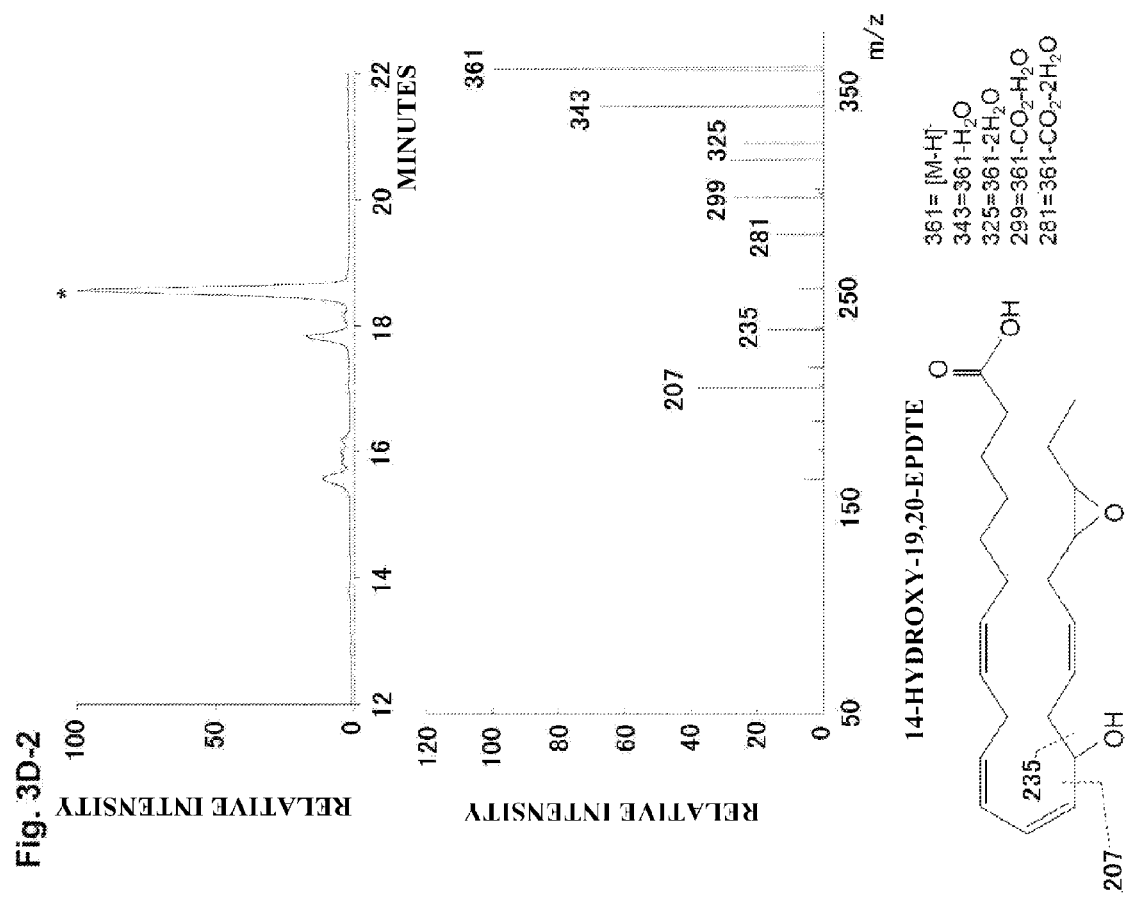
Figures 3, 3D:
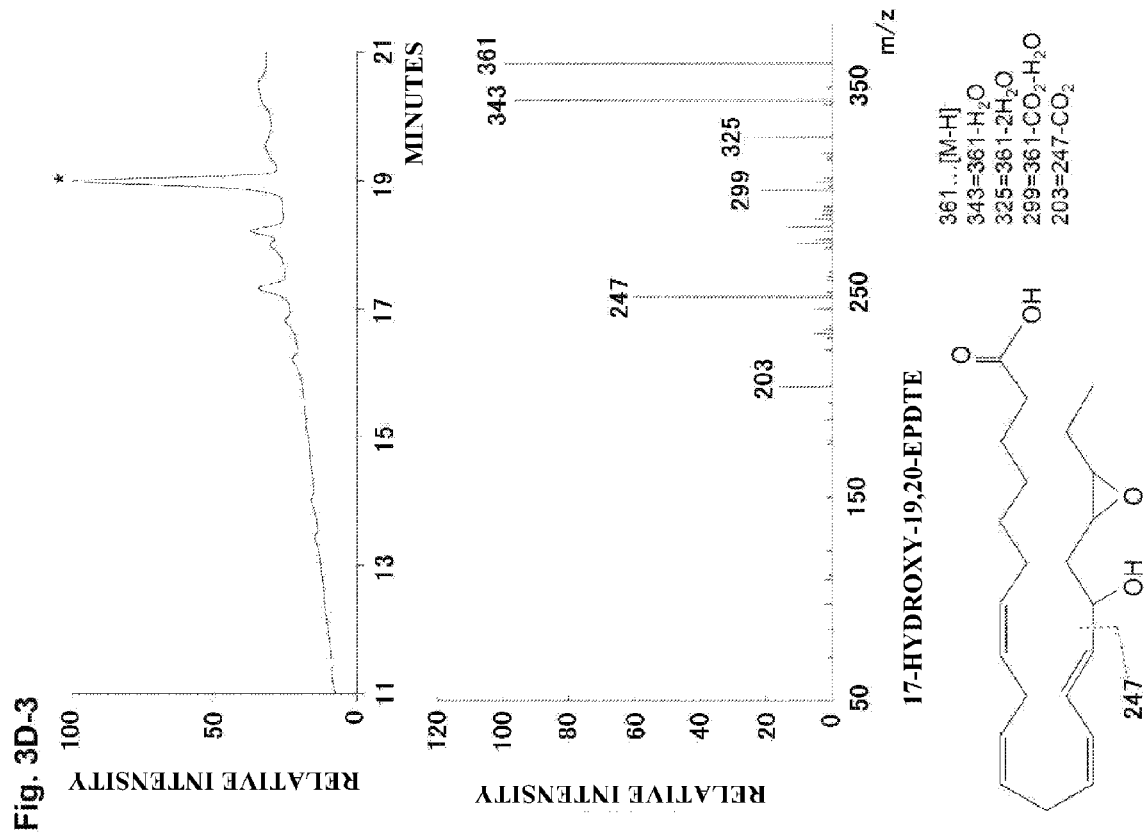

FIG. 3C-1 shows 14-hydroxy-19,20-epoxy-DPE (14hy-19,20-EpDPE). Each graph shows the mass (m/z) on the horizontal axis and the relative intensity of the signal on the vertical axis.

Example 4

Synthesis of 15-hydroxy-17,18-epoxy-ETE and 17-hydroxy-19,20-epoxy-DPE

Next, 15-hydroxy-17,18-epoxy-ETE and 17-hydroxy-19,20-epoxy-DPE were synthesized in this example.
(Materials)
Materials used in production of hydroxy compounds by enzymatic reaction:
Borate buffer (pH 9.0): Boric acid and potassium chloride (both Wako Pure Chemical Industries) were dissolved in Milli-Q water. The pH was set at 9.0 by adding 1N potassium hydroxide (Wako Pure Chemical Industries), and the boric acid and potassium chloride were brought to 50 mM by Milli-Q water.
Soybean lipoxygenase (sLOX): Sigma
Sodium tetrahydroborate ($NaBH_4$): Wako Pure Chemical Industries
17,18-epoxy ETE and 19,20-epoxy DPE: Cayman
Diethyl ether: Showa Ether
Material used in separation by reverse-phase HPLC:
Methanol: Wako Pure Chemical Industries
0.01% v/v acetic acid: Acetic acid (Wako Pure Chemical Industries) was added to Milli-Q water to make 0.01% by v/v.
(Method)
(a. Synthesis by Enzymatic Reaction)
17,18-epoxy-ETE or 19,20-epoxy-DPE was placed in a reactor, and the solvent was driven off by nitrogen. In this regard, 17,18-epoxy-ETE or 19,20-epoxy-DPE was dissolved by adding Tris hydrochloride buffer to make 30 μg/mL. In this regard, an enzymatic reaction was advanced by adding sLOX to make 20,000 units/mL, and a reduction reaction was performed thereafter using $NaBH_4$. The fatty acid metabolite was extracted using diethyl ether.

(b. Separation and Purification by Reverse-Phase HPLC)

The solvent of fatty acid metabolites prepared as described above was driven off by nitrogen, and they were dissolved in the HPLC initial mobile phase ($H_2O$/MeOH/acetic acid=45/55/0.01). This was subjected to HPLC (Agilent Technologies) and finally stored as an ethanol solution at −20° C. The reverse-phase HPLC conditions were as follows.

Mobile Phase
Solution A: Methanol
Solution B: Milli-Q water/acetic acid 100/0.01

(Conditions used for 17,18-EpETE Reaction Product)

| 0-21 min | A 65% |
| 21-35 min | A 100% |

(Conditions Used for 19,20-EpDPE Reaction Product)

| 0-21 min | A 70% |
| 21-35 min | A 100% |

Column: An XBridge Shield RP18 3.5 μm, 4.6×100 mm column (Waters) was used for 15-hydroxy-17,18-epoxy-ETE, and an XBridge C18 5 μm, 4.6×100 mm column (Waters) was used for 17-hydroxy-19,20-epoxy-DPE.

Flow rate: 0.7 mL/min.

(Results)

15-Hydroxy-17,18-epoxy-ETE and 17-hydroxy-19,20-epoxy-DPE were produced as a result of this example. The results are shown in FIGS. 3A and 3C.

FIG. 3A-4 shows 15-hydroxy-17,18-epoxy-ETE (15hy-17,18-EpETE). Each graph shows the mass (m/z) on the horizontal axis and the relative intensity of the signal on the vertical axis.

FIG. 3C-2 shows 17-hydroxy-19,20-epoxy-DPE (17hy-19,20-EpDPE). Each graph shows the mass (m/z) on the horizontal axis and the relative intensity of the signal on the vertical axis.

Example 5

Synthesis of 8-hydroxy-17,18-epoxy-ETE and 10-hydroxy-19,20-epoxy-DPE

8-Hydroxy-17,18-epoxy-ETE and 10-hydroxy-19,20-epoxy-DPE were synthesized in this example.

(Materials)

Materials used to produce hydroxy compounds by enzymatic reaction:

Phosphate-buffered physiological saline (PBS): Prepared as appropriate from 137 mM sodium chloride (NaCl), 2.7 mM potassium chloride (KCl), 10 mM disodium hydrogen phosphate ($Na_2HPO_4$), and 2 mM potassium dihydrogen phosphate ($KH_2PO_4$).

Recombinant murine 8-lipoxygenase (8-LOX): RNA was extracted from mouse skin, amplified by RT-PCR, inserted into a pCold TF DNA (Takara) vector, and transformed in BL-21 competent cells. E. coli with the gene introduced was cultured in LB medium, and protein induction was performed at 15° C. by adding isopropyl-β-thiogalactopyranoside (IPTG) to make 1 mM. After induction, the E. coli was crushed, the supernatant obtained by centrifugation was introduced into a nickel column, and the target protein was purified.

Sodium tetrahydroborate ($NaBH_4$): Wako Pure Chemical Industries 17,18-epoxy ETE and 19,20-epoxy DPE: Cayman Diethyl ether: Showa Ether Material used in separation by reverse-phase HPLC:

Methanol: Wako Pure Chemical Industries 0.01% v/v acetic acid: Acetic acid (Wako Pure Chemical Industries) was added to Milli-Q water to make 0.01% by v/v.

(Method)

(a. Synthesis by Enzymatic Reaction)

17,18-epoxy-ETE or 19,20-epoxy-DPE was placed in a reactor, and the solvent was driven off by nitrogen. In this regard, 17,18-epoxy-ETE or 19,20-epoxy-DPE was dissolved by adding PBS to make 30 μg/mL. In this regard, an enzymatic reaction was advanced by adding 8-LOX to make 0.1 mg/mL, and a reduction reaction was performed thereafter using $NaBH_4$. The fatty acid metabolite was extracted using diethyl ether.

(b. Separation and Purification of Compounds by Reverse-Phase HPLC)

The solvent of fatty acid metabolites prepared as described above was driven off by nitrogen, and they were dissolved in the HPLC initial mobile phase ($H_2O$/(MeOH/acetic acid=45/55/0.01). This was subjected to HPLC (Agilent Technologies) and finally stored as an ethanol solution at −20° C. The reverse-phase HPLC conditions were as follows.

Mobile Phase
Solution A: Methanol
Solution B: Milli-Q water/acetic acid 100/0.01

| 0-5 min | A 55% |
| 5-25 min | A 55% → 100% (gradient) |
| 25-35 min | A 100% |

Column: XBridge C18 5 μm, 4.6×100 mm column (Waters)

Flow rate: 0.7 mL/min.

(Results)

8-Hydroxy-17,18-epoxy-ETE and 10-hydroxy-19,20-epoxy-DPE were produced as a result of this example. The results are shown in FIGS. 3A and 3B.

FIG. 3A-2 shows 8-hydroxy-17,18-epoxy-ETE (8hy-17,18-EpETE). Each graph shows the mass (m/z) on the horizontal axis and the relative intensity of the signal on the vertical axis.

FIG. 3B-3 shows 10-hydroxy-19,20-epoxy-DPE (10hy-19,20-EpDPE). Each graph shows the mass (m/z) on the horizontal axis and the relative intensity of the signal on the vertical axis.

Example 6

Evaluation of the Bioactivity of Compounds of the Present Invention

In this example, the bioactivity of compounds synthesized in the above examples was evaluated in a peritonitis model, and the anti-inflammatory activity was evaluated.

(Materials)

(1. Induction of Zymosan Peritonitis)

Mice C57BL/6J, 7 weeks old, male: Japan CLEA

Physiological saline: Otsuka Pharmaceutical

Zymosan A: Wako Pure Chemical Industries

Phosphate-buffered physiological saline (PBS)
(2. FACS Three-Color Stain (CD11b, Gr-1, F4/80))
Anti-mouse CD16/CD32 (0.5 mg/mL): BD Biosciences
FITC anti-mouse F4/80 (0.5 mg/mL): eBioscience
PE anti-mouse Ly-6G&Ly-6C (Gr-1) (0.2 mg/mL): eBioscience
PerCP-Cy5.5 anti-mouse CD11b (Mac-1) (0.2 mg/mL): eBioscience
Staining antibody mix
FITC anti-mouse F4/80 1.0 μL/sample
PE anti-mouse Ly-6G&Ly-6C 0.5 μL/sample
PerCP-Cy5.5 anti-mouse CD11b 0.5 μL/sample
Dilute the above antibodies by 50 μL/sample of PBS. Prepare at the time of use.
PBS: Same as in Example 5.
(3. Evaluation Using an Acute Lung Injury Model)
Mice C57BL/6J, 7 weeks old, male: Japan CLEA
Hydrochloric acid: Sigma
Nembutal: Dainippon Sumitomo Pharma Co., Ltd.
Ketamine: Daiichi Sankyo Propharma Co., Ltd.
Xylazine: Bayer Medical
PBS: Prepared as appropriate in the same way as in Example 5.
Physiological saline: Otsuka Pharmaceutical
Simple Giemsa stain solution Diffquick: Sysmex
(Method)
(a. Evaluation Using a Zymosan Peritonitis Model)
Zymosan peritonitis induced by intraperitoneal administration of zymosan, which is a cell wall component of yeast, was used as the inflammation model. This model is suited to the analysis of cytokines and eicosanoids since the intraperitoneal exudate can be recovered.

Zymosan A (Wako Pure Chemical Industries) was suspended in physiological saline to make 1 mg/mL and warmed for 30 minutes at 37° C. The zymosan A solution was then vortexed and returned to room temperature. A compound synthesized in a previous example was placed in a 1.5 mL tube and completely dried by driving off the solvent by nitrogen. It was then dissolved by adding physiological saline. Next, 100 μL of the compound solution was injected (1 ng or 10 ng/mouse) from a caudal vein of C57BL/6J mice (7 weeks old, male: Japan CLEA). Groups injected with only physiological saline (saline) or dexamethasone (10 μg/mouse), which is an anti-inflammatory steroid, were used as controls. Approximately two minutes later, 1 mL of zymosan A solution was administered intraperitoneally. Two hours later, cells that had exuded into the peritoneal cavity were recovered by tube by PBS, and the cells were counted. This tube was then centrifuged for five minutes at 1200 rpm, 4° C., and the supernatant was discarded. The precipitate (pellets) was suspended in PBS, and population analysis was performed by FACS three-color stain.

(b. FACS Three-Color Stain)
Peritoneal cells were adjusted to 2.5×10$^6$ cells/mL, and 200 μL was placed in a 5 mL round-bottomed tube (BD Falcon) (5×10$^5$ cells/tube). A quantity of 1 μL/tube of anti-mouse CD16/CD32 antibody (0.5 mg/mL; BD Biosciences) was added to this tube and incubated for 10 minutes at room temperature. Staining antibody mix (1.0 μL/sample of FITC-bound anti-mouse F4/80 antibody (0.5 mg/mL; eBioscience), 0.5 μL of PE-bound anti-mouse Ly-6G&Ly-6C antibody (0.2 mg/mL; eBioscience), and 0.5 μL of perCP-Cy5.5-bound anti-mouse CD11b antibody (0.2 mg/mL; eBioscience) per sample prepared by dilution by 50 μL of PBS) was added to this tube in a quantity of 50 μL/tube and incubated for 15 minutes at room temperature shielded from light. Measurement was performed by an FACS Calibur (BD Biosciences).

Figure 4B:
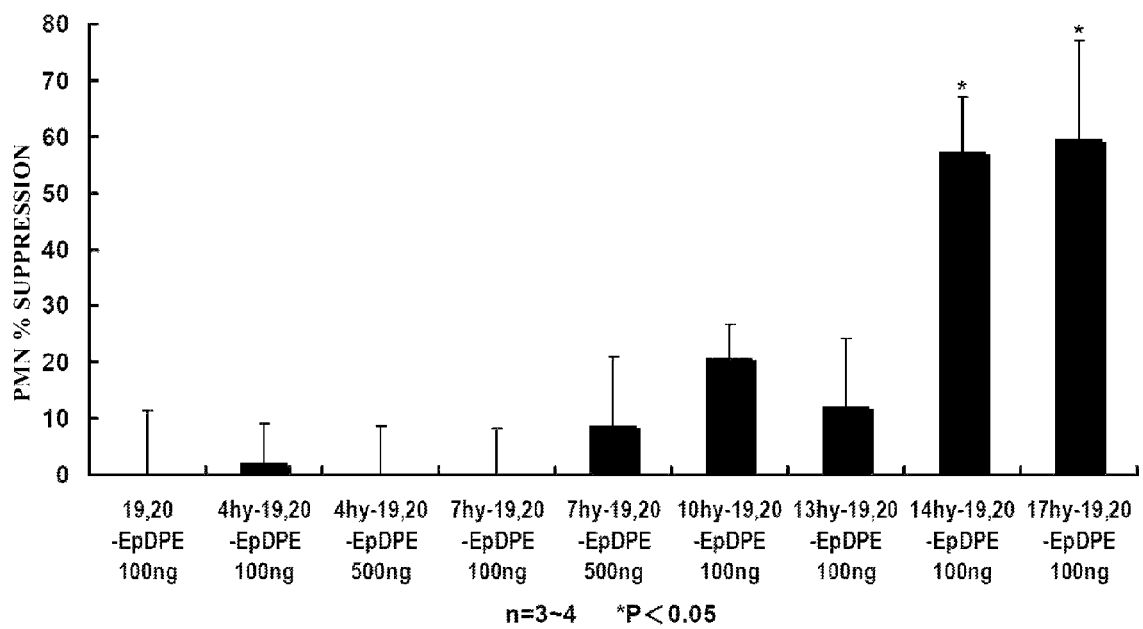
[FIG. 4B]
Figure 4C:
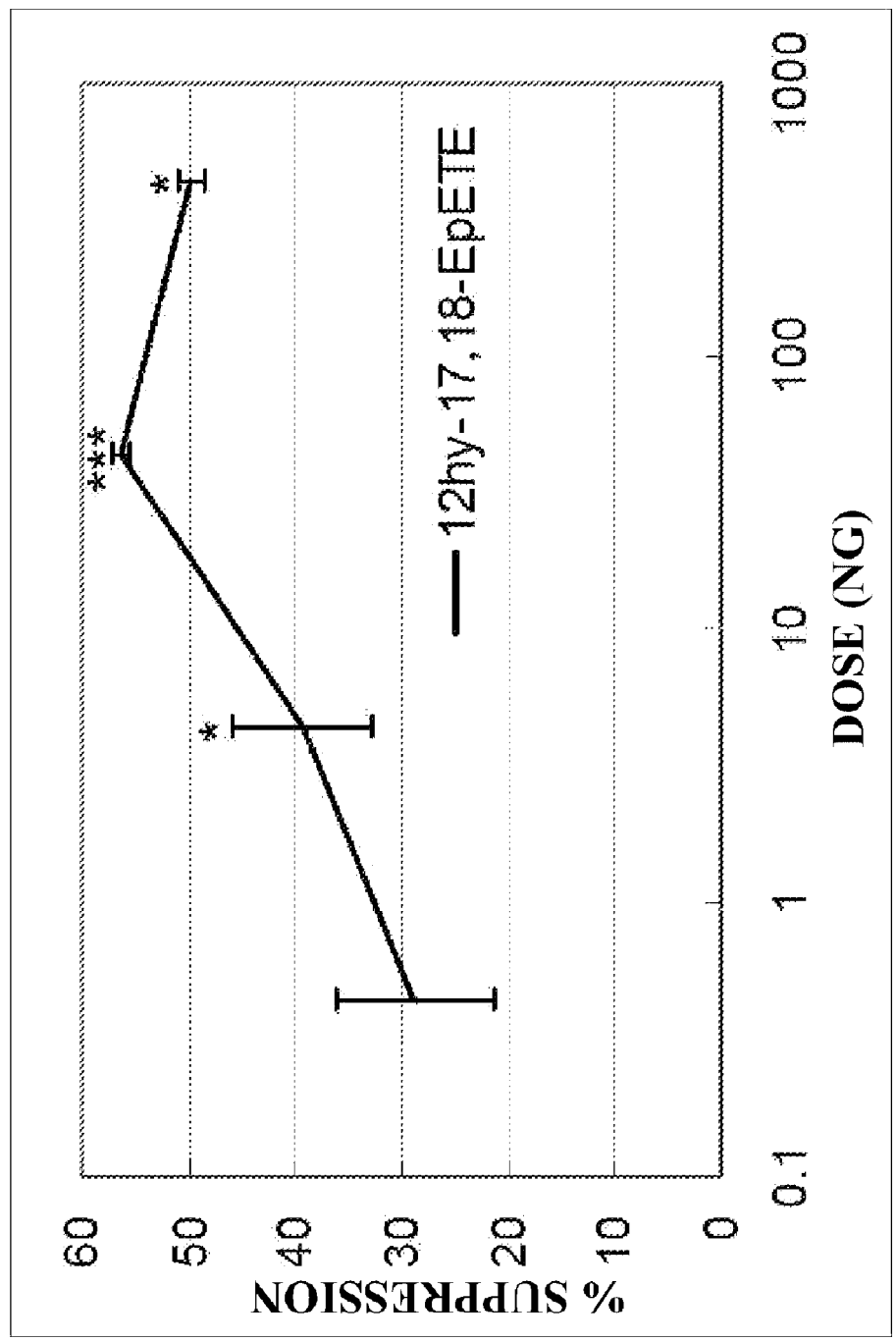
[FIG. 4C]

The results, as shown in FIG. 4C, showed that 12-hydroxy-17,18-epoxy ETE suppressed neutrophil infiltration approximately 40% in a very low dose of 10 ng/mouse and suppressed it 30% in a dose of 1 ng/mouse as well. This neutrophil-suppressing activity was equivalent to or better than that of 10 μg/mouse of the dexamethasone used as a control.

(c. Analysis Using an Acute Lung Injury Model)
Compounds of the present invention dissolved in physiological saline are injected from a caudal vein of C57BL/6J mice (7 weeks old, male; Japan CLEA). After 15 minutes, the mouse is anesthetized by intraperitoneal administration of a mixed solution of ketamine (Daiichi Sankyo Propharma) and xylazine (Bayer Medical). The trachea is exposed, and 25 μL of hydrochloric acid (pH 1.0, 0.1N; Sigma) is administered into the left bronchus. A group injected with only physiological saline and administered hydrochloric acid into the left bronchus after anesthetization (saline/HCl) and an intact group are used as control. Twelve hours later, the mice are sacrificed, and bronchopulmonary lavage (BAL) is performed twice by 0.7 mL of PBS. The cells in the BAL fluid are counted, and the cell populations are quantified by simply Giemsa staining using simple Giemsa staining solution Diffquick (Sysmex).

(Results)
When the compounds synthesized were evaluated by a zymosan peritonitis model, virtually all of the compounds of the present invention other than 12-hydroxy-17,18-epoxy ETE were found to possess activity to suppress infiltration of neutrophils in the early stage of inflammation in a low dose of 100 ng (FIGS. 4A and 4B). This activity was dose-dependent (FIG. 4C; actual data are as follows).

(Data on 12hy-17,18-EpETE)

TABLE 2

| Dose (ng) | Inhibition rate | SEM | T test |
|---|---|---|---|
| 0 (vehicle) | 0 | — | |
| 0.44 | 28.8% | 7.39 | 0.0983 |
| 4.35 | 39.3% | 6.59 | 0.0068 |
| 43.48 | 56.3% | 0.94 | 0.0001 |
| 434.8 | 49.8% | 1.30 | 0.0087 |

As shown in FIG. 4B, 4hy-19,20-EpDPE and Thy-19,20-EpDPE are seen to tend to suppress neutrophil infiltration at 100 ng and 500 ng, respectively. The possibility that the suppressive effect depends on the dose is therefore expected.

The neutrophil infiltration suppression data for 10-hydroxy-19,20-EpDTE, 14-hydroxy-19,20-EpDTE, and 17-hydroxy-19,20-EpDTE are shown in FIG. 4D. As shown, 14-hydroxy-19,20-EpDTE and 17-hydroxy-19,20-EpDTE present statistically significant effects. 10-Hydroxy-19,20-EpDTE is also seen to have a tendency toward suppression.

The actual data of FIGS. 4A, 4B, and 4D are as follows.

TABLE 3

| | 17,18-EpETE 100 ng | 5-hy-17,18-EpETE 100 ng | 8-hy-17,18-EpETE 100 ng | 12-hy-17,18-EpETE 100 ng | 15-hy-17,18-EpETE 100 ng |
|---|---|---|---|---|---|
| PMN (mean % suppression) | 0.0 | 50.6 | 10.4 | 48.4 | 42.9 |
| SE (standard error) | 9.31 | 4.35 | 6.54 | 2.21 | 7.90 |
| T test | | 0.044 | 0.256 | 0.003 | 0.007 |

TABLE 4

|  | 19,20-EpDPE 100 ng | 4-hy-19,20-EpDPE 100 ng | 4-hy-19,20-EpDPE 500 ng | 7-hy-19,20-EpDPE 100 ng | 7-hy-19,20-EpDPE 500 ng |
|---|---|---|---|---|---|
| PMN (mean % suppression) | 0.0 | 2.1 | 0.0 | 0.0 | 8.7 |
| SE (standard error) | 11.42 | 6.96 | 8.74 | 8.10 | 12.26 |
| T test |  | 0.861 | 0.510 | 0.711 | 0.571 |

TABLE 5

|  | 19,20-EpDPE 100 ng | 10-hy-19,20-EpDPE 100 ng | 13-hy-19,20-EpDPE 100 ng | 14-hy-19,20-EpDPE 100 ng | 17-hy-19,20-EpDPE 100 ng |
|---|---|---|---|---|---|
| PMN (mean % suppression) | 0.0 | 20.7 | 12.0 | 57.3 | 59.5 |
| SE (standard error) | 11.42 | 5.91 | 12.12 | 9.73 | 17.63 |
| T test |  | 0.093 | 0.477 | 0.040 | 0.048 |

TABLE 6

|  | Vehicle | 10hy-19,20-EpDTE 100 ng | 14hy-19,20-EpDTE 100 ng | 17hy-19,20-EpDTE 100 ng |
|---|---|---|---|---|
| PMN (mean % suppression) | 0.00 | 8.27 | 15.35 | 23.28 |
| SE (standard error) | 4.28 | 6.48 | 5.25 | 4.44 |
| T test |  | 0.266 | 0.028 | 0.003 |

Compounds found to be active in peritonitis should also be evaluated by models of neutrophil infiltration other than peritonitis, and analysis of an acute lung injury model can be performed. It is expected that these analyses will show these compounds to have a therapeutic effect on respiratory tract conditions characterized by neutrophil infiltration (ischemic reperfusion syndrome, idiopathic pulmonary fibrosis, and the like).

When zymosan is administered intraperitoneally, it is perceived by the macrophages resident in the abdominal cavity which release a neutrophil chemotactic factor. When this occurs, neutrophils in the peripheral blood interact with the vascular endothelial cells via integrins and the like, infiltrate between the endothelial cells, and migrate to the inflamed site. Therefore, the mechanism by which neutrophil infiltration is suppressed may possibly be that compounds of the present invention act on macrophages to suppress the release of neutrophil chemotactic factor or that they act on vascular endothelial cells or neutrophils and suppress infiltration. The point of action of compounds of the present invention can be clarified by assays using cells.

The possibility that compounds of the present invention suppress the infiltration of neutrophils to a site of inflammation by some mechanism and contribute to the convergence [sic] of inflammation is demonstrated.

Example 7

Human Neutrophil Migration Inhibition Study

A human neutrophil migration inhibition study was performed to measure the suppressive activity on neutrophils from another viewpoint.

Compounds produced in Examples 2-5 were used.

Neutrophils were isolated from human peripheral blood (see Serhan C. N et al. Biochemistry, 34, 14609-14615 (1995)), mixed to make $3 \times 10^5$ cells/200 µL with culture broth (RPMI-0.1% BSA) to which the target compound had been added, and incubated for 15 minutes at 37° C. They were then moved to a cell culture insert (24 wells, 3 µm pores; manufactured by Falcon), LTB4 (5 nM) was added to the lower layer as a chemotactic factor, and the number of neutrophils that moved to the lower layer was measured after two hours.

Compounds that inhibit migration can be analyzed in this way.

(Discussion)

From the results of the present example and other examples, the compounds of the present invention can be discussed as follows. The compounds of the present invention exhibit neutrophil suppression in vitro and in vivo. Therefore, the pharmaceutical composition of the present invention can be used as an agent for preventing and/or treating diseases such as encephalitis, myelitis and encephalomyelitis, meningitis, inflammatory multiple neuropathy, neuritis, dacryoadenitis, orbital inflammation, conjunctivitis (allergic conjunctivitis, spring keratoconjunctivitis, and the like), keratitis, chorioretinal scar, endophthalmitis, retrobulbar neuritis, retinopathy, glaucoma, cellulitis, otitis externa, perichondritis, tympanitis, salpingitis, mastoiditis, myringitis, labyrinthitis, pulpitis, periodontitis, sialitis, stomatitis, glossitis, thyroiditis, pericarditis, endocarditis, myocarditis, hypertension, cardiac failure, arteriosclerosis (atherosclerosis and the like), restenosis, ischemic reperfusion disorder, thrombosis (cardiac infarct, cerebral infarct, and the like), obesity, angiitis, vasculitis, multiple arteritis, lymphadenitis, lymphoma, Hodgkin's disease, eosinophilic disease (eosinophilia, pulmonary eosinophilia, pulmonary aspergillosis, and the like), inflammatory or obstructive airway disease (allergic rhinitis, chronic sinusitis, pneumonia, laryngitis, laryngotracheitis, bronchitis, asthma, acute lung disorder, acute respiratory distress syndrome, emphysema, chronic obstructive pulmonary disease, and the like), pleurisy, pneumoconiosis, mesothelioma, esophagitis, gastrojejunal ulcer, gastritis, duodenitis, food allergy, sepsis, hepatitis, hepatic fibrosis, hepatic cirrhosis, cholecystitis, pancreatitis, peritonitis, diabetes (type I diabetes, type II diabetes), inflammatory or allergic skin disease (atopic dermatitis, contact dermatitis (allergic contact dermatitis, irritant contact dermatitis, and the like), psoriasis, urticaria, photoallergic response, alopecia greata, and the like), skin hypertrophic disorder (skin eosinophilic granuloma, and the like), skin polymyositis, inflammation of subcutaneous adipose tissue, hyperthyroidism, sarcoidosis, autoimmune blood disease (hemolytic anemia, idiopathic thrombocytopenic purpura, and the like), (systemic) lupus erythematosus, relapsing polychondritis, multiple leptomeningitis, sclerodoma, Wegener's granulomatosis, dermatomyositis, chronic active hepatitis, myasthenia gravis, Stevens-Johnson syndrome, idiopathic sprue, autoimmune inflammatory bowel disease (ulcerative colitis, Crohn's disease, and the like), endocrine ophthalmopathy, sarcoidosis, alveolitis, chronic hypersensitivity pneumonitis, multiple sclerosis, primary biliary cirrhosis, uveitis, keratoconjunctivitis sicca, interstitial pulmonary fibrosis, iridocyclitis, psoriatic arthritis, glomerular nephritis, systemic sclerosis, systemic connective tissue disease (Sjogren's syndrome, Behcet's disease, diffuse myofascitis, and the like), interstitial myositis, inflammatory multiple joint disorder, inflammatory arthritis, rheumatoid arthritis, osteoarthritis, synovitis, bursitis, thecitis, chronic multiple myelitis, nephritis syndrome, tubulointerstitial nephritis, cystitis, prostatitis, orchitis, epididymitis, salpingitis, ovaritis, trachelitis, female pelvic inflammation, vulvovaginitis, organ transplant rejection, bone-marrow transplant rejection, and graft versus host disease, and/or an agent for treating burns or traumatic inflammation.

Example 8A

Dissolution Test

The solubility of a compound can be determined under conditions of 1% DMSO addition. A 10 mmol/L compound solution is prepared by DMSO, and 6 µL of the compound solution can be added to 594 µL of pH 6.8 artificial intestinal juice (brought to 1000 mL by adding 118 mL of 0.2 mol/L sodium hydroxide (NaOH) reagent solution and water to 250 mL of 0.2 mol/L potassium dihydrogen phosphate reagent solution). After standing for 16 hours at 25° C., the mixed solution can be suction filtered. The filtrate is diluted two-fold by methanol/water=1/1, and the concentration in the filtrate can be measured using HPLC or LC/MS/MS by the absolute calibration curve method.

Example 8B

Powder Solubility Test

A suitable amount of a compound of the present invention is placed in an appropriate container, and 200 µL each of JP-1 solution (brought to 1000 mL by adding water to 2.0 g of sodium chloride and 7.0 mL of hydrochloric acid), JP-2 solution (500 mL of water added to 500 mL of pH 6.8 phosphate buffer), and 20 mmol/L of sodium taurocholate (TCA)/JP-2 solution (JP-2 solution added to 1.08 g of TCA to make 100 mL) are added to each container. More compound of the present invention is added as appropriate when the entire amount dissolves after addition of the reagent solution. After closing tightly and shaking for one hour at 37° C., the solution is filtered and diluted two-fold by adding 100 µL of methanol to 100 µL of each filtrate. The dilution multiple is varied as needed. After checking that there are no air bubbles or precipitate, the containers are sealed and shaken. The compound of the present invention is quantified using HPLC by the absolute calibration curve method.

Example 9

Metabolic Stability Test

The subject compound is reacted for a set period of time using commercial pooled human liver microsomes, the residual percentage is calculated by comparing the reacted sample and the unreacted sample, and the extent to which the compound is metabolized by the liver can be evaluated.

Reaction can be carried out for 0 minutes or 30 minutes at 37° C. in the presence of 1 mmol/L of NADPH in 0.2 mL of buffer (50 mmol/L of Tris HCl, pH 7.4, 150 mmol/L of potassium chloride, and 10 mmol/L of magnesium chloride) containing 0.5 mg protein/mL of human liver microsomes (oxidative reaction). After the reaction, 50 µL of reaction solution can added to and mixed with 100 µL of methanol/acetonitrile=1/1 (v/v) solution and centrifuged for 15 minutes at 3000 rpm. The test compound in the supernatant is quantified by LC/MS/MS, and the residual percentage of test compound after reacting for 30 minutes can be calculated taking the amount of compound with 0 minutes reaction as 100%.

The results can be evaluated for various scenarios such as when the compound concentration is 0.5 µmol/L or the compound concentration is 2 µmol/L.

Example 10

CYP Inhibition Test

The degree to which production of the respective metabolites is inhibited by the subject compound can be evaluated using commercial pooled human liver microsomes taking the O-deethylation of 7-ethoxyresorufin (CYP 1A2), 4'-hydroxylation of mephenyloin (CYP 2C19), O-demethylation of dextromethorphan (CYP 2D6), and hydroxylation of terfenadine (CYP 3A4) as indicators as typical substrate metabolizing reactions of five key human CYP5 isozymes (CYP 1A2, 2C9, 2C19, 2D6, and 3A4).

The reaction conditions are as follows: substrate 0.5 µmol/L of ethoxyresorufin (CYP 1A2), 100 µmol/L of tolbutamide (CYP 2C9), 50 µmol/L of S-mephenyloin (CYP 2C19), 5 µmol/L of dextromethorphan (CYP 2D6), 1 µmol/L of terfenadine (CYP 3A4); reaction time, 15 minutes; reaction temperature, 37° C.; enzyme, pooled human liver microsomes 0.2 mg protein/mL; subject drug concentration 1, 5, 10, and 20 µmol/L (4 levels).

Each of the five substrates, human liver microsomes, and subject drug are added in the above compositions to 50 mmol/L of HEPES buffer as reaction solution in 96-well plates, NADPH, which is a coenzyme, is added, and the metabolic reaction that serves as the indicator is begun. After reacting for 15 minutes at 37° C., the reaction is stopped by adding methanol/acetonitrile=1/1 (v/v) solution. After centrifuging for 15 minutes at 3000 rpm, the resorufin (CYP 1A2 metabolite) in the supernatant can be quantified by fluorescent multi-label counter and the tolbutamide hydroxylate (CYP 2C9 metabolite), mephenyloin 4'-hydroxylate (CYP 2C19 metabolite), dextrorphan (CYP 2D6 metabolite), and terfenadine alcohol (CYP 3A4 metabolite) can be quantified by LC/MS/MS.

The residual activity (%) at the respective concentrations of the subject drug solution added can be calculated taking a reaction system with only DMSO, a solvent that dissolves the drug, added as the control (100%), and the $IC_{50}$ can be calculated by inverse estimation by a logistic model using the concentration and the suppression rate.

Example 11

CYP 3A4 Fluorescent MBI Test

The CYP 3A4 fluorescent MBI test is a test to investigate the potentiation of CYP 3A4 inhibition of a compound by metabolic reactions. The test is carried out using $E.\ coli$-expressed CYP 3A4 as the enzyme, debenzylating 7-benzyloxytrifluoromethylcoumarin (7-BFC) by CYP 3A4 enzyme, and taking the reaction that produces 7-hydroxytrifluoromethylcoumarin (HFC), a fluorescent metabolite, as the indicator.

The reaction conditions are as follows: substrate, 5.6 µmol/L of 7-BFC; pre-reaction time, 0 or 30 minutes; reaction time, 15 minutes; reaction temperature, 25° C. (room temperature); CYP 3A4 content ($E.\ coli$-expressed enzyme), during pre-reaction 62.5 pmol/mL, during reaction 6.25 pmol/mL (10-fold dilution); subject drug concentrations, 0.625, 1.25, 2.5, 5, 10, and 20 µmol/L (six levels).

The enzyme and subject drug solution in K-Pi buffer (pH 7.4) are added in the pre-reaction composition stated above as pre-reaction solution to a 96-well plate, and part is moved so as to be diluted 1/10 by substrate and K-Pi buffer to a separate 96-well plate. NADPH, a coenzyme, is added, and the reaction that serves as the indicator is begun (no pre-reaction). After reacting for the prescribed time, the reaction is stopped by adding acetonitrile/0.5 mol/L Tris(trishydroxyaminomethane)=4/1. NADPH is also added to the remaining pre-reaction solution, and the pre-reaction is begun (with pre-reaction). After pre-reacting for the prescribed time, part is moved so as to be diluted 1/10 by substrate and K-Pi buffer to another plate, and the reaction that serves as the indicator can be begun. After reacting for the prescribed time, the reaction can be stopped by adding acetonitrile/0.5 mol/L Tris(trishydroxyaminomethane)=4/1. The fluorescence of the metabolite 7-HFC in the plates that have undergone the respective indicator reactions can be measured by fluorescence plate reader (Ex=420 nm, Em=535 nm).

The residual activity (%) at the respective concentrations of the subject drug solution added can be calculated taking a reaction system with only DMSO, a solvent that dissolves the drug, added as the control (100%), and the $IC_{50}$ can be calculated by inverse estimation by a logistic model using the concentration and the suppression rate. The result can be taken to be (+) when the difference in $IC_{50}$ value is 5 µmol/L or higher and to be (−) when it is 3 µmol/L or lower.

Example 12

FAT Test

Ten milliliters of liquid nutrient medium (2.5% Oxoid nutrient broth No. 2) can be inoculated with cryopreserved *Salmonella typhimurium* (*Salmonella typhimurium* TA98 and TA100) and shake pre-cultured for 10 hours at 37° C. For TA98, the culture broth is removed by centrifuging (2000×g, 10 minutes) 9 mL of bacterial solution. The cells are suspended in 9 mL of Micro F buffer (dipotassium hydrogen phosphate ($K_2HPO_4$): 3.5 g/L, potassium dihydrogen phosphate ($KH_2PO_4$): 1 g/L, ammonium sulfate (($NH_4)_2SO_4$): 1 g/L, trisodium citrate dehydrate: 0.25 g/L, magnesium sulfate heptahydrate ($MgSO_4.7H_2O$): 0.1 g/L) and added to 110 mL of exposure medium (Micro F buffer containing biotin: 8 µg/mL, histidine: 0.2 µg/mL, glucose: 8 mg/mL). For TA100, 120 mL of exposure medium is added per 3.16 mL of bacterial solution, and a test bacterial solution can be prepared. A quantity of 12 µL each of the subject substance DMSO solution (8-step dilution from a maximum dose of 50 mg/mL by a common factor of 2), DMSO as a negative control, and 50 µg/mL 4-nitroquinoline-1-oxide DMSO solution for TA98 and 0.25 µg/mL 2-(2-furyl)-3-(5-nitro-2-furyl)acrylamide DMSO solution for TA100 under non-metabolic activation conditions and 40 µg/mL 2-aminoanthracene DMSO solution for TA98 and 20 µg/mL 2-aminoanthracene DMSO solution for TA100 under metabolic activation conditions as positive controls and 588 µL of test bacterial solution (mixed solution of 498 µL of test bacterial solution and 90 µL of S9 mix under metabolic activation conditions) can be mixed and shake cultured for 90 minutes at 37° C. A quantity of 460 µL of bacterial solution that can be exposed to the subject substance is mixed with 2300 µL of indicator medium (Micro F buffer containing biotin: 8 µg/mL, histidine: 0.2 µg/mL, glucose: 8 mg/mL, bromocresol blue: 37.5 µg/mL), dispensed in 50 µL aliquots into 48-well/dose microplates, and static cultured for three days at 37° C. Wells containing bacteria that have acquired the ability to grow by mutation of an amino acid (histidine) synthase gene change from violet to yellow due to a change in pH. Therefore, the number of wells with bacteria growing that can turn yellow among the 48 wells per dose can be counted and evaluated by comparison with a negative control group. The result can be evaluated by showing those negative for mutagenicity as (−) and those that are positive as (+).

Example 13 hERG Test

The action on the delayed rectifier K+ current ($I_{K+}$), which plays an important role in the ventricular repolarization process, can be studied using HEK293 cells that express the human ether-a-go-go-related gene (hERG) channel to evaluate the risk of electrocardiographic QT interval prolongation.

Using a fully automatic patch clamp system (PatchXpress 7000A, Axon Instruments Inc.), the $I_{K+}$ induced when a cell can be held at a membrane potential of −80 mV, then subjected to depolarizing stimulation of +50 mV for 2 seconds and to repolarizing stimulation of −50 mV for 2 seconds is recorded by the whole cell patch clamp method. After the current generated has stabilized, extracellular fluid in which the subject substance has been dissolved in the target concentration (NaCl: 137 mmol/L, potassium chloride (KCl): 4 mmol/L, calcium chloride dehydrate ($CaCl_2.2H_2O$): 1.8 mmol/L, magnesium chloride hexahydrate ($MgCl_2.6H_2O$): 1 mmol/L, glucose: 10 mmol/L, HEPES (4-(2-hydroxyethyl)-1-piperazineethanesulfonic acid): 10 mmol/L, pH=7.4) is applied to the cell for 10 minutes under room temperature conditions. The absolute value of the maximum tail current can be measured taking the current value at the retained membrane potential as a standard from $I_{K+}$ obtained using analysis software (DataXpress ver. 1, Molecular Devices Corporation). The inhibition rate versus the maximum tail current before application of the subject substance can also be calculated, and the effect of the subject substance on $I_{K+}$ can be evaluated by comparison with the vehicle group (0.1% dimethyl sulfoxide solution). The results can show the inhibition rate at a compound concentration of 1 µmol/L.

Example 14

BA Test

The oral absorbability can be carried out [sic] using the following BA test.

The experimental materials and method are shown below.

(1) Animals used: Rats or mice were used.

(2) Rearing conditions: Rats were given solid feed and sterilized tap water ad libitum.

(3) Doses and grouping: Predetermined doses were administered orally or intravenously. Groups were established as follows. (Dose varied for every compound)

Oral administration: 1-30 mg/kg (n=2-3)

Intravenous administration: 0.5-10 mg/kg (n=2-3)

(4) Preparation of administration solution: Administered as a solution or suspension in oral administration. Administered solubilized in intravenous administration.

(5) Administration method: Oral administration was performed forcibly to the stomach using an oral probe. Intravenous administration was performed from a caudal vein by a syringe with an injection needle attached.

(6) Evaluation parameters: Blood samples were taken over time, and the drug concentration in the plasma was measured using LC/MS/MS.

(7) Statistical analysis: For the changes in the plasma concentration, the plasma concentration-time area under the curve (AUC) was calculated by a nonlinear method of least squares program WinNonlin (registered trademark), and the bioavailability (BA) was calculated from the AUC of the oral group and the intravenous group.

The results can show, for example, the BA value at an oral dose of 1 mg/kg in the rat.

Formulation Examples

A few formulation examples appear below and are not intended to in any way limit the scope of the invention.

Example 15

Formulation Example 1

Tablet

Tablets comprising the following composition are produced by the usual method for pharmaceutical ingredients identified by the present invention.

| Compound of the present invention | 100 mg |
| Lactose | 60 mg |
| Potato starch | 30 mg |
| Polyvinyl alcohol | 2 mg |
| Magnesium stearate | 1 mg |
| Tar dye | Trace |

Example 16

Formulation Example 2

Powder

Powders comprising the following composition are produced by the usual method for pharmaceutical ingredients identified by the present invention.

| Compound of the present invention | 150 mg |
| Lactose | 280 mg |

Example 17

Formulation Example 3

Syrup

A syrup comprising the following composition is produced by the usual method for pharmaceutical ingredients identified by the present invention.

| Compound of the present invention | 100 mg |
| Refined sugar | 40 g |
| Ethyl p-hydroxybenzoate | 40 mg |
| Propyl p-hydroxybenzoate | 10 mg |
| Chocolate flavor | 0.1 cc |

This is brought to a total volume of 100 cc by adding water.

The present invention has been illustrated above using preferred embodiments of the present invention, but the present invention should not be interpreted as being limited to these embodiments. It is understood that the scope of the present invention is only to be interpreted by the claims. It is understood that a person skilled in the art can implement an equivalent scope based on the description of the present invention and general technical knowledge from the description of specific preferred embodiments of the present invention. It is understood that the content of patents, patent applications, and references cited in the present specification should be incorporated into the present specification by reference as if the content itself is specifically described in the present specification.

INDUSTRIAL APPLICABILITY

The present invention provides a drug to treat conditions or disorders related to neutrophil suppression, a compound used therein, pharmaceutically acceptable salts thereof, hydrates of these, and other such prodrugs. The compounds of the present invention present an excellent suppressive action on neutrophils, as described in the present specification. Therefore, the present invention is useful in the pharmaceutical industry and the like.

The invention claimed is:

1. A compound selected from the group consisting of:

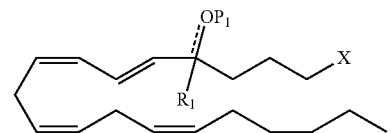

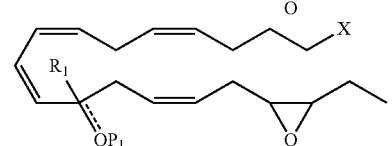

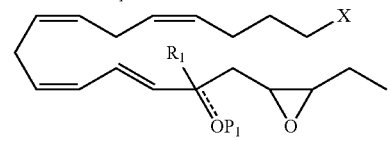

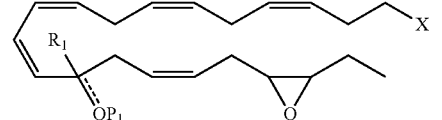

and

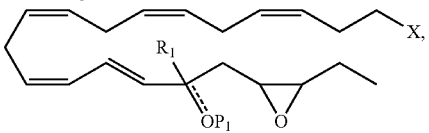

hydrates of the compound, pharmaceutically acceptable salts of the compound, and hydrates of the salts; wherein, when

----- is a single bond,
$P_1$ is hydrogen, alkyl, or hydroxy and
$R_1$ is hydrogen, or substituted or unsubstituted, branched or unbranched alkyl;

when $\dashed$ is a double bond, $P_1$ and $R_1$ are not present;
X is —C(O)OR$_2$;
R$_2$ is a hydrogen, substituted or unsubstituted alkyl, or substituted or unsubstituted aryl; and
double bonds of the compound may each be independently in either a cis or trans configuration.

2. The compound according to claim 1, selected from the group consisting of:

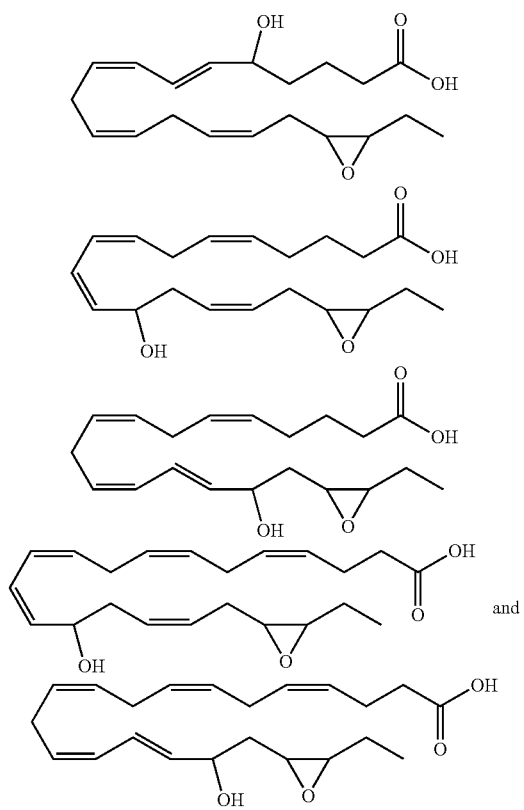

or hydrates of the compound, pharmaceutically acceptable salts of the compound, and hydrates of the salts.

3. A neutrophil suppressant composition comprising a compound according to claim 1, a hydrate of the compound, a pharmaceutically acceptable salt of the compound, or a hydrate of the salt.

4. A pharmaceutical composition comprising a compound according to claim 1, a hydrate of the compound, a pharmaceutically acceptable salt of the compound, or a hydrate of the salt.

5. The compound according to claim 1, which is:

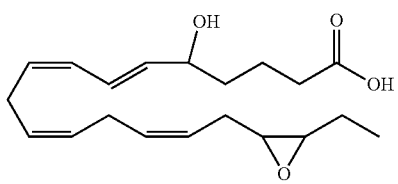 [SMILES: CCC1OC1C/C=C\C/C=C\C/C=C\C=C\C(O)CCCC(=O)O]

or hydrates of the compound, pharmaceutically acceptable salts of the compound, and hydrates of the salts.

6. The compound according to claim 1, which is:

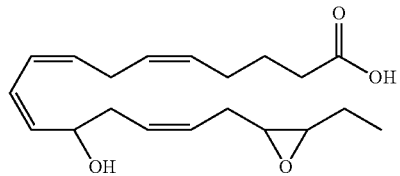 [SMILES: CCC1OC1C/C=C\CC(O)/C=C\C=C/C/C=C\CCCC(=O)O]

or hydrates of the compound, pharmaceutically acceptable salts of the compound, and hydrates of the salts.

7. The compound according to claim 1, which is:

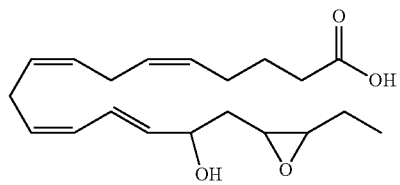 [SMILES: CCC1OC1CC(O)/C=C/C=C\C/C=C\C/C=C\CCCC(=O)O]

or hydrates of the compound, pharmaceutically acceptable salts of the compound, and hydrates of the salts.

8. The compound according to claim 1, which is:

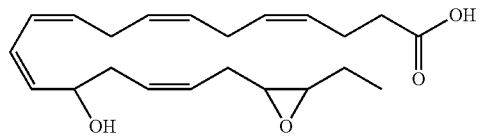 [SMILES: CCC1OC1C/C=C\CC(O)/C=C\C=C/C/C=C\C/C=C\CCC(=O)O]

or hydrates of the compound, pharmaceutically acceptable salts of the compound, and hydrates of the salts.

9. The compound according to claim 1, which is:

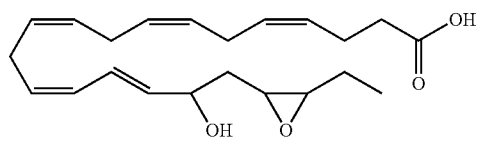 [SMILES: CCC1OC1CC(O)/C=C/C=C\C/C=C\C/C=C\C/C=C\CCC(=O)O]

or hydrates of the compound, pharmaceutically acceptable salts of the compound, and hydrates of the salts.

10. A neutrophil suppressant composition comprising a compound according to claim 2, a hydrate of the compound, a pharmaceutically acceptable salt of the compound, or a hydrate of the salt.

11. A pharmaceutical composition comprising a compound according to claim 2, a hydrate of the compound, a pharmaceutically acceptable salt of the compound, or a hydrate of the salt.

* * * * *